(12) United States Patent
Maruyama et al.

(10) Patent No.: US 8,945,154 B2
(45) Date of Patent: Feb. 3, 2015

(54) TISSUE CLOSING DEVICE

(75) Inventors: Tomoji Maruyama, Kanagawa (JP); Masakatsu Kawaura, Kanagawa (JP); Ryou Nakamoto, Kanagawa (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 1861 days.

(21) Appl. No.: 12/067,744

(22) PCT Filed: Sep. 28, 2006

(86) PCT No.: PCT/JP2006/319917
§ 371 (c)(1),
(2), (4) Date: Jul. 25, 2008

(87) PCT Pub. No.: WO2007/037516
PCT Pub. Date: Apr. 5, 2007

(65) Prior Publication Data
US 2009/0270885 A1    Oct. 29, 2009

(30) Foreign Application Priority Data

Sep. 29, 2005  (JP) ................................ 2005-285402
Jul. 12, 2006  (JP) ................................ 2006-192072

(51) Int. Cl.
*A61B 17/10* (2006.01)
*A61B 17/00* (2006.01)
*A61B 17/04* (2006.01)

(52) U.S. Cl.
CPC ... *A61B 17/0057* (2013.01); *A61B 2017/00575* (2013.01); *A61B 2017/00606* (2013.01);
(Continued)

(58) Field of Classification Search
USPC ......... 606/139, 142, 143, 144, 148, 151, 103, 606/181–185, 205–507, 157; 289/17
See application file for complete search history.

(56) References Cited

U.S. PATENT DOCUMENTS

| 4,917,089 A | 4/1990 | Sideris |
| 5,021,059 A * | 6/1991 | Kensey et al. ................ 606/213 |

(Continued)

FOREIGN PATENT DOCUMENTS

| EP | 0 362 113 B1 | 4/1990 |
| WO | WO 2005/063133 A1 | 7/2005 |

OTHER PUBLICATIONS

* Form PCT/ISA/210 (International Search Report) dated Jul. 11, 2007.

(Continued)

*Primary Examiner* — Ashley Fishback
*Assistant Examiner* — Jing Ou
(74) *Attorney, Agent, or Firm* — Buchanan Ingersoll & Rooney PC

(57) ABSTRACT

A tissue closing device includes an elongate arrangement device of which a distal end portion can penetrate an opening penetrating an living tissue membrane and which has a handling portion on the proximal side, and a clip which is detachably retained at a distal end portion of the arrangement device and which closes the opening. The arrangement device includes a retaining member for detachably retaining the clip and pulling the clip in the proximal direction, a cover tube, and a fixed tube. The handling portion has a first elastic member. When a restriction for maintaining the coil spring in a deformed state is canceled, the thread is moved to the proximal direction by the restoring force of the coil spring in the condition where the clip is locked to a distal end portion of the fixed tube, and the clip is pulled in the axial direction by the thread, whereby a deformation portion is deformed.

41 Claims, 37 Drawing Sheets

(52) U.S. Cl.
CPC .................. *A61B2017/00619* (2013.01); *A61B 2017/00623* (2013.01); *A61B 2017/0475* (2013.01); *A61B 2017/0496* (2013.01)
USPC .......................................... 606/142; 606/213

(56) References Cited

U.S. PATENT DOCUMENTS

| | | | |
|---|---|---|---|
| 5,282,827 A | 2/1994 | Kensey et al. | |
| 5,350,399 A * | 9/1994 | Erlebacher et al. | 606/213 |
| 5,591,196 A * | 1/1997 | Marin et al. | 606/198 |
| 5,662,681 A * | 9/1997 | Nash et al. | 606/213 |
| 6,132,440 A | 10/2000 | Hathaway et al. | |
| 6,689,140 B2 * | 2/2004 | Cohen | 606/103 |
| 6,860,895 B1 * | 3/2005 | Akerfeldt et al. | 606/215 |
| 7,160,310 B2 * | 1/2007 | Nesper et al. | 606/148 |
| 7,875,043 B1 * | 1/2011 | Ashby et al. | 606/148 |
| 2002/0173820 A1 * | 11/2002 | Akerfeldt et al. | 606/225 |
| 2003/0083669 A1 * | 5/2003 | Gleason | 606/103 |
| 2003/0158578 A1 | 8/2003 | Pantages et al. | |
| 2004/0002681 A1 * | 1/2004 | McGuckin et al. | 604/116 |
| 2006/0135991 A1 | 6/2006 | Kawaura et al. | |
| 2006/0167464 A1 * | 7/2006 | Allen et al. | 606/103 |
| 2006/0241579 A1 | 10/2006 | Kawaura et al. | |
| 2006/0265006 A1 * | 11/2006 | White et al. | 606/232 |
| 2006/0265008 A1 | 11/2006 | Maruyama et al. | |
| 2008/0065121 A1 | 3/2008 | Kawaura et al. | |

OTHER PUBLICATIONS

* Form PCT/ISA/237 (Written Opinion of the International Searching Authority) dated Jul. 11, 2007.

* cited by examiner

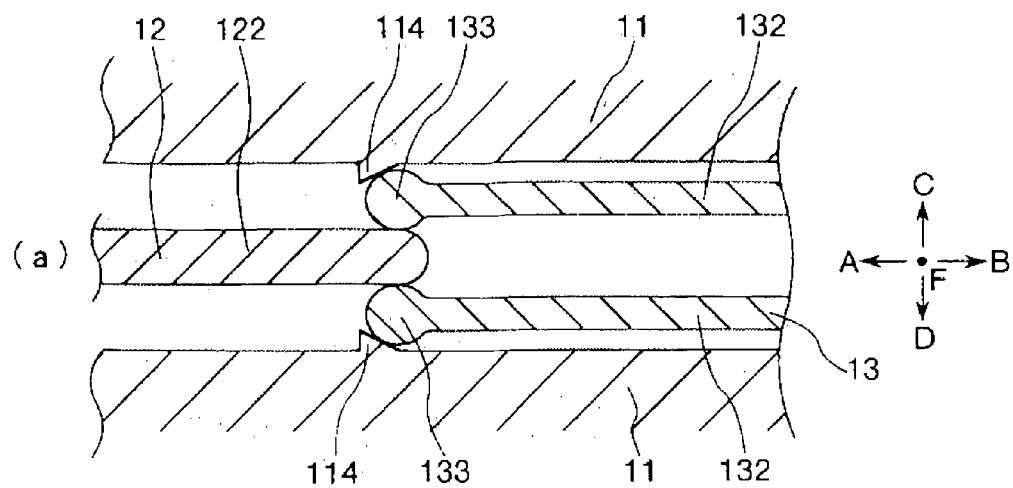
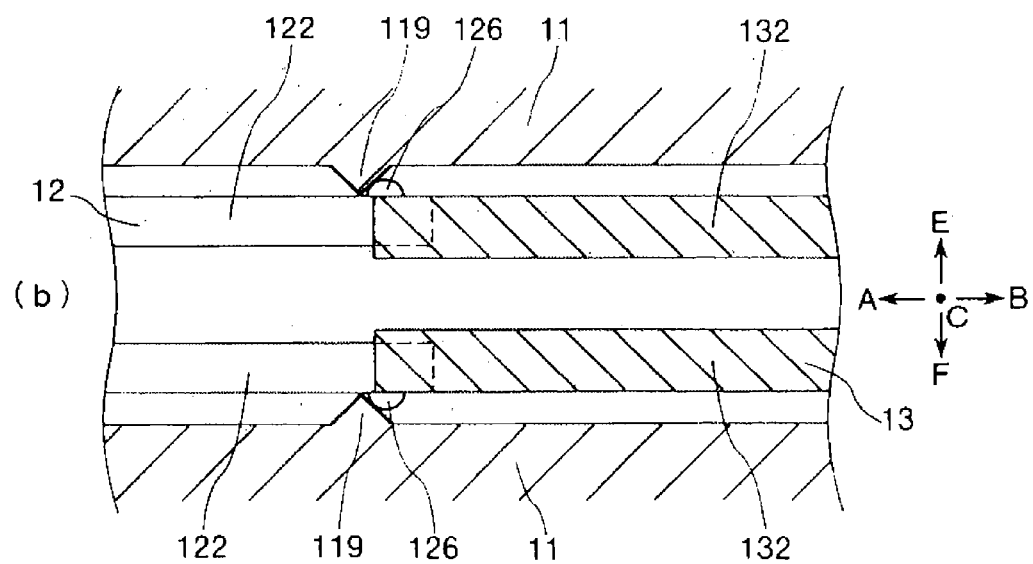
FIG. 16

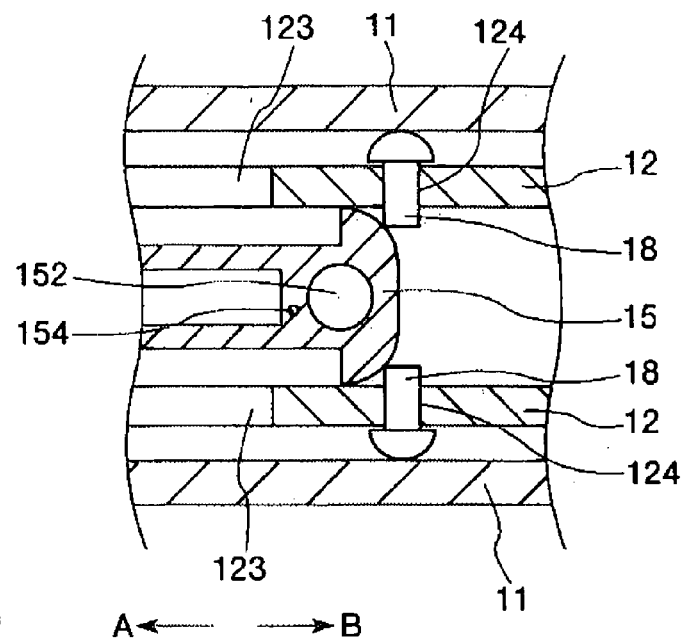
FIG. 19   A◄──►B
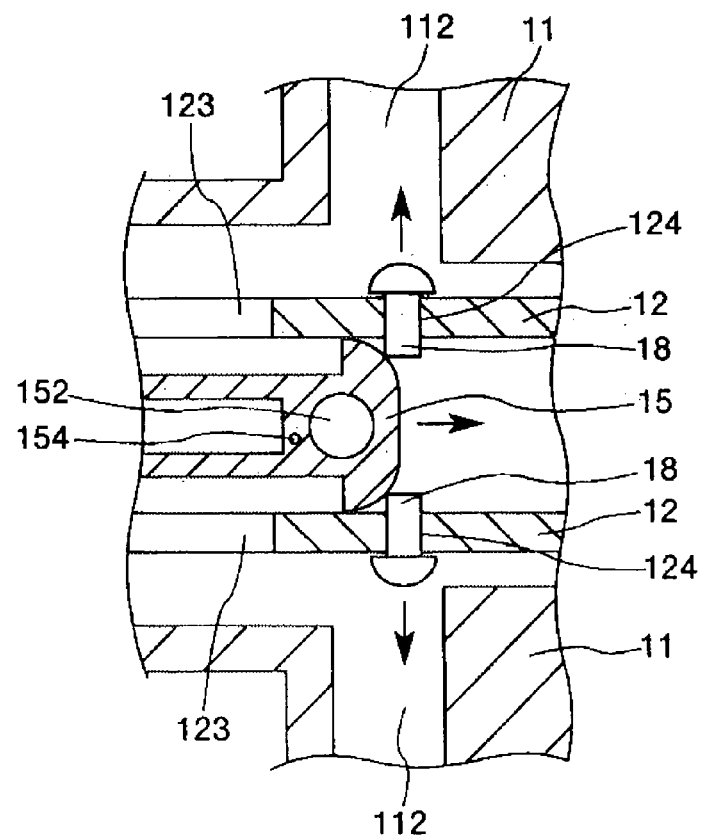
FIG. 20   A◄──►B

TISSUE CLOSING DEVICE

TECHNICAL FIELD

The present invention generally relates to a tissue closing device More specifically, The present invention pertains to a living body tissue closing device Low-invasion operations carried out by inserting a device for diagnosis or treatment, such as a catheter, into a blood vessel or some other tissue are known and performed on a quite often basis For example, to treat a constriction of the coronary artery of the heart, it is necessary to insert a device such as a catheter into a blood vessel in order to perform therapeutic on the constriction This insertion of an instrument such a catheter into a blood vessel is normally performed through a puncture formed by dissecting or puncturing the femoral region After the therapeutic treatment is completed, it is necessary to perform a stanching operation to stop the bleeding through the puncture However, since the blood pressure upon bleeding (bleeding blood pressure) from the femoral artery is relatively high, it is oftentimes necessary for a person involved in the medical procedure to use a finger of their hand to press down on the site for a relatively long period of time In recent years, to perform the stoppage of bleeding more readily and with greater certainty, a variety of devices has been developed which is adapted to be inserted through a wound hole to close an opening formed in a blood vessel For example, U.S. Pat. No. 5,282,827 discloses a device configured such that a thread is held at a proximal end of the device by a ball retained by a spring, and when the device is pulled off, the thread slides while keeping a fixed thread tension, whereby the device is pulled off Finally, in the condition where an anchor (blood vessel inside lock member) is disposed at the position of the hole formed in the blood vessel, a nonwoven fabric plug (seal member) is pressed with a pushing-in pipe (packing member) while pulling the thread (while compressing with the thread), to flatten the plug In this manner, the hole formed in the blood vessel is closed with a closure However, in the device described in the above-mentioned patent, the operator must manually perform the operation of flattening the plug by pressing the plug with the pushing-in pipe while pulling the thread, and labor and time are required for the operation In addition, particularly in the case of a non-skilled operator, there is fear about uncertainty of the operation

SUMMARY OF THE INVENTION

According to one aspect, a tissue closing device for closing an opening penetrating a living tissue comprises a closure for closing the opening, the closure comprising a seal portion adapted to cover the opening and a periphery of the opening from one side of a wall of a living body cavity, and a deformable deformation portion, and an arrangement device detachably retaining the closure to arrange the closure at a position to close the opening The arrangement device comprises a lock member having an elongate shape such as to be able to pass through the opening and locking at least a part of the closure in a retaining state, a handling portion provided on the proximal side of the lock member The handling portion comprises an actuating member for moving the closure and the lock member relative to each other and a trigger means for actuating the actuating member The closure and the lock member are moved relative to each other in the condition where the closure is locked by the lock member with the actuating member actuated by the trigger means, whereby the deformation portion is deformed According to the present invention, when the restriction for retaining the actuating member (first elastic member) in the active state is canceled (when the actuating member is put into actuation), the closure and the lock member are moved relative to each other by the restoring force of the first elastic member and the deformation portion of the closure is automatically deformed, in the condition where the closure is locked to the lock member, so that it is unnecessary for the operator to manually perform an operation of deforming the deformation portion of the closure Therefore, a stanching work for a wound hole formed in an in vivo tissue membrane such as a blood vessel wall can be performed readily, speedily and assuredly Namely, the wound hole can be closed (closed up) easily, speedily and assuredly, and perfect stanching can be achieved

BRIEF DESCRIPTION OF THE DRAWINGS

FIGS. 16(a) and 16(b) are sectional views for illustrating an action (operation) of the tissue closing device shown in FIG. 1

FIG. 19 is a sectional view for illustrating an action (operation) of the tissue closing device shown in FIG. 1

FIG. 20 is a sectional view for illustrating an action (operation) of the tissue closing device shown in FIG. 1

DETAILED DESCRIPTION OF THE PREFERRED EMBODIMENTS

Now, the tissue closing device will be described in detail below, based on preferred embodiments thereof shown in the accompanying drawings

First Embodiment

Figure 1:
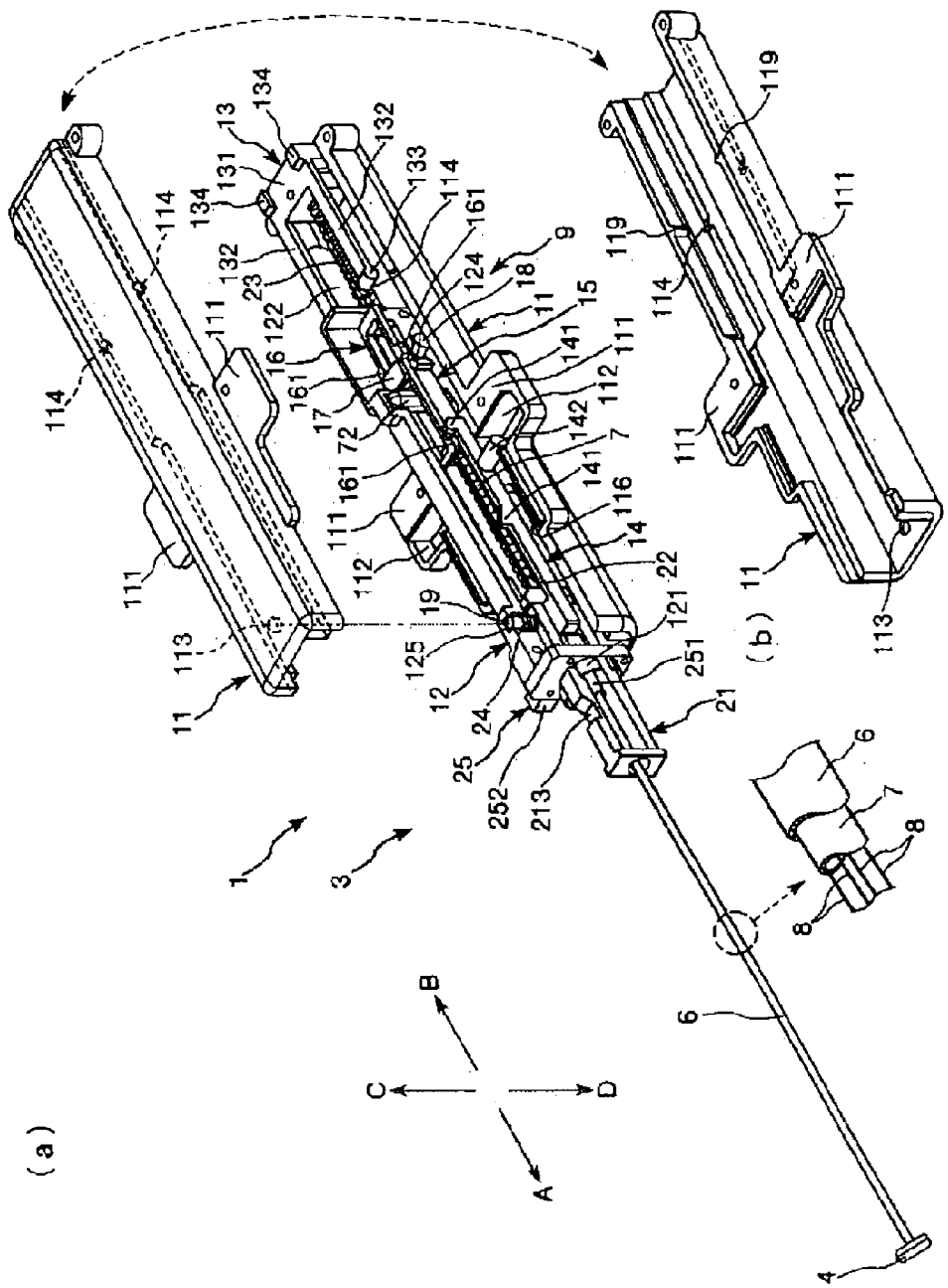
FIGS. 1(a) and 1(b) are perspective views of a first embodiment of the tissue closing device as disclosed herein
Figure 2:
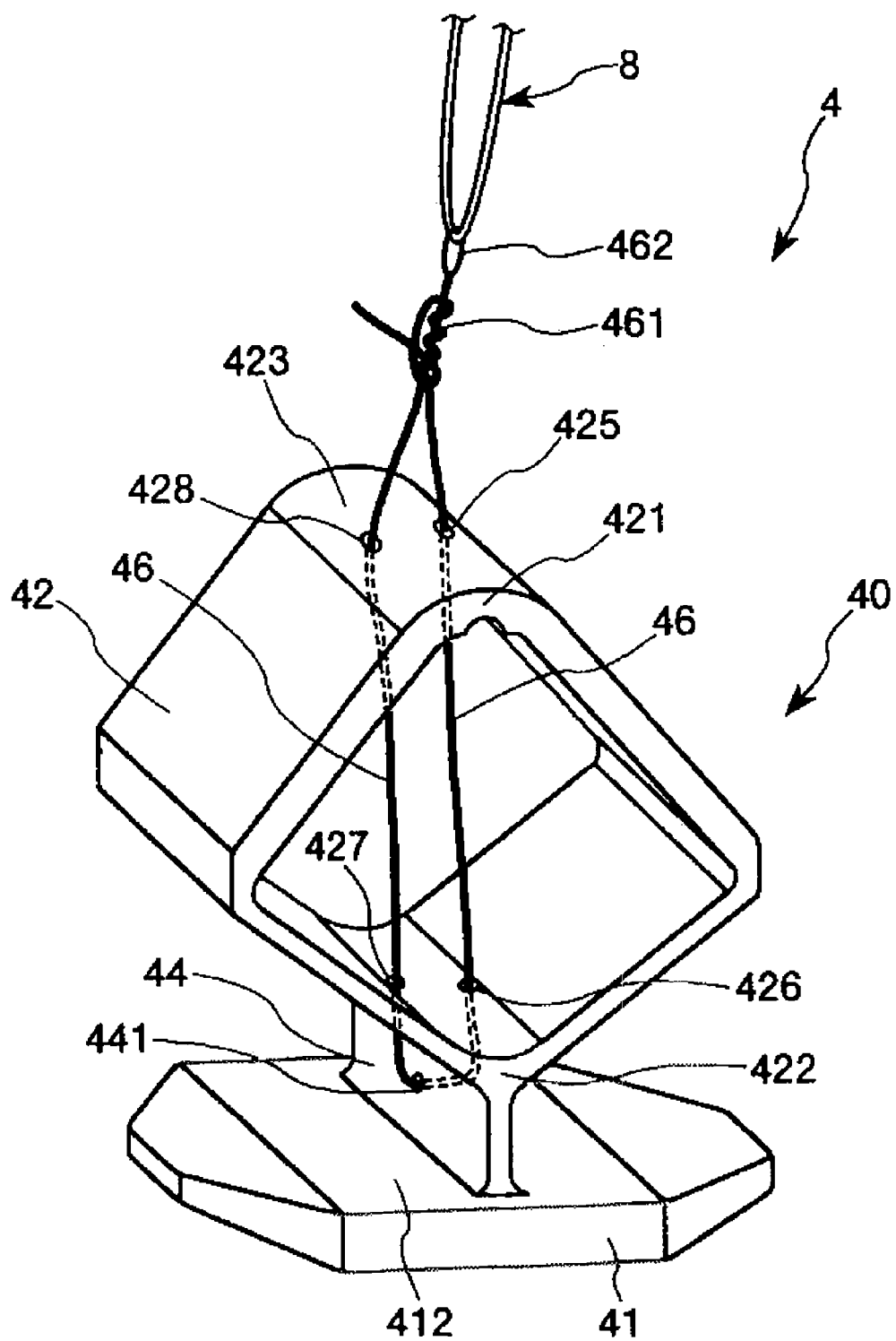
FIG. 2 is a perspective view of a closure in the tissue closing device shown in FIG. 1
Figure 3:
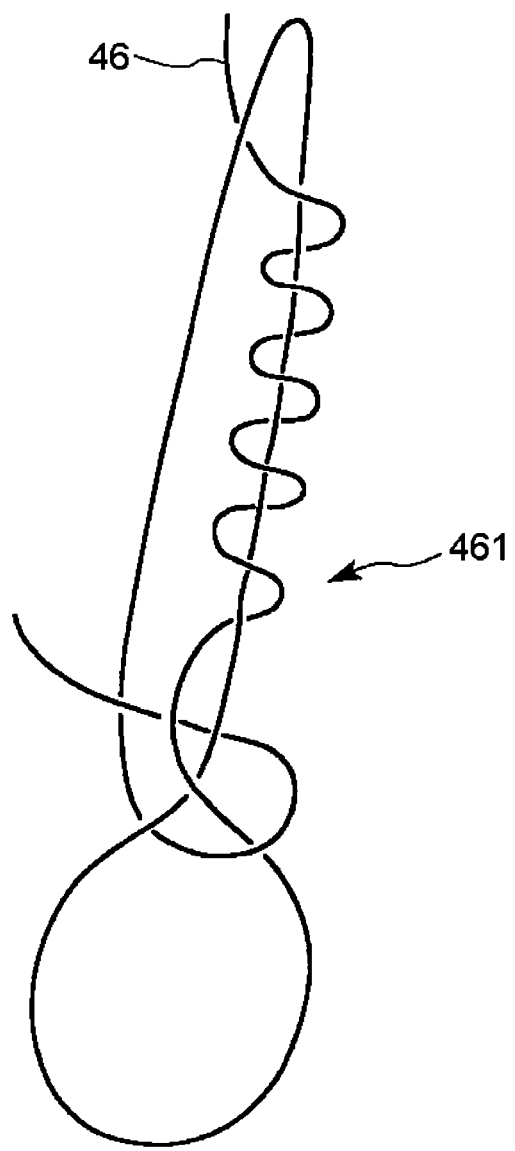
FIG. 3 is an illustration of one example of a knot of the closure in the tissue closing device shown in FIG. 1
Figure 4:
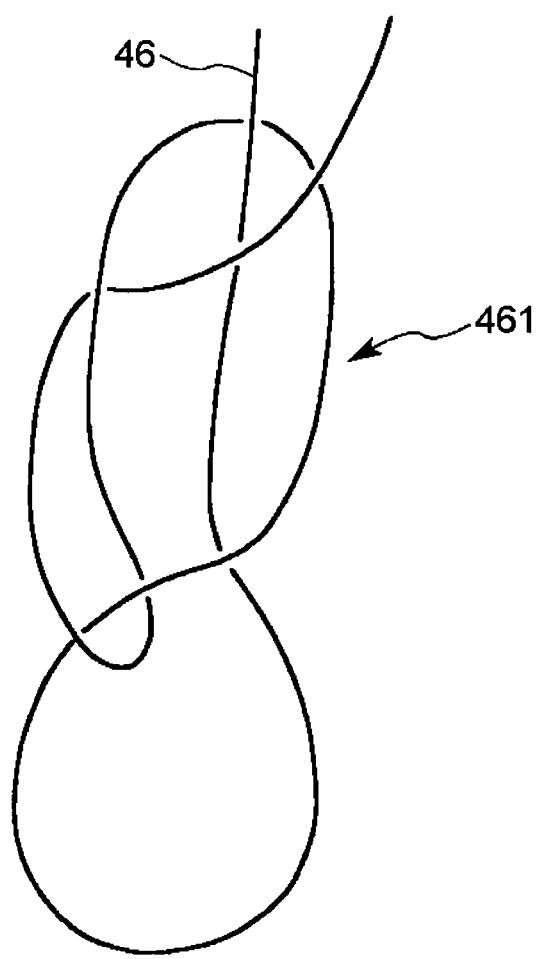
FIG. 4 is an illustration of another example of the knot of the closure in the tissue closing device shown in FIG. 1
Figure 5:
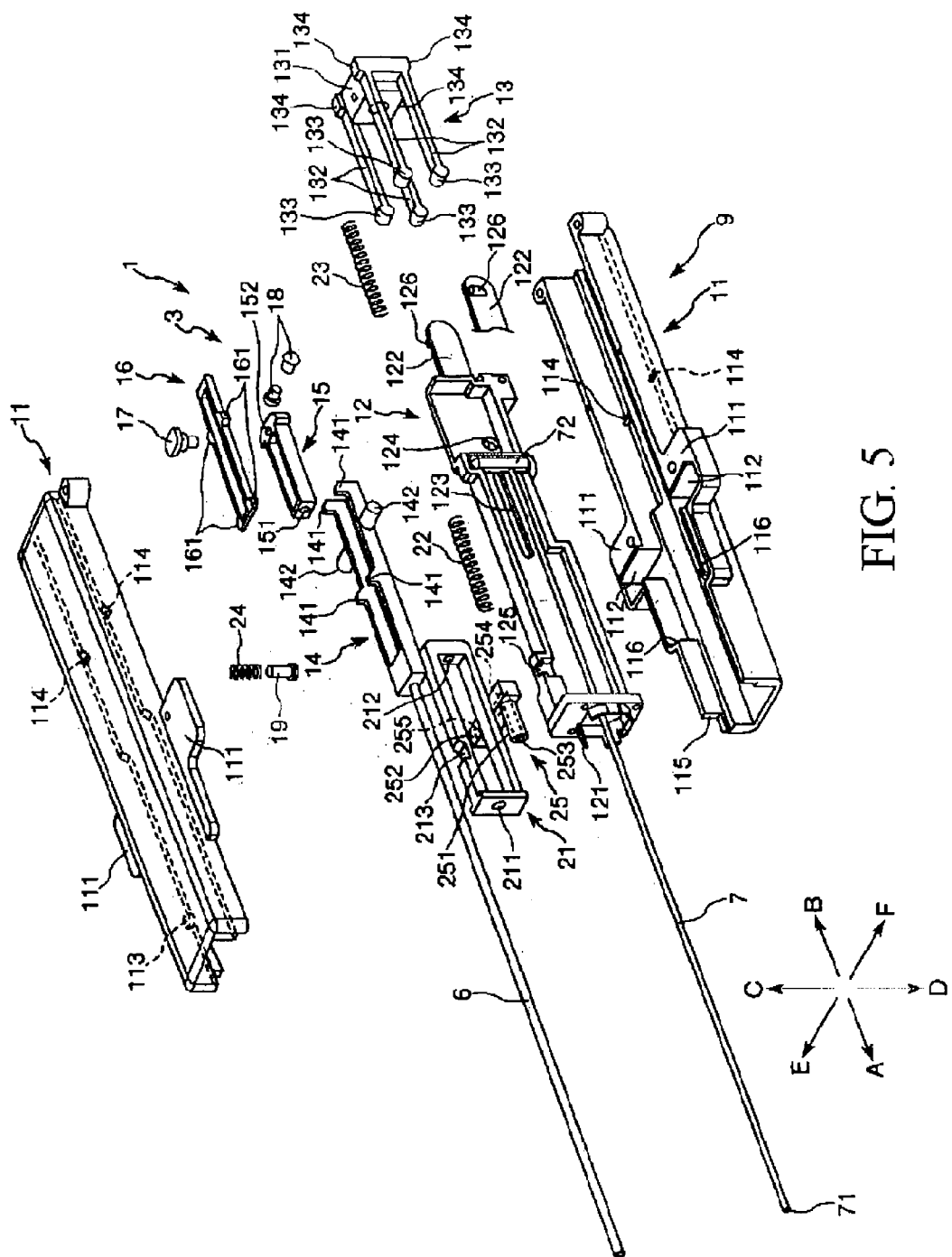
FIG. 5 is an exploded perspective view (members (component parts)) of the tissue closing device shown in FIG. 1
Figure 6:
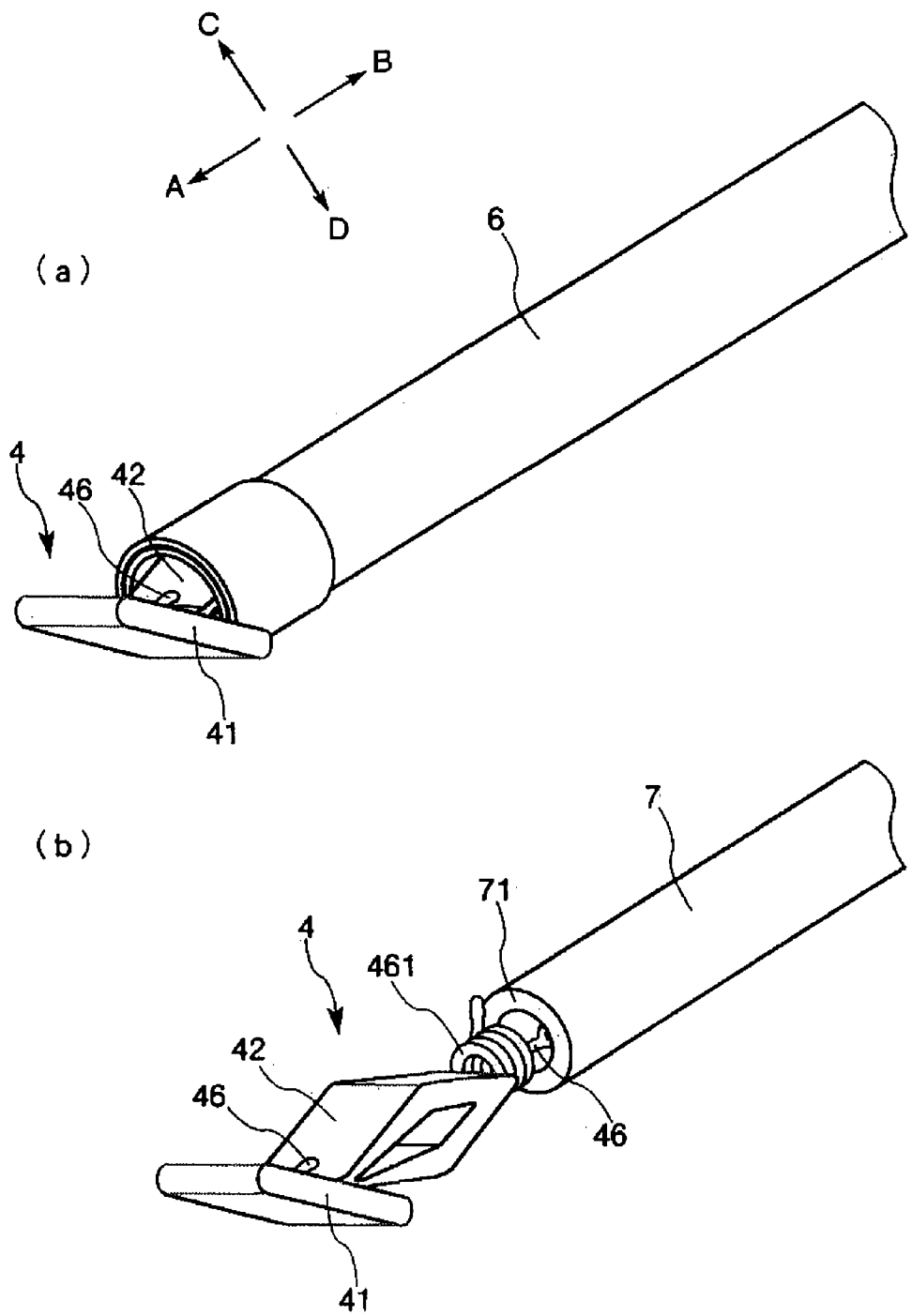
FIGS. 6(a) and (b) are perspective views of a distal end portion of the tissue closing device shown in FIG. 1
Figure 7:
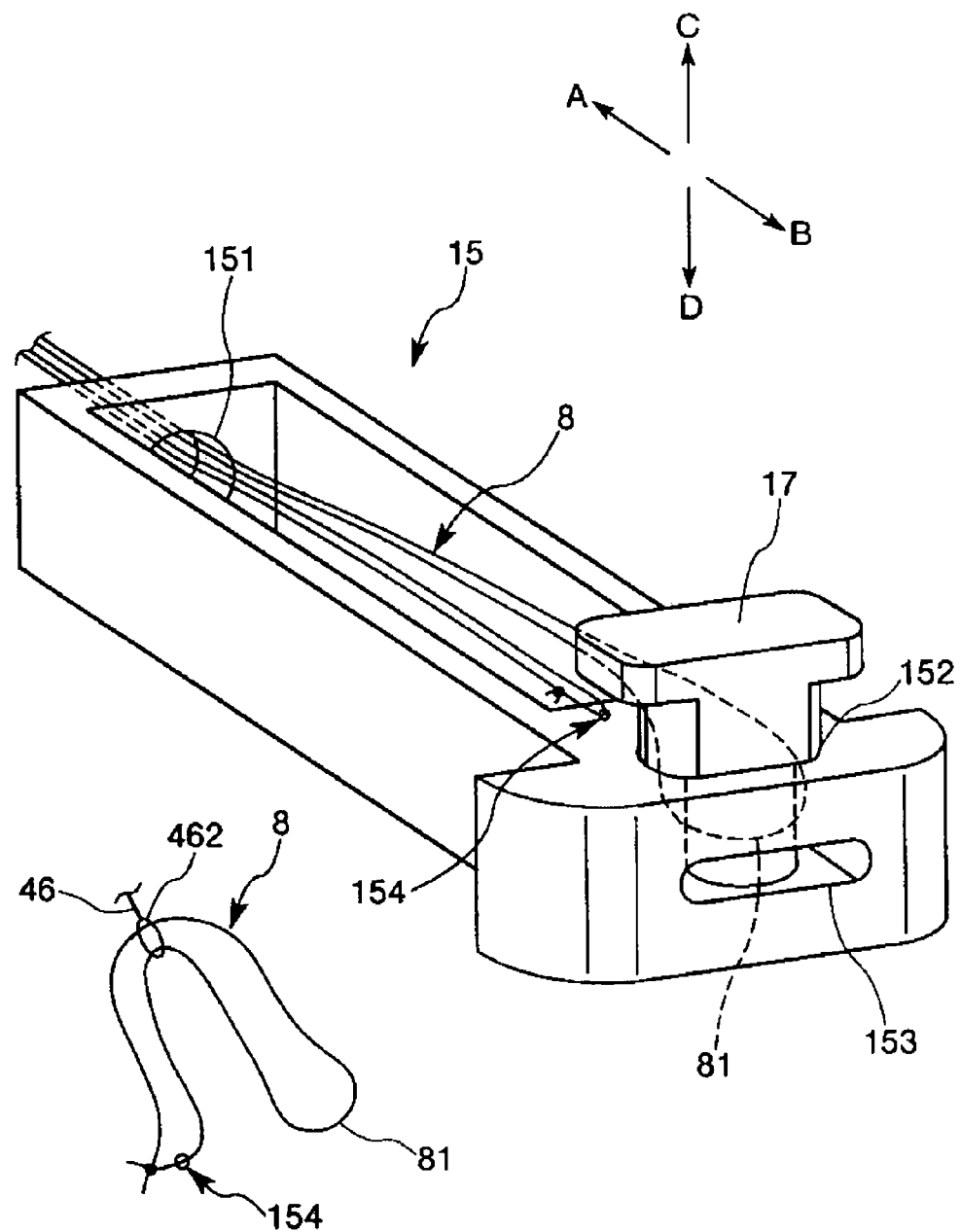
FIG. 7 is a perspective view showing a thread support portion, a pin and a thread in the tissue closing device shown in FIG. 1
Figure 9:
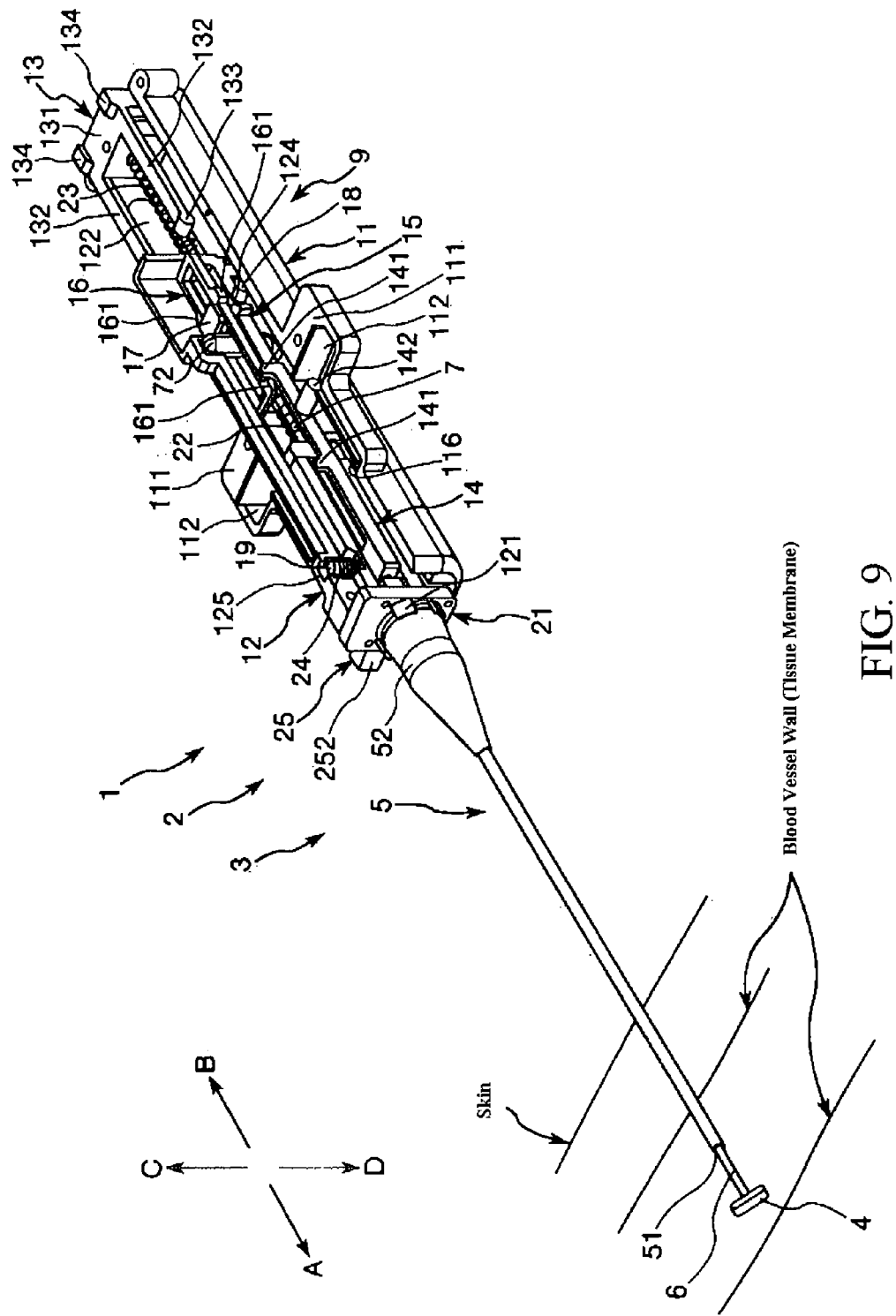
FIG. 9 is a perspective view for illustrating an action (operation) of the tissue closing device shown in FIG. 1
Figure 10:
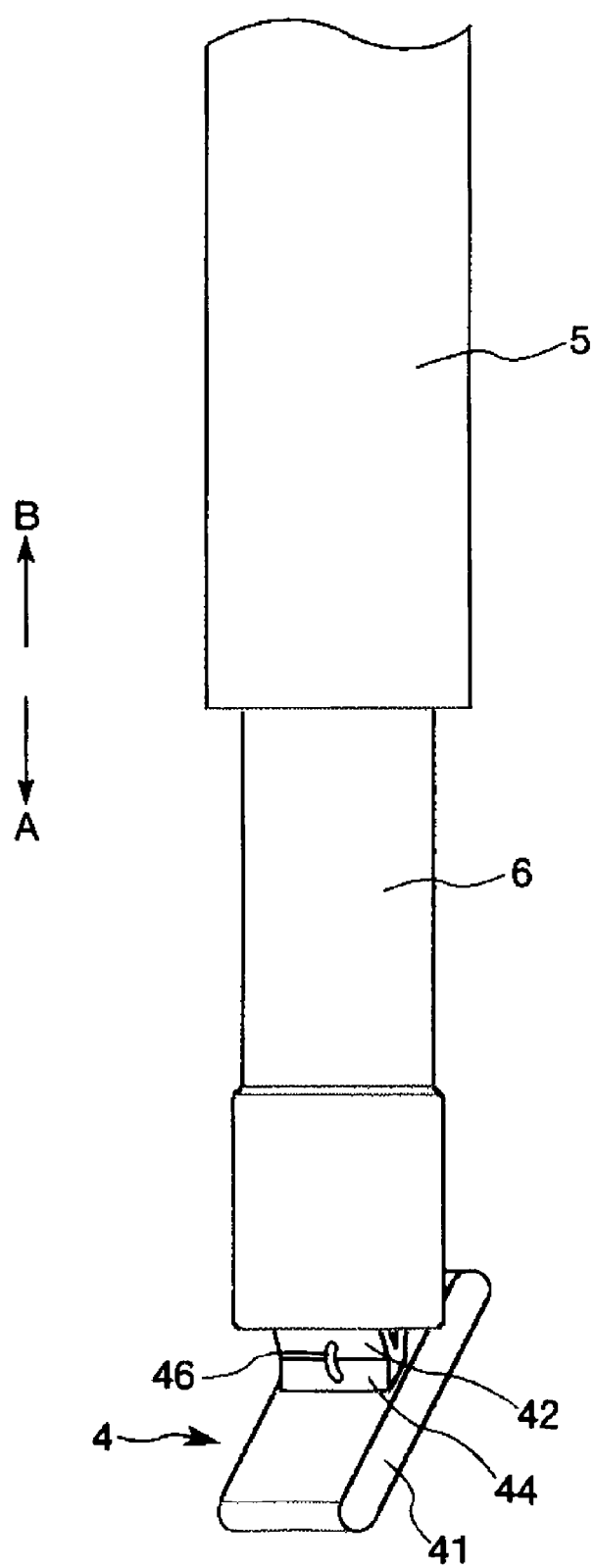
FIG. 10 is a perspective view for illustrating an action (operation) of the tissue closing device shown in FIG. 1
Figure 11:
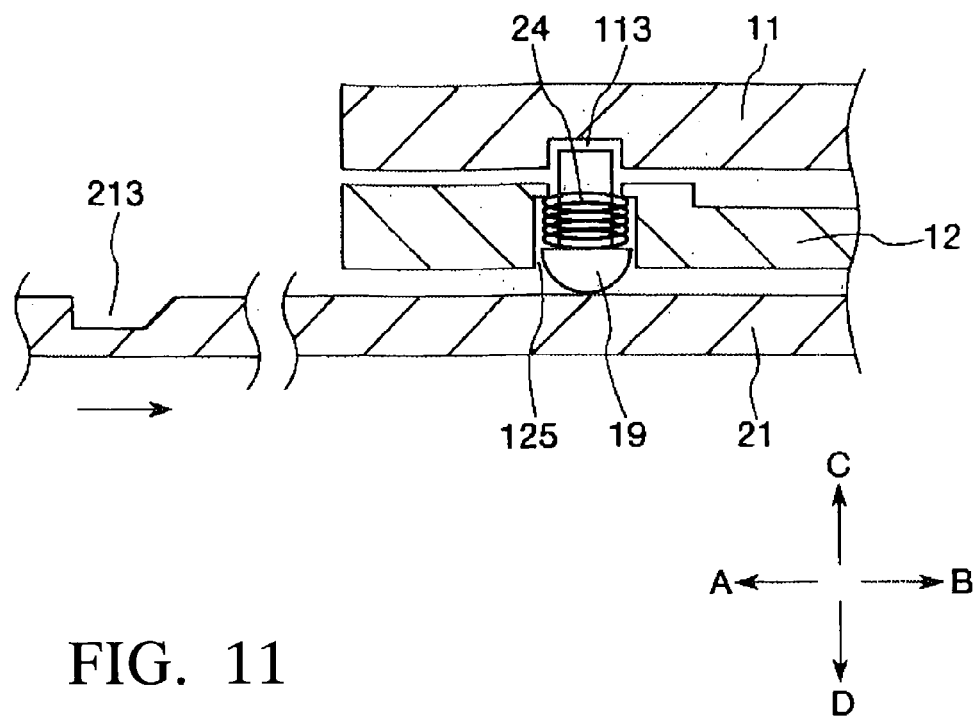
FIG. 11 is a sectional view for illustrating an action (operation) of the tissue closing device shown in FIG. 1
Figure 12:
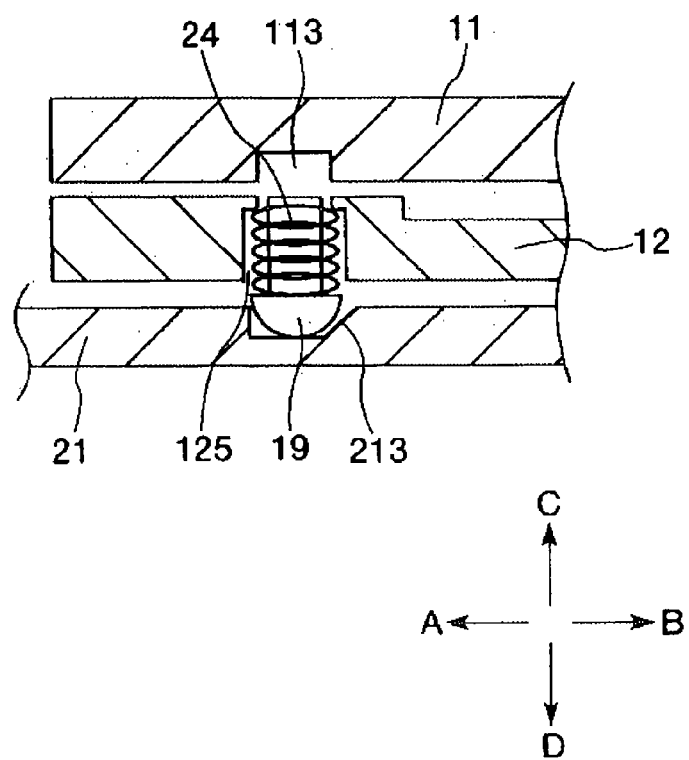
FIG. 12 is a sectional view for illustrating an action (operation) of the tissue closing device shown in FIG. 1
Figure 13:
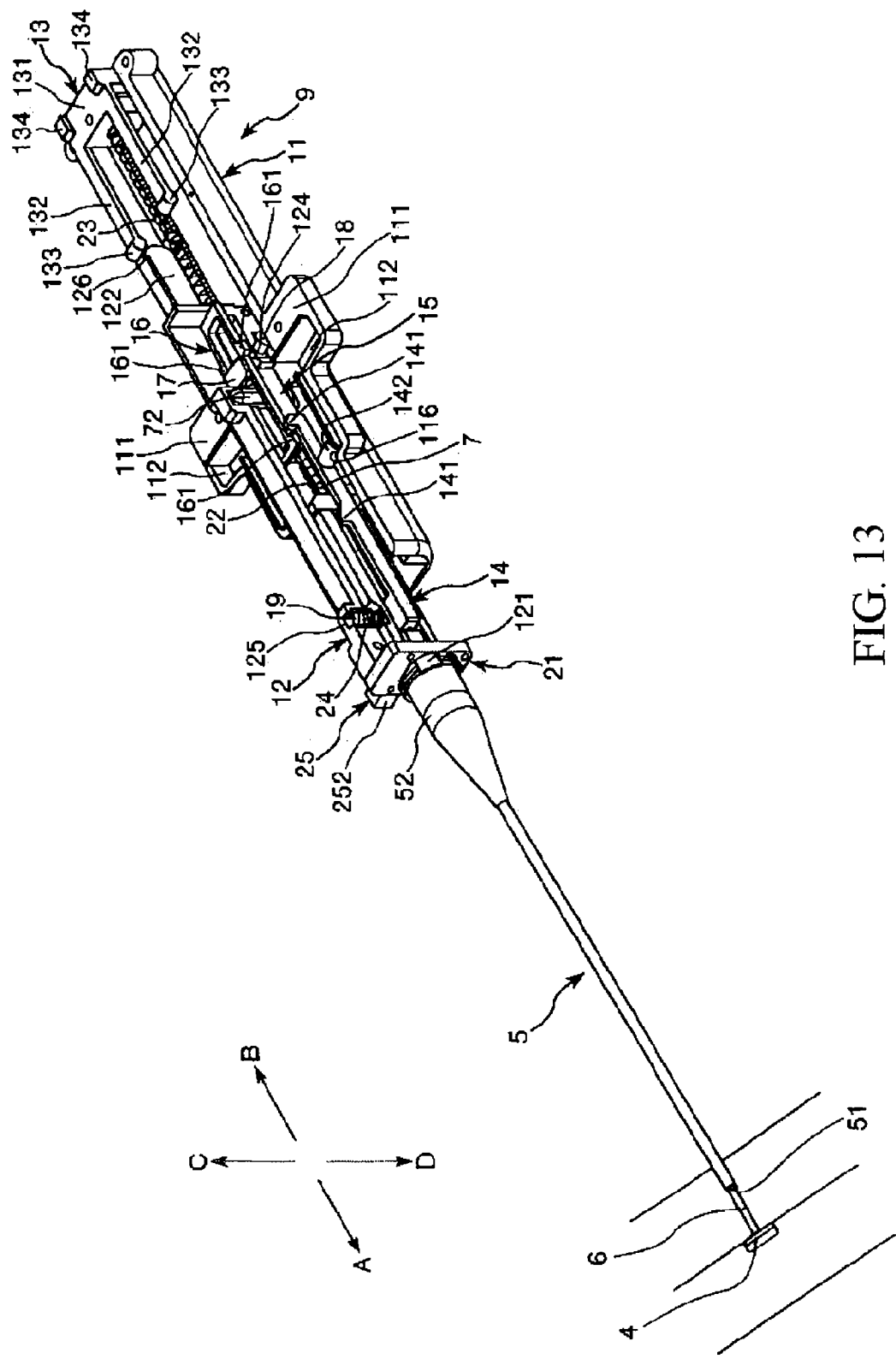
FIG. 13 is a perspective view for illustrating an action (operation) of the tissue closing device shown in FIG. 1
Figure 14:
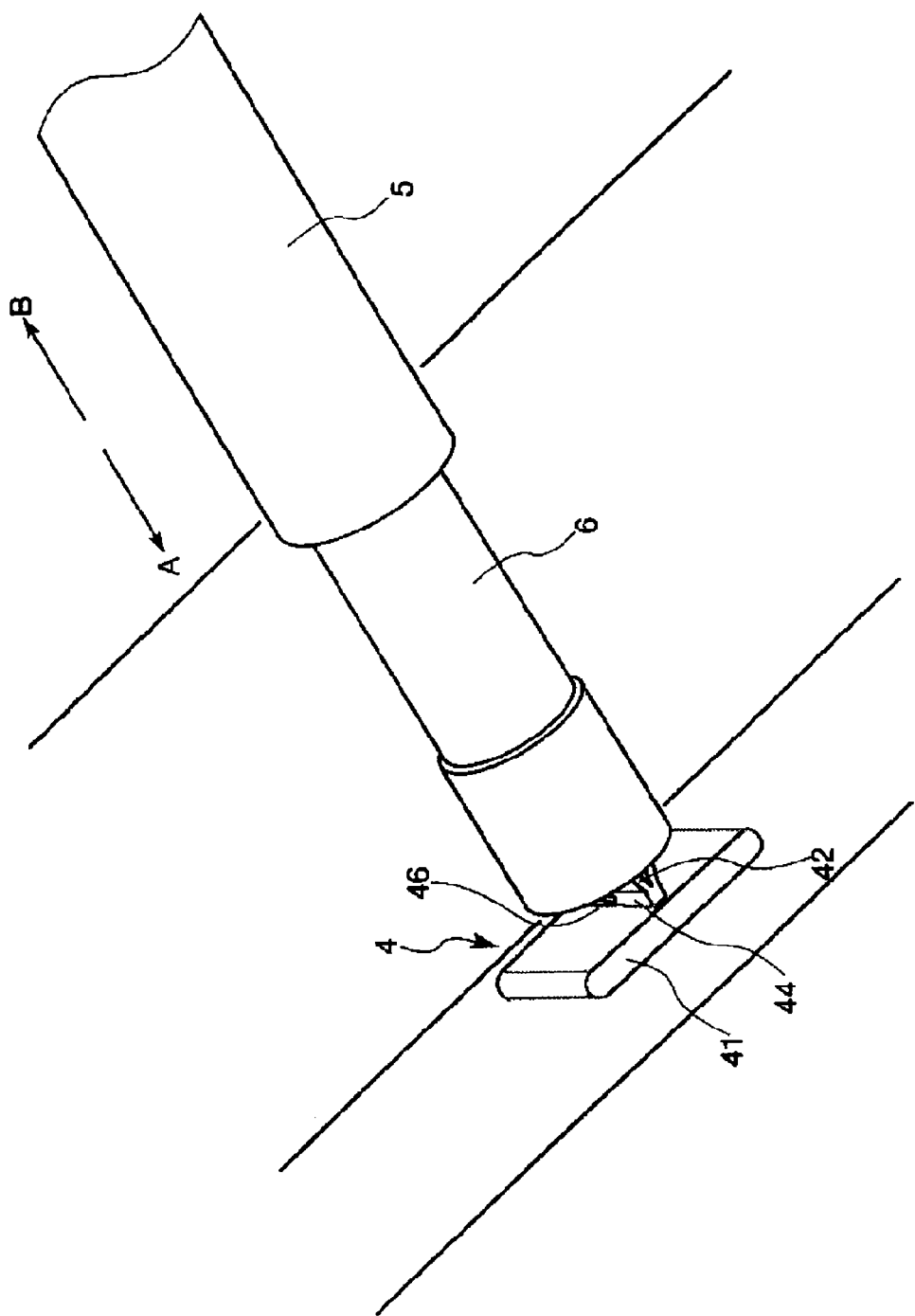
FIG. 14 is a perspective view for illustrating an action (operation) of the tissue closing device shown in FIG. 1
Figure 15:
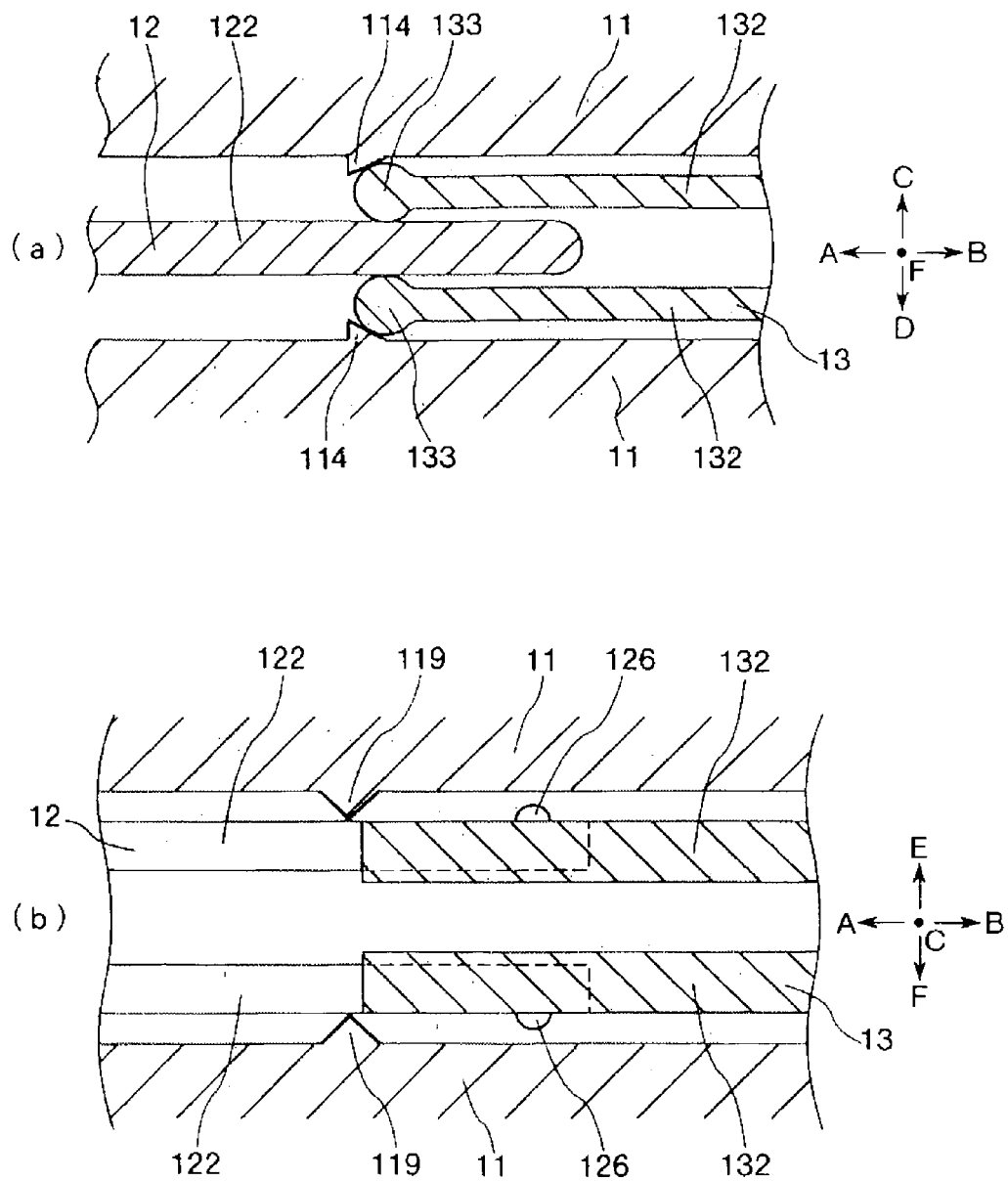
FIGS. 15(a) and 15(b) are sectional views for illustrating an action (operation) of the tissue closing device shown in FIG. 1
Figure 17:
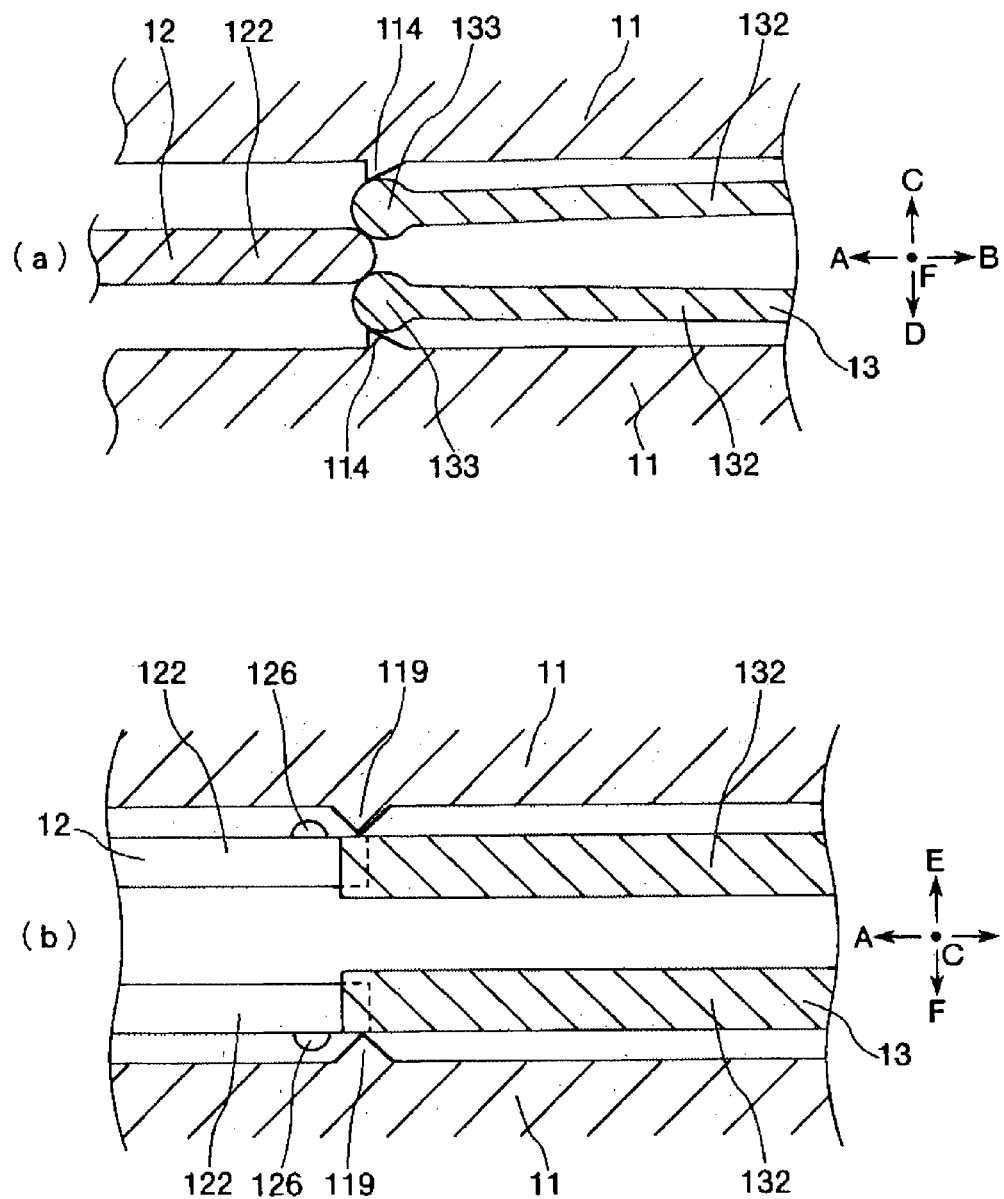
FIGS. 17(a) and 17(b) are sectional views for illustrating an action (operation) of the tissue closing device shown in FIG. 1
Figure 18:
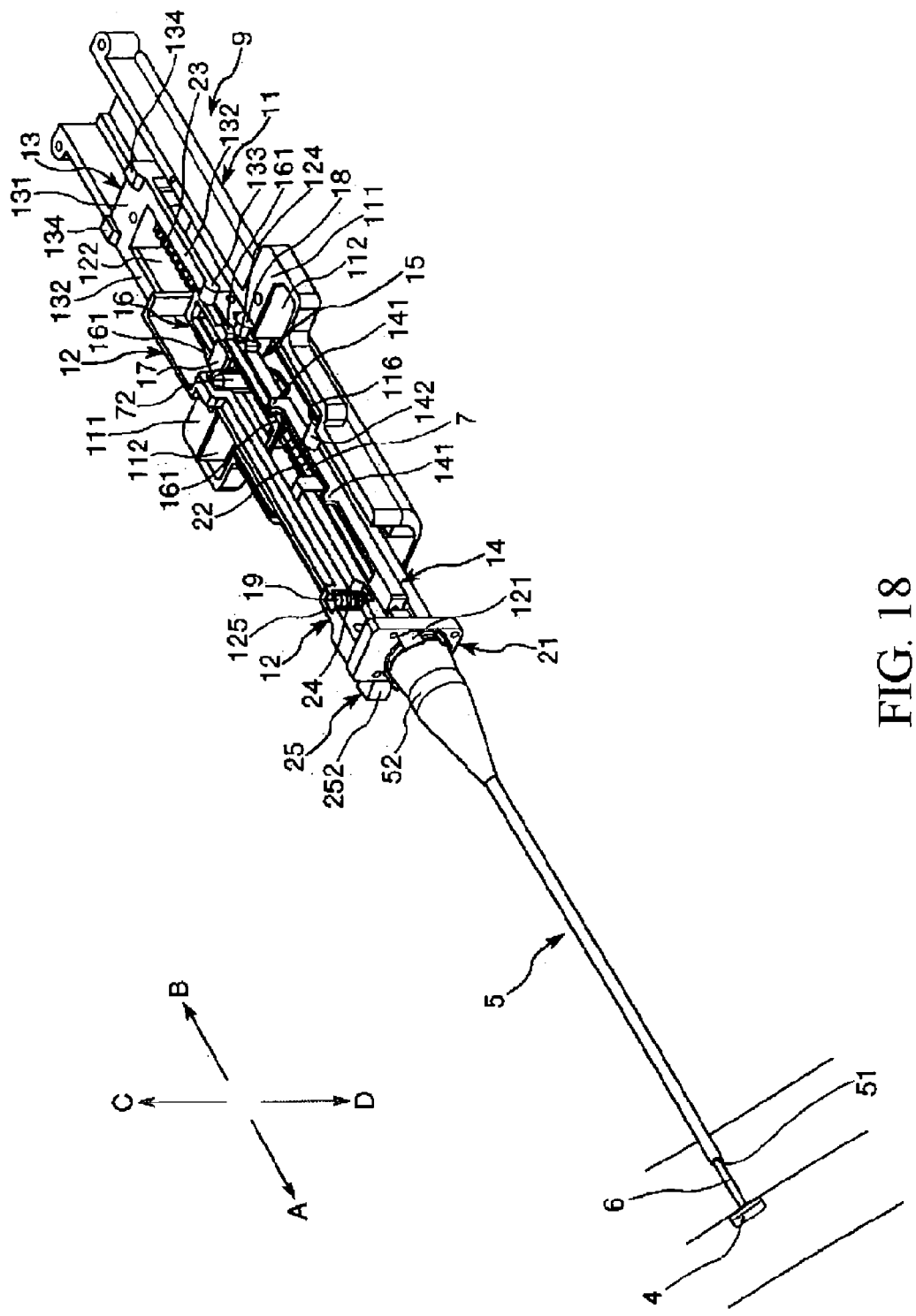
FIG. 18 is a perspective view for illustrating an action (operation) of the tissue closing device shown in FIG. 1

FIG. 1 shows perspective views showing a first embodiment of the tissue closing device, in which FIG. 1(a) A is an overall perspective view, and FIG. 1(b) is a perspective view showing the inner portion side of an upper half of a casing FIG. 2 is a perspective view of a closure in the tissue closing device shown in FIG. 1 FIG. 3 is an illustration of one example of a knot of the closure in the tissue closing device shown in FIG. 1 FIG. 4 is an illustration of another example of the knot of the closure in the tissue closing device shown in FIG. 1 FIG. 5 is an exploded perspective view (members (component parts)) of the tissue closing device shown in FIG. 1 FIG. 6 shows perspective views of a distal end portion of the tissue closing device shown in FIG. 1, in which FIG. 6(a) is an outlook view, and FIG. 6(b) as a perspective drawing (showing the condition where a cover tube is removed) FIG. 7 is a perspective view showing a thread support portion, a pin and a thread in the tissue closing device shown in FIG. 1 FIGS. 8 to 10 are perspective views for illustrating respective actions (operations) of the tissue closing device shown in FIG. 1 FIGS. 11 and 12 are sectional views for illustrating respective actions (operations) of the tissue closing device shown in FIG. 1 FIGS. 13 and 14 are perspective views for illustrating respective actions (operations) of the tissue closing device shown in FIG. 1 FIGS. 15 to 17 are sectional views for illustrating respective actions (operations) of the tissue closing device shown in FIG. 1, in which FIGS. 15(a), 16(a) and 17(a) are sectional views on a lateral side, and FIGS. 15(b), 16(b) and 17(b) are sectional views on the upper side FIG. 18 is a perspective view for illustrating an action (operation) of the tissue closing device shown in FIG. 1 FIGS. 19 and 20 are sectional views for illustrating respective actions (operations) of the tissue closing device shown in FIG. 1 FIGS. 21 to 25 are perspective views for illustrating respective actions (operations) of the tissue closing device shown in FIG. 1

Figure 8:
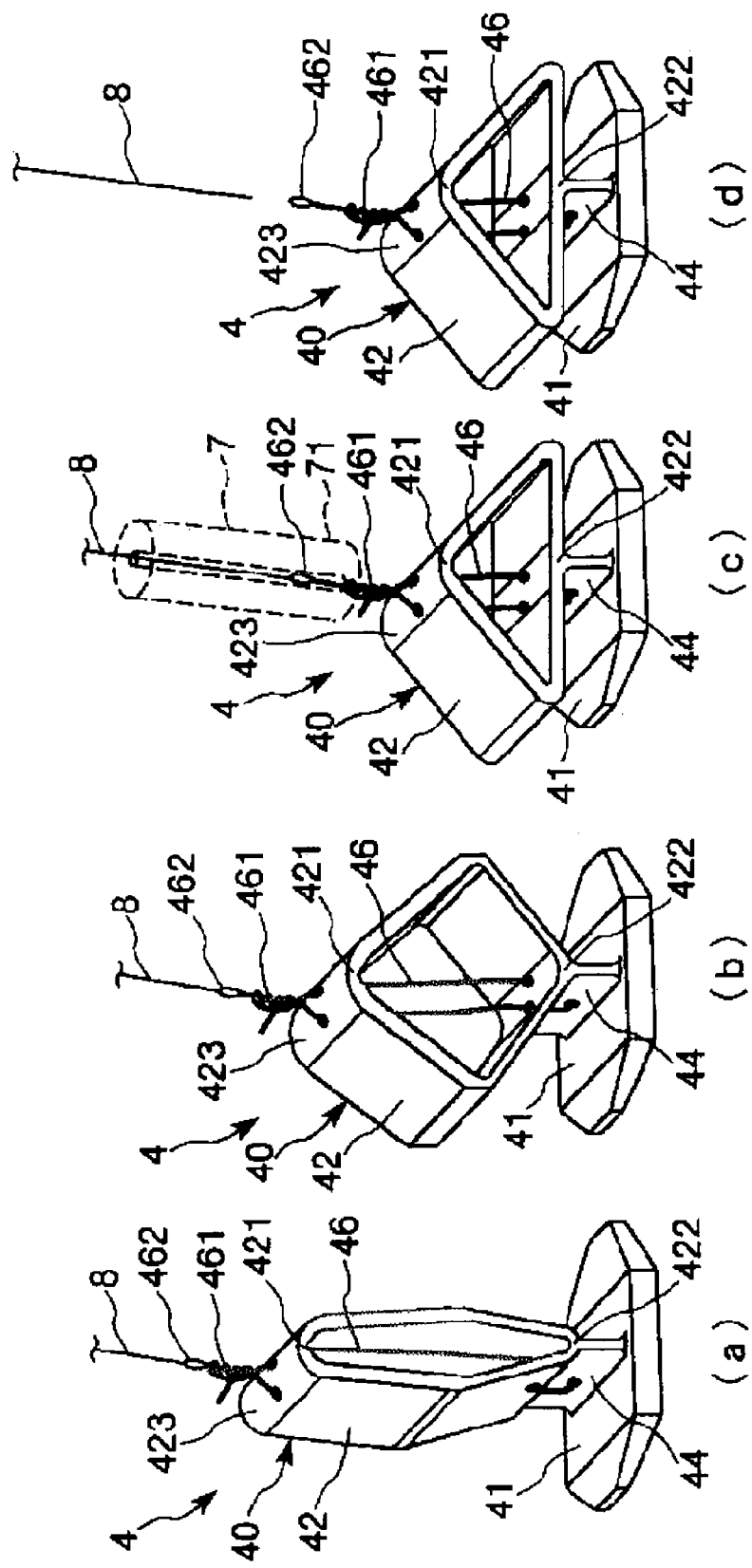
FIG. 8(a)-(d) are perspective views for illustrating an action (operation) of the tissue closing device shown in FIG. 1

Incidentally, in FIGS. 1 and 5, a casing is bisected in the vertical direction, and about one half on a lateral side of a fixed tube support member is omitted In addition, in FIG. 1, the inside of a cover tube and the inside of the fixed tube in the region surrounded by a broken-line circle are enlargedly shown Besides, in FIGS. 9, 13, 18, 21, 23 and 24, the upper half in the vertical direction of the casing is omitted, and about one half on a lateral side of the fixed tube support member is omitted In addition, in FIG. 7, an overall view of a thread is schematically shown Besides, in FIG. 8, a fixed tube 7 is schematically shown in broken lines For convenience of description, in FIG. 1(a), FIGS. 5 to 7, and FIGS. 9 to 25, the direction of arrow A will be referred to as "distal", the direction of arrow B (hand-operated side) as "proximal", the direction of arrow C as "upper", and the direction of arrow D as "lower", in the description Also, in FIGS. 2 to 4, and FIG. 8, the upper side will be referred to as "proximal", and the lower side as "distal", in the description The tissue closing device 1 shown in the figures is a device for closing (closing up) a percutaneously penetrating opening (i e wound hole which penetrates a living tissue membrane) which is formed, for example, in a living organism lumen such as a blood vessel, an internal organ of a living organism or an in vivo tissue membrane such as an internal tissue of a living organism As shown in FIGS. 1, 2 and 5, the tissue closing device 1 includes an elongate arrangement device (feeding and deforming means) 3 which has a distal end portion capable of penetrating a wound hole penetrating an in vivo tissue membrane and has a handling portion 9 on the proximal side, and a clip 4 serving as a closure (tissue closure) which is detachably retained at (connected to) a distal end portion of the arrangement device 3 and which closes the wound hole penetrating the in vivo tissue membrane The clip 4 has a clip body (closure body) 40, and a thread (first thread-like member) 46 serving as a fastener, and the clip body 40 is composed of a seal portion 41, a deformable deformation portion 42, and a connecting portion 44 for connecting the seal portion 41 and the deformation portion 42 to each other In addition, the thread 46 has a knot 461 and a loop 462 Incidentally, the clip 4 will be described in detail later The arrangement device 3 is used in the state of being inserted in a sheath (elongate tube member) 5 which has a distal end portion penetrating a wound hole and which is provided in its central portion with a through-lumen 51 penetrating it in the axial direction, namely, in the state of being detachably mounted in the sheath 5 (see FIG. 9) The sheath 5 and the arrangement device 3 constitute the elongate body portion 2 At the time of a stanching work (a work for closing a wound hole), the distal end portions of the sheath 5 and the arrangement device 3 and the clip 4 penetrate the wound hol In other words, these are inserted into a lumen of a living organism (living orgasm lumen) such as a blood vessel via the wound hole The sheath 5 has a roughly hollow cylindrical shape, and has a hub 52 at its proximal end portion In addition, a stanching valve (not shown) is disposed on an inner circumferential side of the hub 52

As the sheath 5, for example, a sheath (introducer sheath) left indwelling after the procedure of therapy (e g PCI, Percutaneous Coronary Intervention) or diagnosis (e g CAG, Coronary AngioGraphy) using a catheter may be used, or may be a sheath for exclusive use in the tissue closing device Incidentally, while the sheath 5 is included in the components of the body portion 2 in this embodiment, the sheath 5 may be out of the components of the body portion 2

As shown in FIGS. 1, 2 and 5, the arrangement device 3 includes a thread (second thread-like member) 8 which is a retaining member (retaining means) connected to the clip 4 (the thread 46 of the clip 4) and retaining the clip 4 (the thread 46 of the clip 4), a cover tube (cover member) (cover means) 6 which is an elongate first tubular member (tubular member) having a distal end portion capable of penetrating a wound hole, a fixed tube (lock member) (lock means) 7 which is an elongate second tubular member (tubular member) having a distal end portion capable of penetrating a wound hole, and a handling portion 9 The clip 4 (the thread 46 of the clip 4) is detachably retained at a distal end portion of the arrangement device 3 by the thread 8 In this case, the thread 8 retains the clip 4 in such a manner that a portion of the deformation portion 42 of the clip 4 which is on the opposite side (distal side) of the seal portion 41 can be moved (displaced) relative to the portion of the deformation portion 42 which is on the seal portion 41 side (base portion side) (proximal side)

In addition, the fixed tube 7 is disposed (inserted) concentrically in (inside) the lumen of the cover tube 6, and the cover tube 6 can be moved (slided) relative to the fixed tube 7 in the axial direction of them Besides, the thread 8 is disposed (inserted) in (inside) the lumen of the fixed tube 7 so as to be movable relative to the fixed tube 7 in the longitudinal direction of the fixed tube 7 In addition, the handling portion 9 is provided on the proximal side of the fixed tube 7 and the cover tube 6

Here, a proximal end portion of the cover tube 6 is fixed to (supported on) a distal end portion of a cover tube support portion (cover member support tube) 14 of the handling portion 9 As shown in FIG. 6, the deformation portion 42 of the clip 4 is detachably mounted (inserted) in a distal end portion of the cover tube 6 In this case, the deformation portion 42 of the clip 4 is inserted and retained in the lumen of the distal end portion of the cover tube 6, whereby the clip 4 is mounted while maintaining the elongated form (i e folded form) of the deformation portion 42 in the longitudinal direction of the cover tube 6

In addition, when the arrangement device 3 (cover tube 6) is inserted into the through-lumen 51 of the sheath 5 from the proximal side of the sheath 5 and mounted in the sheath 5, the distal end portion of the cover tube 6 is exposed from the distal end of the sheath 5 (the distal end of the sheath is located on the proximal side relative to the distal end of the cover tube 6)

By the cover tube 6 is covered an outer surface of the fixed tube 7, and at a distal end portion thereof, at least a part of the clip 4 (i e the deformation portion 42 in the first embodiment) is covered The fixed tube 7 is formed of a comparatively hard constituent material, and has a hub 72 at its proximal end portion The hub 72 is located in the inside (in a frame) of a thread support portion 15 and a lifter 16, which will be described later, of the handling portion 9, and is fixed to (supported on) a fixed tube support portion (block member support portion) 12 which will be described later In addition, when the arrangement device 3 (fixed tube 7) is inserted into the through-lumen 51 of the sheath 5 from the proximal side of the sheath 5 and mounted in the sheath 5, the distal end of the sheath 5 is located on the proximal side relative to the distal end of the fixed tube 7, and, as shown in FIG. 6, the distal end of the fixed tube 7 is located on the proximal side relative to the distal end of the cover tube 6

The fixed tube 7 has a function such that when the thread 46 of the clip 4 is pulled in the proximal direction by the thread 8, a knot 461 of the thread 46 of the clip 71 is locked to a distal end portion 71 of the fixed tube 7, further the deformation portion is locked (indirectly locked) through the knot 461, whereby the knot 461 is moved relatively to the distal direction, to tighten the thread 46 and deform the deformation portion 42

As shown in FIGS. 1 and 5, the handling portion 9 includes a casing (body) 11, the fixed tube support portion (lock member support portion) 12 for supporting the fixed tube 7, a spring holder (second elastic member support portion) 13, the cover tube support portion (cover member support portion) 14 for supporting the cover tube 6, the thread support portion (retaining member support portion) 15 for supporting the thread 8, a pin (connector) 17 which is inserted in the thread support portion 15 and detachably connects the thread 8 to the thread support portion 15, the lifter (connector support portion) 16 which is a pin support portion for supporting the pin 17, a pair of pins (restrictor) 18 which are stoppers for locking the thread support portion 15, a pin 19, a charge member (charge means) 21, a coil spring (spring) 22 which is a first elastic member (actuating member), a coil spring (spring) 23 which is a second elastic member, and a coil spring (spring) 24

Incidentally, while the casing is bisected in the vertical direction in FIGS. 1 and 5, these are joined to each other in practice The casing 11 has a tubular (polygonal tubular) shape which is roughly rectangular parallelopiped in outlook shape A pair of projected portions 111 projecting sideways and functioning as finger hook portions at the time of operation are formed at side portions in the vicinity of a central portion of the casing 11 In addition, each of the projected portions 111 is provided with a bottomed hole portion 112 communicated with the inside of the casing 11

Besides, an upper portion of the distal end portion of the casing 11 is provided with a bottomed hole portion 113 into which the pin 19 is to be inserted In addition, four projections 114 are provided at a proximal end portion of the inside of the casing 11, and a pair of projections 119 are provided on lateral sides of the upper side, in FIG. 1(b), of a pair of the projections 114 Besides, a pair of stepped portions (engaging portions) 116 are provided on the distal side of a pair of projections 111 in the inside of the casing 11

In the inside of the casing 11, the fixed tube support portion 12 and the spring holder 13 are disposed to be individually movable in the longitudinal direction of the arrangement device 3

The fixed tube support portion 12 is in the shape of a box roughly rectangular parallelopiped in outlook shape The fixed tube support portion 12 is provided at its distal end portion with a connector 121 to be fitted to the hub 52 of the sheath 5 The connector 121 has four pawls capable of engagement with the hub 52, and is located on the distal side of a distal end portion of the casing 11.

In addition, the fixed tube support portion 12 is provided at its proximal end portion with a pair of projected portions 122 projected in the proximal direction Projections 126 are provided respectively at upper portions of proximal end portions of the projected portions 122

Besides, at side portions near a central portion of the fixed tube support portion 12, a pair of slots 123 is formed along the longitudinal direction of the arrangement device 3

In addition, a pair of holes portions 124 into which a pair of pins 18 are to be inserted are provided at side portions of a proximal end portion, namely, at side portions on the proximal side relative to the slots 123, of the fixed tube support portion 12

The projected portion 122, the slot 123 and the hole portion 124 are arranged roughly on the same straight line Besides, a hole portion 125 into which the pin 19 is to be inserted is provided at an upper portion of a distal end portion of the fixed tube support portion 12

In addition, the fixed tube support portion 12 is provided with a no-flush chamber 25 at its distal end portion The no-flush chamber 25 is composed of a tubular blood inflow port 251, and a blood outflow port 252 having a lumen 254 communicated with a lumen 253 of the blood inflow port 251. The blood inflow port 251 is projected in the direction of the distal end of the fixed tube support portion 12, and is projected in the distal direction from a distal end portion of the casing 11 Besides, the blood outflow port 252 is projected toward a lateral side of the fixed tube support portion 12

In addition, the lumen 254 of the blood outflow port 252 is opened to the proximal end of an end portion on a lateral side of the blood outflow port 252 Namely, an opening 255 communicated with the lumen 254 is provided at the proximal end of the end portion on the lateral side of the blood outflow port 252 The opening 255 is being closed by the abutment of an end face 115 of the distal end portion of the casing 11 on the proximal end of the end portion on the lateral side of the blood outflow port 252, but, when the casing 11 is moved in the proximal direction relative to the fixed tube support portion 12, the end face 115 is spaced and the opening 255 is opened The above-described cover tube 6 and fixed tube 7 are passed through the lumen 254 of the blood outflow port 252

The spring holder 13 is located on the proximal side of the fixed tube support portion 12, specifically, at a proximal end portion in the casing 11

The spring holder 13 has four projected portions 132 projected in the distal direction from four corners of a proximal end portion 131 The projected portions 132 are respectively provided with projections 133 which have curved convex surfaces and which can be engaged with the projections 114 of the casing 11 In addition, the proximal end portion 131 is provided, at positions corresponding to the projected portions 132, with projections 134 which can be engaged with the projections 114 of the casing 11

As shown in FIGS. 1 and 13, the spring holder 13 is so disposed that the projected portions 122 of the fixed tube support portion 12 are each clamped between an upper-lower pair of the projected portions 132, and the projections 133 of the projected portions 132 are engaged with the projections 114 of the casing 11 This inhibits the spring holder 13 from moving in the distal direction relative to the casing 11

In addition, as shown in FIGS. 1 and 5, a proximal end portion of the coil spring 23 is fixed to the proximal end portion 131 of the spring holder 13, and a distal end portion of the coil spring 23 is fixed to a proximal end portion of the fixed tube support portion 12 The coil spring 23 is disposed in the state of being somewhat elongated from the natural state The cover tube support portion 14, the thread support portion 15, the lifter 16 and the charge member 21 are disposed in the inside of the fixed tube support portion 12 so that they are respectively movable in the longitudinal direction of the arrangement device 3

As shown in FIG. 7, the thread support portion 15 has a frame-like shape, and is provided in its distal end portion with a hole portion 151 through which the fixed tube 7 is to be passed In addition, the thread support portion 15 is provided in its proximal end portion with a hole portion 152 into which the pin 17 is to be inserted, and a hole portion 153 which is located at a position corresponding to the hole portion 152 and through which the thread 8 can be threaded Besides, curved convex surfaces are formed at both side portions of the proximal end portion of the thread support portion 15 Incidentally, inclined surfaces, for example, may be provided in place of the curved convex surfaces The thread 8 is composed of a double thread (double thread-like member) in which a single thread (thread-like member) is bent back and the bent-back portion 81 constitutes one end portion thereof. In addition, the thread 8 is attached to the thread support portion 15 by a method in which the thread 8 in the state of a single, thread is passed through a hole portion 154 formed in the proximal end portion of the thread support portion 15, and then both end portion thereof are tied to each other The thread 8 is passed through the clip 4 (the loop 462 of the thread 46 of the clip 4) and is bent back at a distal end portion of the arrangement device 3, and in the condition where the thread 8 retains the clip 4, the pin 17 is passed through the loop of the bent-back portion 81, and the bent-back portion 81 is detachably connected to the thread support portion 15 by the pin 17 As has been described above, the other end portion (an end portion on the opposite side of the bent-back portion 81) is attached to the thread support portion 15

Incidentally, at the time of passing the pin 17 through the loop of the bent-back portion 81 of the thread 8, the bent-back portion 81 is drawn out from the hole portion 153 to the exterior, and the pin 17 is inserted into the hole portion 152

In addition, as shown in FIGS. 1 and 19, a pair of pins 18 are passed through a pair of hole portions 124 in the fixed tube support portion 12, and the thread support portion 15 is locked by tip end portions of the pins 18 Besides, a head portion of each of the pins 18 abuts on the inside surface of the casing 11 so that the pin 18 would not come off (move from) the hole portion 124 This inhibits the thread support portion 15 from moving to the proximal direction relative to the fixed tube support portion 12

As shown in FIGS. 1 and 5, the cover tube support portion 14 is located on the distal side of the thread support portion 15 and on the proximal side of the no-flush chamber 25 The lifter 16 is mounted on the upper side of the cover tube support portion 14 and the thread support portion 15, and is disposed to be movable (displaceable) upward The lifter 16 has a frame-like shape, and is so situated that the hole portion 152 in which to insert the pin 17 is located in the inside of the frame, in plan view This ensures that when the pin 17 is inserted in the hole portion 152, the pin 17 is supported by the lifter 16

In addition, the lifter 16 is provided with four projections (first projections) 161 Each of the projections 161 projects sideways from a side portion of the lifter 16

On the other hand, the cover tube support portion 14 is provided with four projections (second projections) 141 which are displacement portions for moving (displacing) the lifter 16 upward by abutting on the corresponding projections 161 Each of the projections 141 projects upward from an upper portion of the cover tube support portion 14

Besides, a pair of projected portions (engaging portions) 142 projected sideways are provided at side portions of a proximal end portion of the cover tube support portion 14 Each of the projected portions 142 is able to pass through the slot 123 in the fixed tube support portion 12, to project to the outside of the fixed tube support portion 12, and to be engaged with the stepped portion 116 of the casing 11

The charge member 21 has a frame-like shape, and is disposed at a distal end portion of the fixed tube support portion 12 so that a distal end portion of the cover tube support portion 14 and the no-flush chamber 25 are located in the inside of the frame The charge member 21 is provided at its distal end portion with a hole portion 211 through which to pass the cover tube 6 and the fixed tube 7, and is provided at its proximal end portion with a hole portion 212 through which to pass the fixed tube 7 In addition, the charge member 21 is provided at its upper portion with a recessed portion 213 in which to insert the pin 19

Besides, the coil spring 22 is disposed in its natural state between a proximal end portion of the charge member 21 and a distal end portion of the thread support portion 15, inside the fixed tube support portion 12

In addition, as shown in FIGS. 1 and 11, the pin 19 and the coil spring 24 are inserted (disposed) in the hole portion 125 of the fixed tube support portion 12 The coil spring 24 is disposed in its contracted state, and the pin 19 is biased downward by the restoring force (elastic force) of the coil spring 24 A tip end portion of the pin 19 is inserted in the hole portion 113 of the casing 11, and a head portion of the pin 19 abuts on an upper face of the charge member 21 so that the pin 19 would not come off the hole portion 113 This inhibits the fixed tube support portion 12 from moving relative to the casing 11

Next, the clip 4 will be described

As shown in FIG. 2, the clip (closure) 4 includes a clip body (closure body) 40 and the thread (first thread-like member) 46 which is a fastener The clip body 40 is composed of the seal portion 41, the deformable deformation portion 42, and the connecting portion 44 for connecting the seal portion 41 and the deformation portion 42 to each other Preferably, the seal portion 41, the deformation portion 42 and the connecting portion 44, namely, the clip body 40, is integrally formed of the same material The seal portion 41 is a member having a flat surface portion (flat surface) 412 for covering a wound hole and a peripheral portion of the wound hole by making close contact with the peripheral portion of the wound hole (that portion of an in vivo tissue membrane which includes the wound hole) from one face (inner face) side of the in vivo tissue membrane, and has a plate-like shape Of the seal portion 41, the surface (the surface on the upper side in FIG. 2) to which the deformation portion 42 (described later) is connected is a substantially flat surface The deformation portion 42 has a pantograph-like shape (i e roughly rhombic frame-like body) and is linked (connected) through the connecting portion 44 to a substantially central area of the flat surface portion 412 of the seal portion 41

Specifically, the deformation portion 42 has a frame-like shape capable of being deformed between a first form of being elongated in a direction substantially perpendicular to the seal portion 41 and contracted in a direction substantially parallel to the seal portion 41 and a second form of being contracted in a direction substantially perpendicular to the seal portion 41 and expanded in a direction substantially parallel to the seal portion 41 Therefore, the deformation portion 42 can be deformed from a fundamental form (fundamental shape) shown in FIG. 2 to an arbitrary form between the first form and the second form, for example, a form allowing passage through a wound form, a form enabling closure of a wound hole by clamping an in vivo tissue membrane between the deformation portion 42 and the seal portion 41 from the other face (outer face) side In the case where the in vivo tissue membrane is a blood vessel wall (living organism lumen wall), the one face is a face distal from the body surface (skin), i e, an inner surface of the blood vessel wall (living organism lumen wall), and the other face is a face proximal to the body surface (skin), i e, an outer surface of the blood vessel wall (living organism lumen wall)

Here, in the first embodiment, the deformation portion 42 is a portion having a quadrangular annular shape formed by bending a belt-like member four times (a polygonal annular shape formed by bending a belt-like member a plurality of times) Specifically, the deformation portion 42 has a quadrangular shape (quadrangular frame-like shape) having four links joined integrally to each other and having four corner portions capable of being bent in a hinge-like manner Of the two corner portions 421 and 422 present at the diagonal positions in the vertical direction in FIG. 2, the corner portion 422 on the lower side (seal portion 41 side) in FIG. 2 is connected through the connecting portion 44 to a substantially central area of the flat surface portion 412 of the seal portion 41, and serves as an immovable portion which cannot move relative to an end portion, on the upper side in FIG. 2, of the connecting portion 44

This ensures that the deformation portion 42 can be deformed so that the corner portion 421 and the corner portion 422 come closer to and away from each other, namely, can be elongatingly and contractingly deformed in two directions orthogonal to each other, and can rock pivotally relative to the seal portion 41 in single plane In addition, the corner portion 421 on the upper side (the opposite side of the seal portion 41) in FIG. 2 has an upper surface (the surface on the opposite side of the seal portion 41) 423 in the shape of a curved convex surface The corner portion 421 of the deformation portion 42 is provided near its center with two holes (through-holes) 425 and 428, and the corner portion 422 is provided near its center with two holes (through-holes) 426 and 427

Besides, the connecting portion 44 has a plate-like shape, and is provided with a hole (through-hole) 441 near the center thereof By the connecting portion 44, the seal portion 41 and the corner portion 422 of the deformation portion 42 can be spaced from each other by a predetermined distance The thread 46 is hooked on an end portion side of the deformation portion 42 on the opposite side of the seal portion 41, and on an end portion side of the deformation portion 42 on the side of the seal portion 41, so that the thread 46 is attached to the clip body 40 In the first embodiment, the thread 46 is hooked on the corner portion 421 (the end portion on the opposite side of the seal portion 41) of the deformation portion 42 and the connecting portion 44 in the state of penetrating the corner portion 421 of the deformation portion 42 and the connecting portion 44 Specifically, the thread 46 passes through (penetrates), sequentially from the upper side in FIG. 2, the hole 425 in the corner portion 421 of the deformation portion 42, the hole 426 in the corner portion 422, the hole 441 in the connecting portion 44, the hole 427 in the corner portion 422, and the hole 428 in the corner portion 421, and forms a knot 461 shaped as shown in FIG. 3 or 4 on the side of the corner portion 421 (the outside of the deformation portion 42) Such a knot is called "Clinch knot" In addition, a loop 462 through which to pass the thread 8 is formed on the upper side, in FIG. 2, of the knot 461

The knot 461 is such a knot as to be movable to the distal direction, namely, downward in FIG. 2 With the knot 461 moved on the thread 46 to the distal direction so as to tighten the thread 46, the deformation portion 42 is deformed into a desired form between the first form and the second form, and this condition can be maintained While the thread 46 maintains the condition where the deformation portion 42 is in the desired form, the knot 461 is located at an end portion on the opposite side of the seal portion 41 of the deformation portion 42, i e, at the corner portion 421. Due to the strong tension on the thread 46, the knot 461 would not naturally move to the proximal direction unless a strong force is exerted The knot 461 is formed to be greater than the inside diameter of the fixed tube 7, and the loop 462 is formed to be smaller than the inside diameter of the fixed tube 7 This ensures that at the time of moving the knot 461 of the thread 46 of the clip 4 by the fixed tube 7 and tightening the thread 46 to deform the deformation portion 42, the loop 462 can be led into the lumen of the fixed tube 7, whereas the knot 461 can be prevented from entering into the lumen of the fixed tube 7, and, therefore, the knot 461 can be moved assuredly In this manner, the thread 46 functions as a fastener for the deformation portion 42

As has been described above, the thread 8 is passed through the lumen of the fixed tube 7 in the state of being passed through the loop 462 of the thread 46

Incidentally, the thread 46 and the thread 8 may be the same thread (i e single thread) In this case, it suffices that the deformation portion 42 is fixed by the thread 46, and thereafter the thread 46 is cut on the proximal side relative to the knot 461 by scissors or the like In addition, the thread 46 may be composed of a double thread (double thread-like member) in which a single thread (thread-like member) is bent back and the bent-back portion constitutes one end portion, and the loop 462 may be formed of the bent-back portion Preferably, at least a part of the clip body 40 of the clip 4 is formed of a bioabsorbable material Particularly, a main part (most part) of the clip body 40 is preferably formed wholly integrally of a bioabsorbable material This ensures that the main part of the clip body 40 is absorbed into a living organism after a predetermined period of time, and will not finally be left in the living organism, whereby influences of the clip body 40 on the human body can be precluded In addition, the thread 46 also is preferably formed of a bioabsorbable material Specifically, the entire clip (closure) 4 is preferably formed of the bioabsorbable material(s)

Examples of the bioabsorbable material which can be used include polylactic acid, polyglycolic acid, polydioxanone, etc, used singly, and complexes thereof.

Incidentally, the material constituting the clip body 40 of the clip 4 is not limited to the bioabsorbable material, and may be a biocompatible material such as a resin, a metal, etc In addition, the material constituting the thread 46 is also not limited to the bioabsorbable material Besides, as for the physical properties required of the clip body 40 of the clip 4, particularly required for the deformation function of the deformation portion 42, a material with excellent hinge characteristic is desirable Specifically, a material having a tensile strength of 250 to 500 (Kg/cm$^2$), an elongation of 150 to 800%, a tensile modulus of 8 to 20 ($\times 10^3$ Kg/cm$^2$), and a bending strength of 300 to 700 (Kg/cm$^2$) is preferable By fulfilling these physical property values, the clip body 40 can be excellent in hinge characteristic and can have a desired deformability of the deformation portion 42

As shown in FIG. 8, when the thread 46 of the clip 4 is pulled in the proximal direction by the thread 8 in the condition where the deformation portion 42 of the clip 4 has come off a distal end portion of the cover tube 6 so that the deformation portion 42 can be deformed, the knot 461 of the thread 46 of the clip 4 is locked on the distal end portion 71 of the fixed tube 7, the deformation portion 42 is locked (indirectly locked) through the knot 461, whereby the knot 461 is moved in the distal direction, the thread 46 is tightened, and the deformation portion 42 is deformed In this case, where the clip 4 is mounted to the cover tube 6, the deformation portion 42 of the clip 4 is in the form of being elongated in a direction substantially perpendicular to the seal portion 41 and contracted in a direction substantially parallel to the seal portion 41, as shown in FIG. 8(a) As the knot 461 is moved in the distal direction and the thread 46 is tightened, the corner portion 421 of the deformation portion 42 is gradually moved downward in FIG. 8, and the deformation portion 42 is continuously deformed from the form shown in FIG. 8(a) to the form shown in FIG. 8(b), and then to the form of being capable of closing a wound hole by clamping an in vivo tissue membrane between the seal portion 41 and the deformation portion 42 as shown in FIG. 8(c) Namely, the deformation portion 42 is gradually contracted in the direction substantially perpendicular to the seal portion 41 and gradually expanded in the direction substantially parallel to the seal portion 41

In addition, as has been described above, the knot 461 is such a knot that it can be moved to the distal direction only when a strong force is exerted thereon, the condition where the deformation portion 42 is in a predetermined form is maintained by the thread 46

Thus, by the clip 4, the degree of deformation of the deformation portion 42 can be continuously regulated (adjusted) Specifically, the distance between the two corner portions 421 and 422 can be continuously regulated (adjusted) Namely, the condition where the deformation portion 42 is assuming a desired form can be maintained This makes it possible to cope with various cases such as a person whose in vivo tissue membrane (e g blood vessel wall) is thick, a person whose in vivo tissue membrane is thin, a person whose in vivo tissue membrane is hard, a person whose in vivo tissue membrane is soft, etc (to cope with various conditions (statuses) of in vivo tissue membrane)

Incidentally, in the present invention, the configuration of the clip (closure) is not limited to the above-mentioned, inasmuch as it has a seal portion and a deformation portion For example, in the present invention, the shape of the deformation portion of the clip is not limited to a quadrangle, but may be other polygon or a corner-less frame-like shape such as a circular annular shape, and an elliptic annular shape In addition, the deformation portion of the clip may be composed, for example, a spongy porous body (porous material), an aggregate of fibers, or the like including mainly of a biodegradable material (biodegradable synthetic resin material) such as collagen Besides, the fastener of the clip is not limited to the thread Now, a procedure of a stanching work conducted by use of the tissue closing device 1 and the actions of the tissue closing device 1 will be described below As shown in FIG. 9, after a procedure for therapeutic treatment (PCI) or diagnosis (CAG) using catheters, the sheath 5 is left indwellng, and the sheath 5 is used for the stanching work A distal end portion of the sheath 5 is penetrating a wound hole and inserted in a blood vessel First, the operator gradually insert the arrangement device 3 into the through-lumen 51 of the sheath 5 from the proximal side of the sheath 5, and fit the connector 121 of the arrangement device 3 and the hub 52 of the sheath 5 to each other This results in that, as shown in FIG. 10, a distal end portion of the cover tube 6 protrudes from a distal end portion of the sheath 5, and the seal portion 41 of the clip 4 protrudes, to be inserted in the blood vessel In addition, the blood inflow port 251 of the no-flush chamber 25 is inserted into the inside of the sheath 5 via the stanching valve of the hub 52 of the sheath 5, and the lumen 253 of the blood inflow port 251 and the through-lumen 51 of the sheath 5 are communicated with each other In addition, at the time of fitting the connector 121 of the arrangement device 3 and the hub 52 of the sheath 5 to each other, the hub 52 of the sheath 5 is pressed against a distal end portion of the charge member 21 of the arrangement device 3, and the charge member 21 is pushed in the proximal direction By this, as shown in FIG. 11, the charge member 21 is moved in the proximal direction, and the coil spring 22 is gradually contracted (deformed, activated, charged) while being clamped between the charge member 21 and the thread support portion 15

Then, as shown FIG. 12, when the charge member 21 is moved until the recessed portion 213 of the charge member 21 is located on the lower side of the pin 19, the pin 19 is moved downward by the restoring force (elastic force) of the coil spring 24 In other words, the pin 19 comes off the hole portion 113 of the casing 11, and is inserted into the recessed portion 213 of the charge member 21.

As a result of this, the casing 11 is movable relative to the fixed tube support portion 12 In addition, the charge member 21 is immovable relative to the fixed tube support portion 12 Specifically, the positional relationship between the charge member 21 and the fixed tube support portion 12 is fixed On the other hand, the thread support portion 15 is locked by the pair of pins 18 from moving to the proximal direction relative to the fixed tube support portion 12, whereby the coil spring 22 is maintained in the contracted state (deformed state, active state) Specifically, the pair of pins 18 lock the thread support portion 15 to thereby inhibit the thread support portion 15 and the fixed tube support portion 12 from moving relative to each other (i e inhibit the clip 4 and the fixed tube 7 from moving relative to each other), whereby the coil spring 22 is maintained in the deformed state (active state) In addition, the thread support portion 15 is biased (pushed) in the proximal direction by the restoring force of the coil spring 24, so that the positional relationship between the thread support portion 15 and the fixed tube support portion 12 is fixed This condition is the to be a condition where the fixed tube support portion 12 and the thread support portion 15, which are internal structures, are disposed in the first positions inside the casing 11.

Next, the casing 11 of the handling portion 9 is gripped by fingers of a hand, and the handling portion 9, i e, the body portion 2 (arrangement device 3) is slowly moved in one direction, i e, in a direction for drawing out of the wound hole (proximal direction), whereby the body portion 2 is drawn out of the wound hole By this, all operations (motions) are carried out sequentially and continuously, whereby the wound hole is closed with the clip 4, and the clip 4 is disposed (to indwell) in the living organism Now, the procedure and actions in this case will be described in detail below First, as shown in FIGS. 13 and 14, the casing 11 of the handling portion 9 is gripped by fingers of a hand, and the handling portion 9 (casing 11) is moved in the proximal direction, when the wound hole and a peripheral portion of the wound hole are covered with the seal portion 41 of the clip 4 from the inside of the blood vessel wall (the seal portion 41 is positioned), and the deformation portion 42 of the clip 4 is moved to the outside of the blood vessel Then, as mentioned above, the casing 11 is movable relative to the fixed tube support portion 12, whereas the spring holder 13 is inhibited from moving to the distal direction relative to the casing 11. Therefore, when the handling portion 9 (casing 11) is moved to the proximal direction in the condition where the seal portion 41 of the clip 4 is in contact with the inside surface of the blood vessel wall (the surface distal from the body skin surface), the casing 11 is moved to the proximal direction relative to the fixed tube support portion 12, the coil spring 23 is expanded, and the fixed tube support portion 12 is biased in the proximal direction by the restoring force (elastic force) of the coil spring 23 In this case, since the positional relationship between the fixed tube support portion 12 and the thread support portion 15 is fixed, the thread support portion 15 is biased in the proximal direction (biased in the proximal direction via the fixed tube support portion 12) by the restoring force of the coil spring 23, whereby the clip 4 is biased (pulled) in the proximal direction via the thread 8 By this, the seal portion 41 can be assuredly brought into contact with the wound hole and the surrounding tissues Besides, even when the clip 4 is somewhat caught inside the blood vessel before assured contact of the seal portion 41 with the wound hole and the surrounding tissues, it can be expected that the clip 4 comes off before the restoring force of the coil spring 23 exceeds a predetermined value, so that the clip 4 can be moved to the wound hole to thereby bring the seal portion 41 into contact with the wound hole and the surrounding tissues Here, when the casing 11 is moved to the proximal direction relative to the fixed tube support portion 12 as abovementioned, the projected portion 122 of the fixed tube support portion 12 having been located between the projections 133 of the upper-lower pair of projected portions 132 of the spring holder 13 is moved to the distal direction relative to the spring holder 13 and the casing 11, as shown in FIG. 15, and is released from the projections 133 of the pair of projected portions 132 (in this instance, the projections 126 of the projected portion 122 ride over the projections 119), as shown in FIGS. 13 and 17 Immediately before the projected portion 122 is released from the projections 133 of the pair of projected portions 132, the biasing force of the coil spring 23 reaches a predetermined value (allowable maximum value) Then, when the projected portion 122 is released from the projections 133 of the pair of projected portions 132, the pair of projected portions 132 are capable of being deformed (deflexed) toward each other, the biasing force of the coil spring 23 causes the projections 114 of the projected portions 132 to ride over the projections 114 of the casing 11, and the spring holder 13 is moved to the distal direction relative to the casing 11, as shown in FIG. 18 As a result, the biasing force of the coil spring 23 is reduced or lost On the other hand, the projections 134 of the spring holder 13 are engaged with the projections 114 of the casing 11, whereby the spring holder 13 is inhibited from moving in the distal direction relative to the casing 11

By this, a tension exerted on the blood vessel wall having been pulled to the proximal side by the biasing force of the coil spring 23 through the clip 4 is lowered, resulting in a condition suitable for closing the wound hole with the clip 4 This condition is the to be a condition where the fixed tube support portion 12 and the thread support portion 15, which are internal structures, are disposed in the second positions inside the casing 11

After the spring holder 13 is moved to the distal direction relative to the casing 11, it is possible to cancel the restriction for maintaining the coil spring 22 in the contracted state (deformed state, active state) In other words, the canceling of the restriction for maintaining the coil spring 22 in the contracted state becomes possible on the condition that the moving amount of the casing 11 relative to the fixed tube support portion 12 (the extending amount of the coil spring 23), i e, the biasing force of the coil spring 23 have exceeded a predetermined threshold (predetermined value) In addition, when the biasing force of the coil spring 23 has exceeded the predetermined threshold, the spring holder 13 is moved in the distal direction as above-mentioned, whereby the biasing force is reduced or lost Besides, when the projection 126 of the projected portion 122 of the fixed tube support portion 12 is located at the position for contact with the projection 119 (see FIG. 1(b)) formed on the inside surface of an upper portion of the casing 11, as shown in FIG. 16, due to the friction (frictional resistance) between the portions in contact the force required for moving the handling portion 9 (casing 11) to the proximal direction (pulling resistance) is abruptly increased to the maximum This permits the operator to recognize that the projected portion 122 is just going to be released from the projections 133 of the pair of projected portions 132

In addition, the operator confirms in this instance that blood is not flowing out from the blood outflow port 252 of the no-flush chamber 25, whereby he/she can judge that the seal portion 41 is in abutment on (in surface contact with) the wound hole and the surrounding tissues and that the positioning of the seal portion 41 has been completed.

The reason is as follows Since the casing 11 has been moved to the proximal direction relative to the fixed tube support portion 12, the opening 255 of the blood outflow port 252 is spaced from the end face 115 of the casing 11 and is opened For example, when the clip 4 is caught (stuck) inside the blood vessel, the distal end of the sheath 5 is located inside the blood vessel, so that the blood flows in via the distal end of the sheath 5, flows through a conduit defined (formed) by the inner circumferential surface of the sheath 5 and the outer circumferential surface of the cover tube 6, flows through the lumen 253 of the blood inflow port 251 of the no-flush chamber 25 and the lumen 254 of the blood outflow port 252, and flows out via the opening 255 When the seal portion 41 is in contact with the wound hole and the surrounding tissues, the distal end of the sheath 5 is located outside the blood vessel, so that the blood would not flow out from the blood outflow port 252

Then, when the handling portion 9 (casing 11) is moved further to the proximal direction under the condition where the seal portion 41 of the clip 4 is in contact with the inside surface of the blood vessel wall, the casing 11 is moved to the proximal direction relative to the fixed tube support portion 12, the coil spring 23 is again extended, so that the clip 4 is biased in the proximal direction by the restoring force of the coil spring 23 through the thread 8, in the same manner as above As a result, the clip 4 is in a state of being more suitable for closing the wound hole In addition, the casing 11 is moved to the proximal direction relative to the fixed tube support portion 12, the pair of stepped portions 116 of the casing 11 and the pair of projected portions 142 of the cover tube support portion 14 are engaged with each other, and the cover tube support portion 14 is moved to the proximal direction relative to the fixed tube support portion 12 together with the casing 11 By this, the cover tube 6 is moved to the proximal direction relative to the deformation portion 42 of the clip 4 together with the cover tube support portion 14, and the deformation portion 42 is released from a distal end portion of the cover tube 6, resulting in that the deformation portion 42 can be deformed Incidentally, the operation of releasing of the deformation portion 42 from the distal end portion of the cover tube 6 and the operation of moving of the spring holder 13 to the distal direction relative to the casing 11 may be performed in a reverse order on a time basis, or may be performed simultaneously When the handling portion 9 (casing 11) is moved further to the proximal direction in the condition where the seal portion 41 of the clip 4 is in contact with the inside surface of the blood vessel wall, the casing 11 is moved further to the proximal direction relative to the fixed tube support portion 12

Then, when the casing 11 is moved to the proximal direction relative to the fixed tube support portion 12 to a predetermined position, i e, until the pair of pins 18 are located at the pair of hole portions 112 of the casing 11, the pins 18 can come off the hole portions 124 of the fixed tube support portion 12, are moved sideways by receiving lateral forces from the thread support portion 15 being biased in the proximal direction by the restoring force of the coil spring 22, so that the pins 18 come off the hole portions 124, and are discharged (stored) into the hole portions 112 This condition is said to be a condition where the fixed tube support portion 12, which is an internal structure, is disposed in the third position in the casing 11

Figure 21:
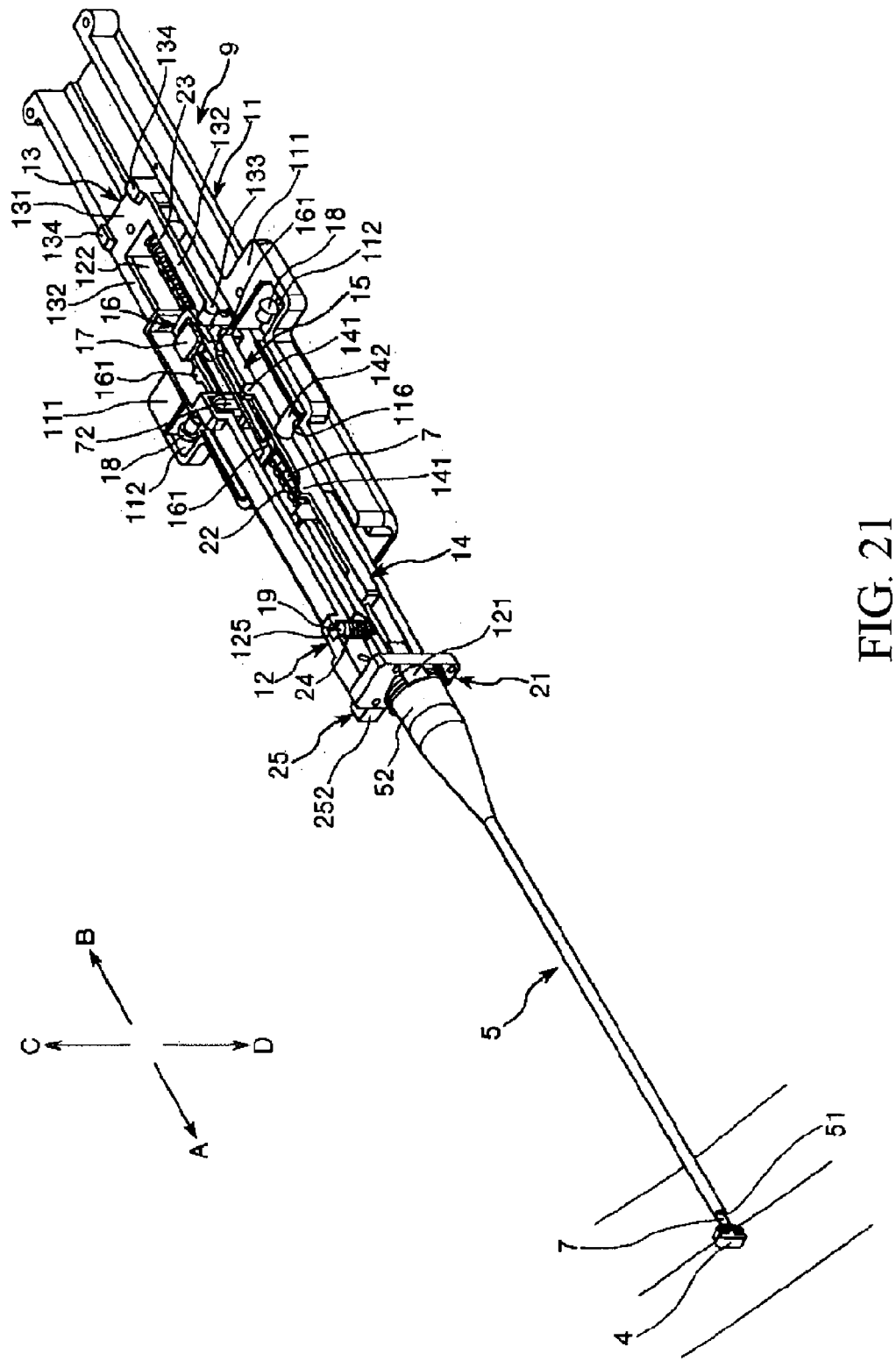
FIG. 21 is a perspective view for illustrating an action (operation) of the tissue closing device shown in FIG. 1

As a result, the locking of the thread support portion 15 by the pair of pins 18 is canceled, resulting in that the thread support portion 15 can be moved to the proximal direction relative to the fixed tube support portion 12 Namely, by canceling the locking of the thread support portion 15 by the pair of pins 18, relative movements of the thread support portion 15 and the fixed tube support portion 12 are enabled (relative movements of the clip 4 and the fixed tube 7 are enabled), whereby the restriction for maintaining the coil spring 22 in the deformed state (active state) is canceled By this, as shown in FIG. 21, the thread support portion 15 is moved to the proximal direction relative to the fixed tube support portion 12 by the restoring force of the coil spring 22 Thus, the pair of pins 18 and the pair of hole portions 112 of the casing 11 function as trigger means for actuating the coil spring 22 by canceling the restriction for maintaining the coil spring 22 in the active state In addition, an operation (trigger operation) for moving the pair of pins 18, locking the thread support portion 15, sideways (to the positions for canceling the locking) is automatically performed by the operator's operation of pulling off (moving) the handling portion 9 to the proximal side and by the biasing force of the coil spring 22

Figure 22:
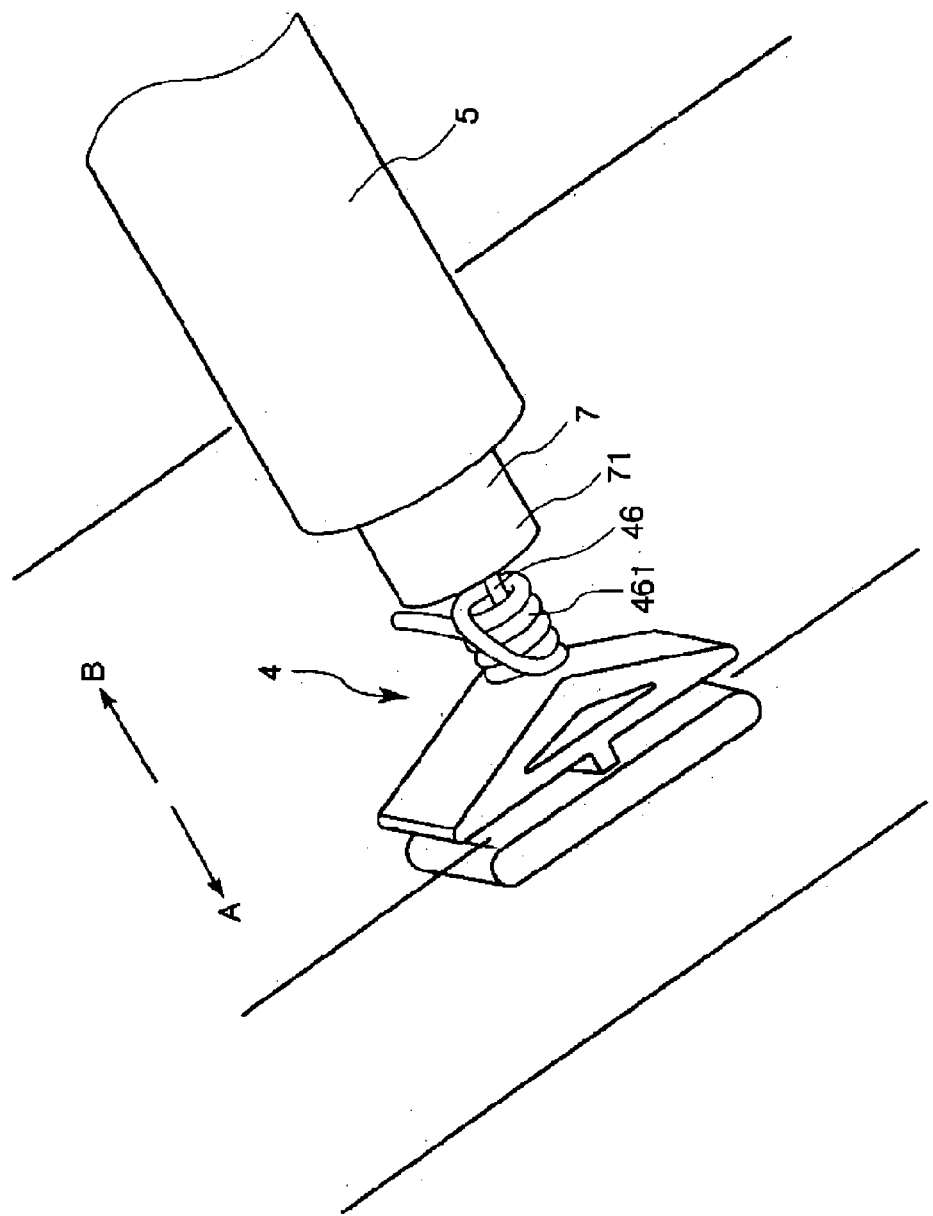
FIG. 22 is a perspective view for illustrating an action (operation) of the tissue closing device shown in FIG. 1

When the thread support portion 15 is moved to the proximal direction relative to the fixed tube support portion 12, as shown in FIGS. 21 and 22, the thread 8 is moved to the proximal direction, the thread 46 of the clip 4 is pulled in the proximal direction by the thread 8, the knot 461 of the thread 46 of the clip 4 is locked to a distal end portion 71 of the fixed tube 7, and, further, the deformation portion 42 is locked (indirectly locked) through the knot 461, whereby the knot 461 is moved to the distal direction, the thread 46 is tightened, and the deformation portion 42 is deformed In this manner, with the fixed tube support portion 12 (which is an internal structure) moved from the first position to the second position inside the casing 11, the clip 4 is securely fitted to the in vivo tissue to such an extent as not to come off even if a predetermined tension is reached or exceeded, so that the coil spring 22 which is an actuating member (first elastic member) can be triggered In addition, with the fixed tube support portion 12 (which is an internal structure) moved from the second position to the third position inside the casing 11, triggering of the trigger means (canceling of the restrictor) is carried out, whereby the fixed tube support portion 12 and the thread support portion 15 are moved relative to each other, and the deformation portion 42 is deformed These operations are all automatically performed by only the operation of pulling off the casing 11 in the condition where the clip 4 is anchored to the in vivo tissue As a result, the deformation portion 42 covers the wound hole and a peripheral portion of the wound hole from the outside of the blood vessel wall, the seal portion 41 covers the wound hole and a peripheral portion of the wound hole from the inside of the blood vessel wall, and the blood vessel wall is clamped between the seal portion 41 and the deformation portion 42, whereby the wound hole is closed Then, the condition where the deformation portion 42 is in the above-mentioned form is maintained (fixed) by the thread 46

Figure 23:
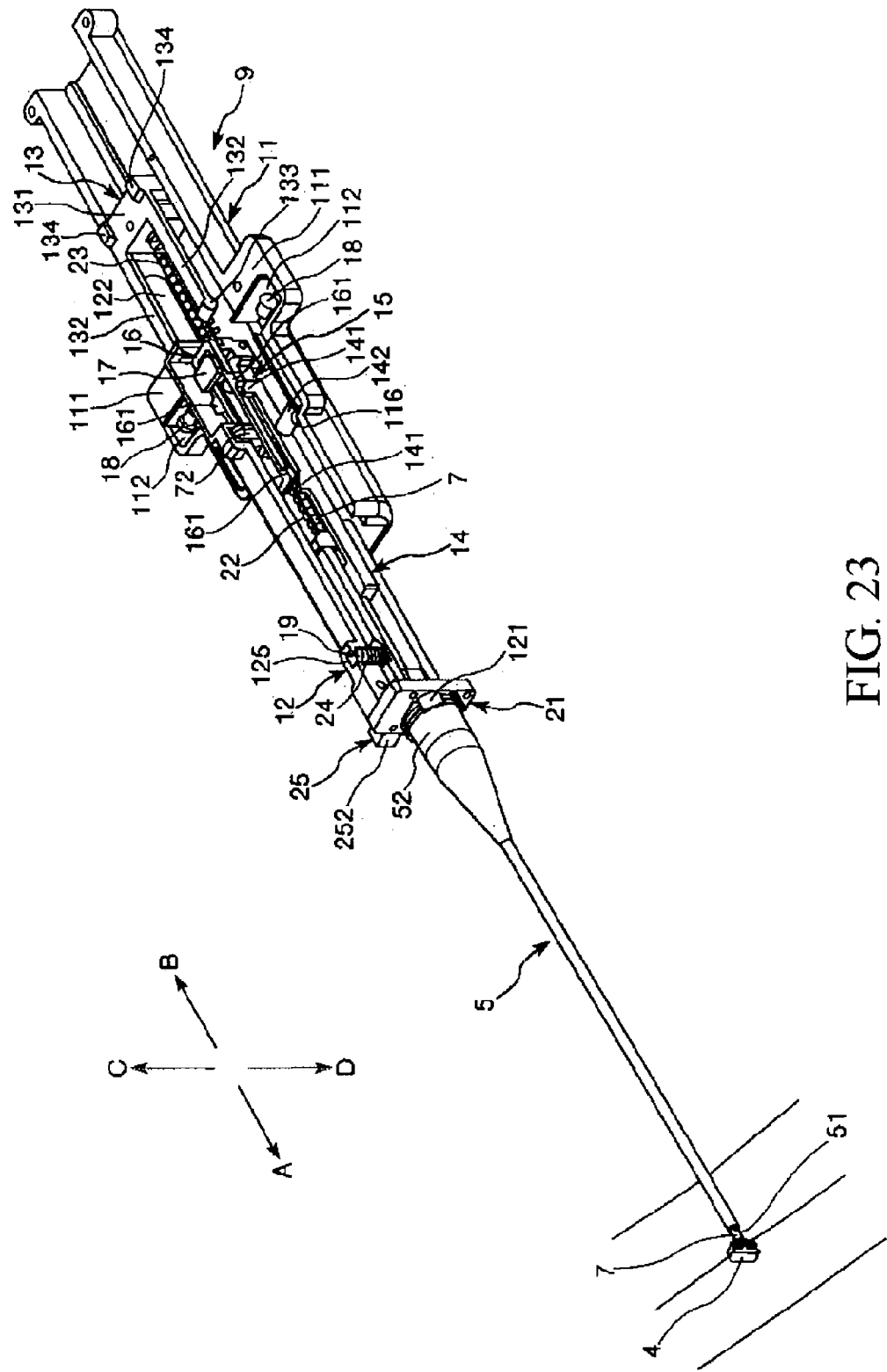
FIG. 23 is a perspective view for illustrating an action (operation) of the tissue closing device shown in FIG. 1

Besides, when the handling portion 9 (casing 11) is moved further to the proximal direction in the condition where the seal portion 41 of the clip 4 is in contact with the inside surface of the blood vessel wall, as shown in FIG. 23, after the locking of the thread support portion 15 by the pair of pins 18 is canceled (the restriction for maintaining the coil spring 22 in the deformed state is canceled), i e, after the deformation of the deformation portion 42 of the clip 4 is completed, the casing 11 is moved further in the proximal direction relative to the fixed tube support portion 12, and the cover tube support portion 14 is moved further in the proximal direction relative to the fixed tube support portion 12 and the thread support portion 15 together with the casing 11

Figure 24:
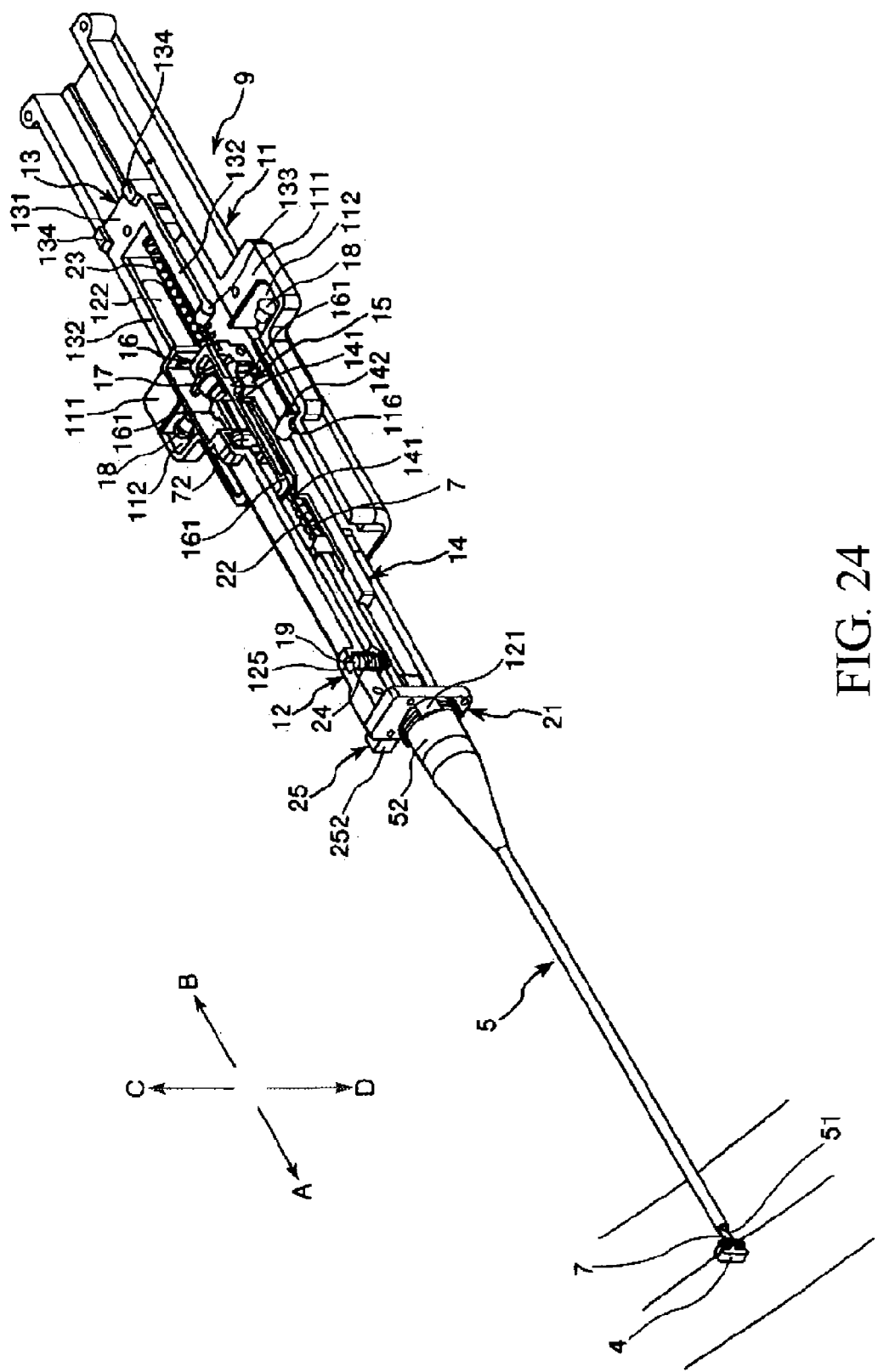
FIG. 24 is a perspective view for illustrating an action (operation) of the tissue closing device shown in FIG. 1

Then, when the projections 141 of the cover tube support portion 14 are moved to the positions of the projections 161 of the lifter 16 as shown in FIG. 24, the projections 161 are pushed upward by the projections 141, and the lifter 16 is moved upward, whereby the pin 17 is moved upward (in the direction of coming off the thread support portion 15) As a result, the connection between the thread 8 and the thread support portion 15 by the pin 17 is canceled, whereby the connection between the thread 8 and the thread 46 of the clip 4 is canceled (the retained state of the clip 4 by the thread 8 is canceled) Specifically, the bent-back portion 81 of the thread 8 comes off the pin 17, resulting in that the thread 8 can be pulled off from the loop 462 of the thread 46 of the clip 4

Therefore, connection canceling means and a retained state canceling means are constituted of the lifter 16, the projections 161 and the projections 141

Figure 25:
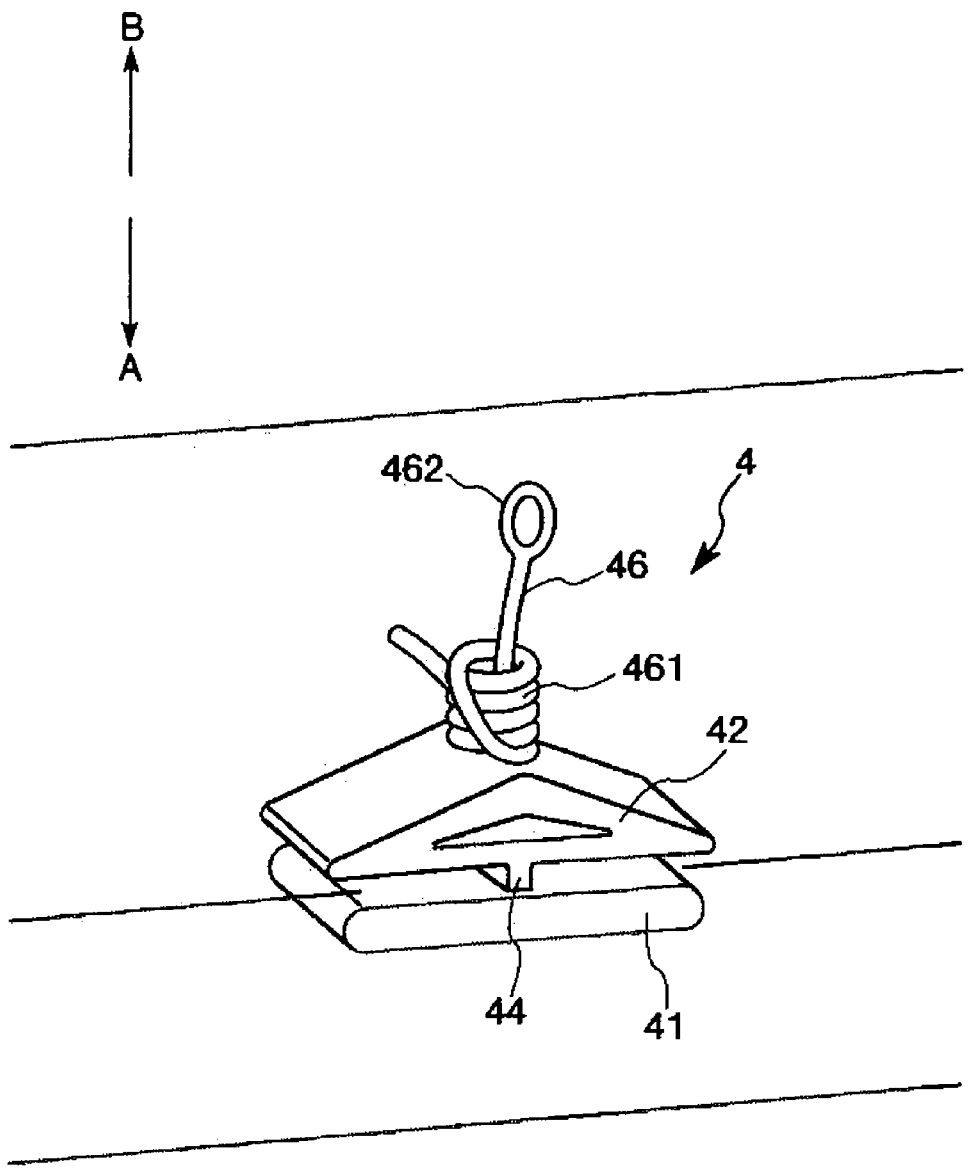
FIG. 25 is a perspective view for illustrating an action (operation) of the tissue closing device shown in FIG. 1

Subsequently, when the handling portion 9 (casing 11) is moved further to the proximal direction and the body portion 2 is pulled off, the clip 4 is disposed (put to indwell) in the living organism, as shown in FIG. 25

Figure 26:
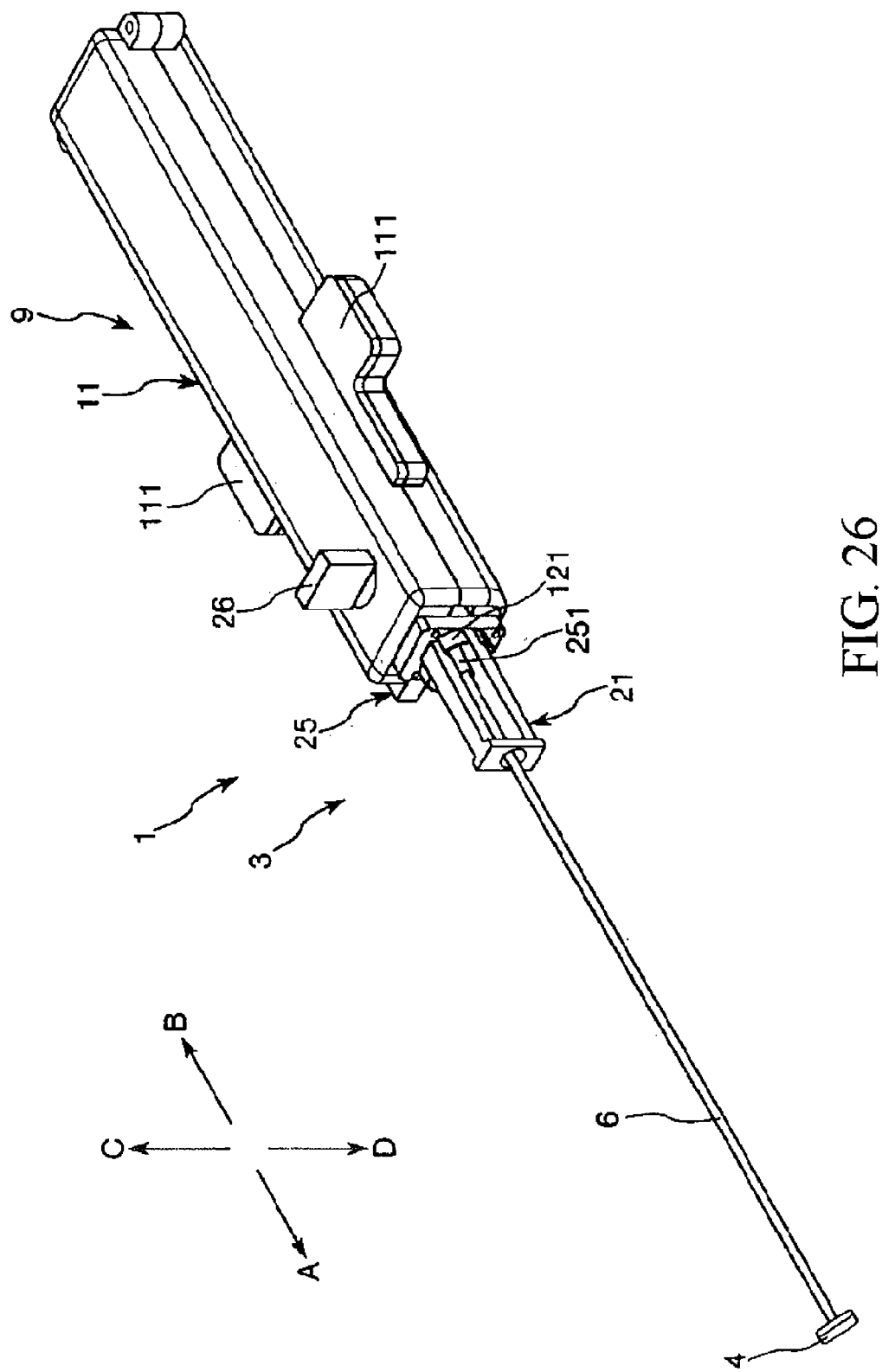
FIG. 26 is a perspective view showing a second embodiment (locked condition) of the tissue closing device as disclosed herein
Figure 27:
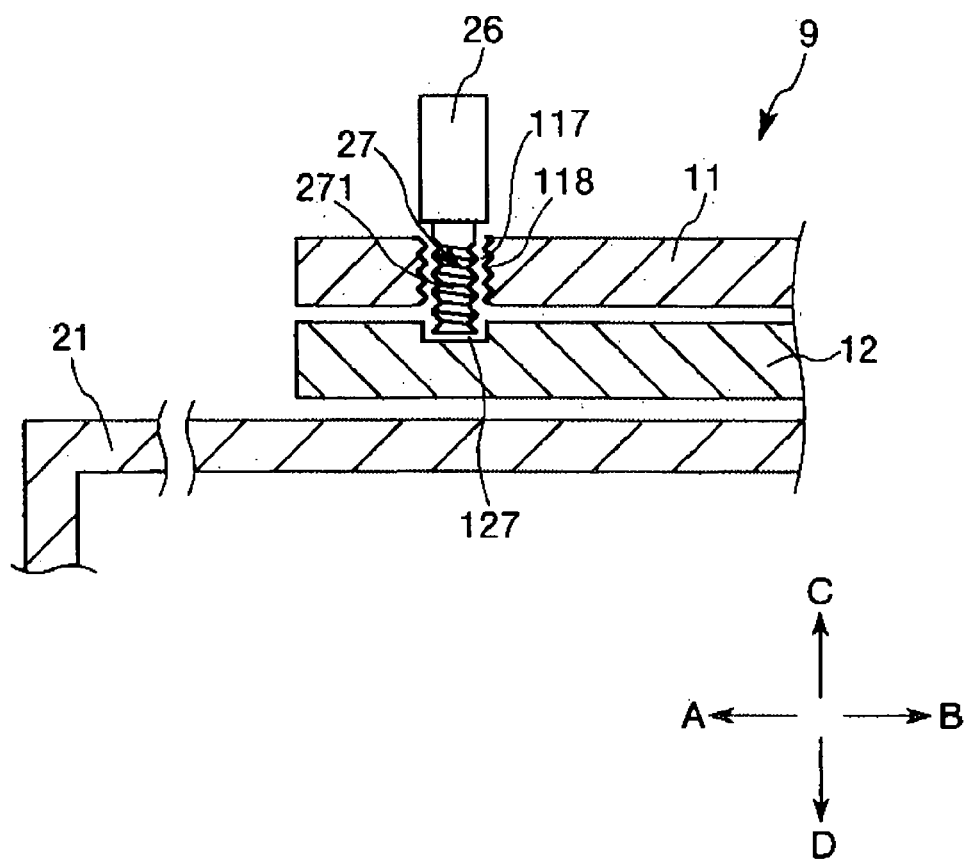
FIG. 27 is a sectional view showing a part on the distal side of a handling portion of the tissue closing device shown in FIG. 26
Figure 28:
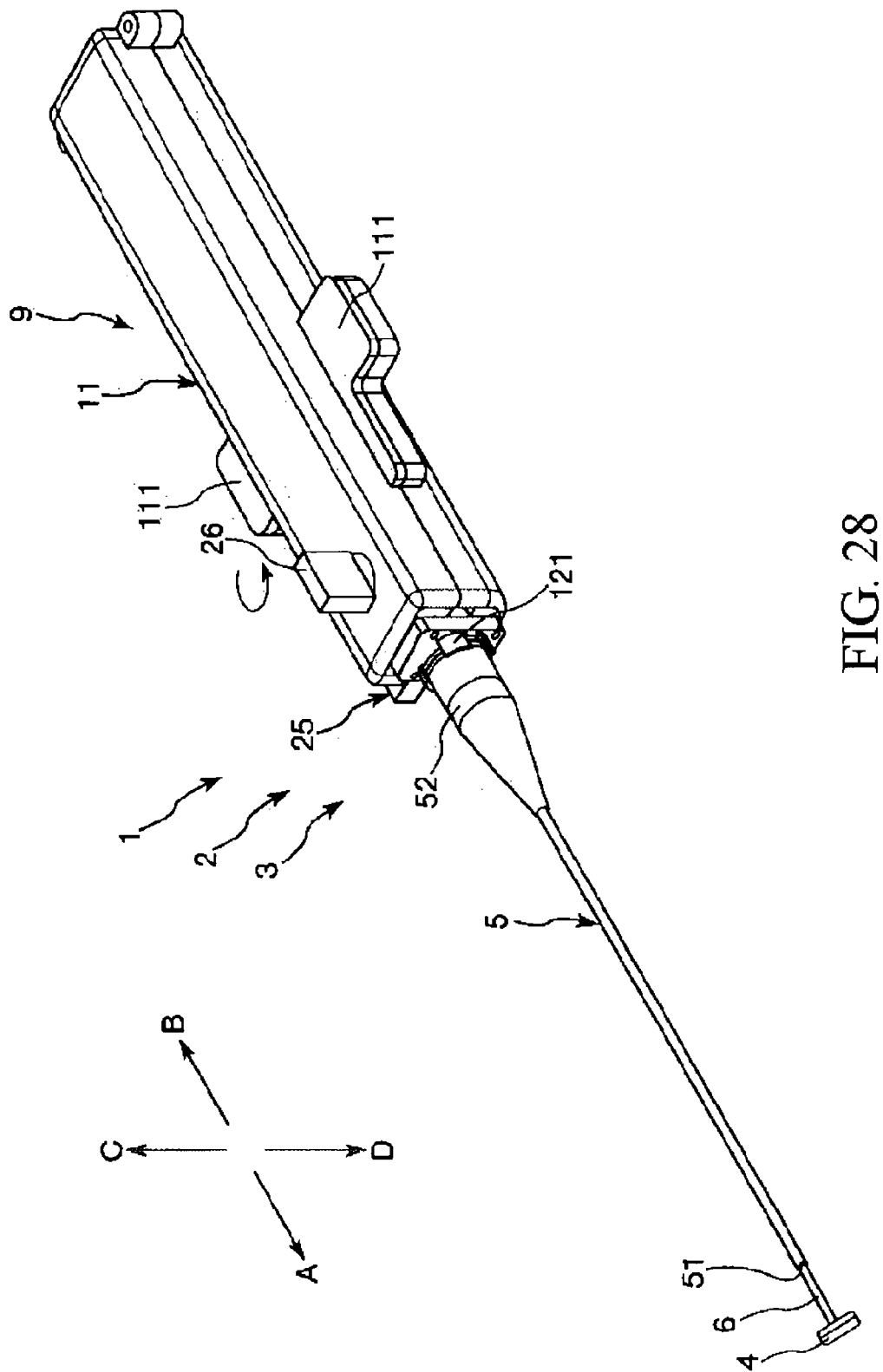
FIG. 28 is a perspective view showing the second embodiment (unlocked condition) of the tissue closing device
Figure 29:
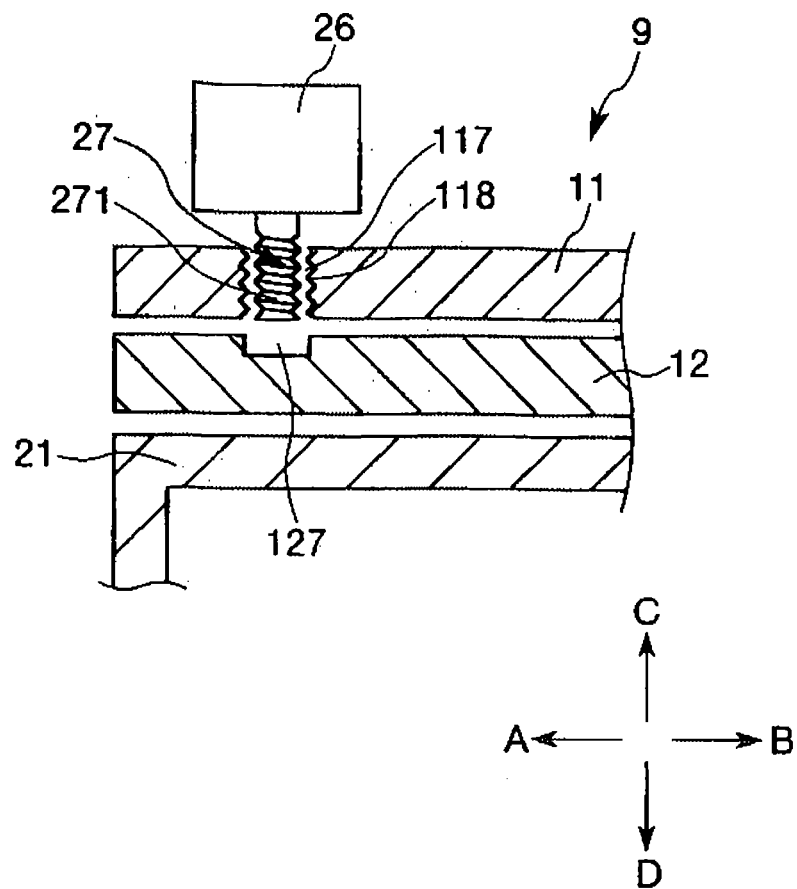
FIG. 29 is a sectional view showing a part on the distal side of the handling portion of the tissue closing device shown in FIG. 28

As has been described above, according to the tissue closing device 1, by the operation of simply moving the handling portion 9 (casing 11) to the proximal direction (one direction), all the operations (motions) are performed without need for the user's operations, a wound hole is closed by the clip 4, and the clip 4 can be disposed (put to indwell) in a living organism Therefore, the tissue closing device 1 can be easily operated even by one hand, and a stanching work for a wound hole formed in an in vivo tissue membrane such as a blood vessel wall can be performed easily, speedily and assuredly Namely, the wound hole can be closed (closed up) easily, speedily and assuredly, and perfect stanching can be achieved Particularly, since the deformation portion 42 of the clip 4 is deformed by the restoring force of the coil spring 22, the operation of manually deforming the deformation portion 42 of the clip 4 by the operator can be eliminated, thereby closing the wound hole extremely easily, speedily and assuredly In addition, in the condition where the deformation portion 42 of the clip 4 is in a desired form between the first form and the second form, the condition can be maintained by the thread 46 This makes it possible to cope with various conditions (statuses) of in vivo tissue membranes Second Embodiment Now, a second embodiment of the tissue closing device according to the present invention will be described below FIG. 26 is a perspective view of the second embodiment (locked condition) of the tissue closing device according to the present invention, FIG. 27 is a sectional view of a part on the distal side of a handling portion in the tissue closing device shown in FIG. 26, FIG. 28 is a perspective view of the second embodiment (unlocked condition) of the tissue closing device according to the present invention, and FIG. 29 is a sectional view of a part on the distal side of the handling portion in the tissue closing device shown in FIG. 28

Incidentally, for convenience of description, in FIGS. 26 to 29, the direction of arrow A will be referred to as "distal", the direction (hand side) of arrow B as "proximal", the direction of arrow C as "upper", and the direction of arrow D as "lower", in the following description Now, the tissue closing device 1 according to the second embodiment will be described below, the description being centered on the differences of the second embodiment from the above-described first embodiment, and description of the same items as above being omitted As shown in these figures, in the tissue closing device 1 according to the second embodiment, a lever (knob) 26 is provided at a distal end portion of a handling, portion 9, as an operating portion (operating member) for changeover between a condition (locked condition) where relative movements of a fixed tube support portion 12 and a casing 11 are inhibited and a condition (unlocked condition) where relative movements of the fixed tube support portion 12 and the casing 11 are enabled As shown in FIG. 27, a lock pin 27 provided with screw threads 271 at its outer circumferential portion is provided at a lower portion of the lever 26

In addition, a hole portion 117 in which to insert the lock pin 27 is formed in an upper portion of a distal end portion of the casing 11, and the inner circumferential surface of the hole portion 117 is provided with screw threads 118 for screw engagement with the screw threads 271 of the lock pin 27

Besides, a bottomed hole portion 127 in which to insert the lock pin 27 is formed in an upper portion of a distal end portion of the fixed tube support portion 12, at a position corresponding to the hole portion 117

In the locked condition as shown in FIGS. 26 and 27, the lock pin 27 is inserted in the hole portion 127 of the fixed tube support portion 12 This inhibits the fixed tube support portion 12 from moving relative to the casing 11

Next, when an arrangement device 3 is gradually inserted into a through-lumen 51 of a sheath 5 from the proximal side of the sheath 5 and a connector 121 of the arrangement device 3 is fitted to a hub 52 of the sheath 5, as shown in FIG. 28, a charge member 21 is moved in the proximal direction to contract a coil spring 22, as has been described in the first embodiment In addition, by the fitting between the connector 121 and the hub 52, the charge member 21 is locked relative to the fixed tube support portion 12 and is immovable (the positional relationship between the charge member 21 and the fixed tube support portion 12 is fixed) By this, the coil spring 22 is maintained in a contracted state (deformed state, active state)

Figure 30:
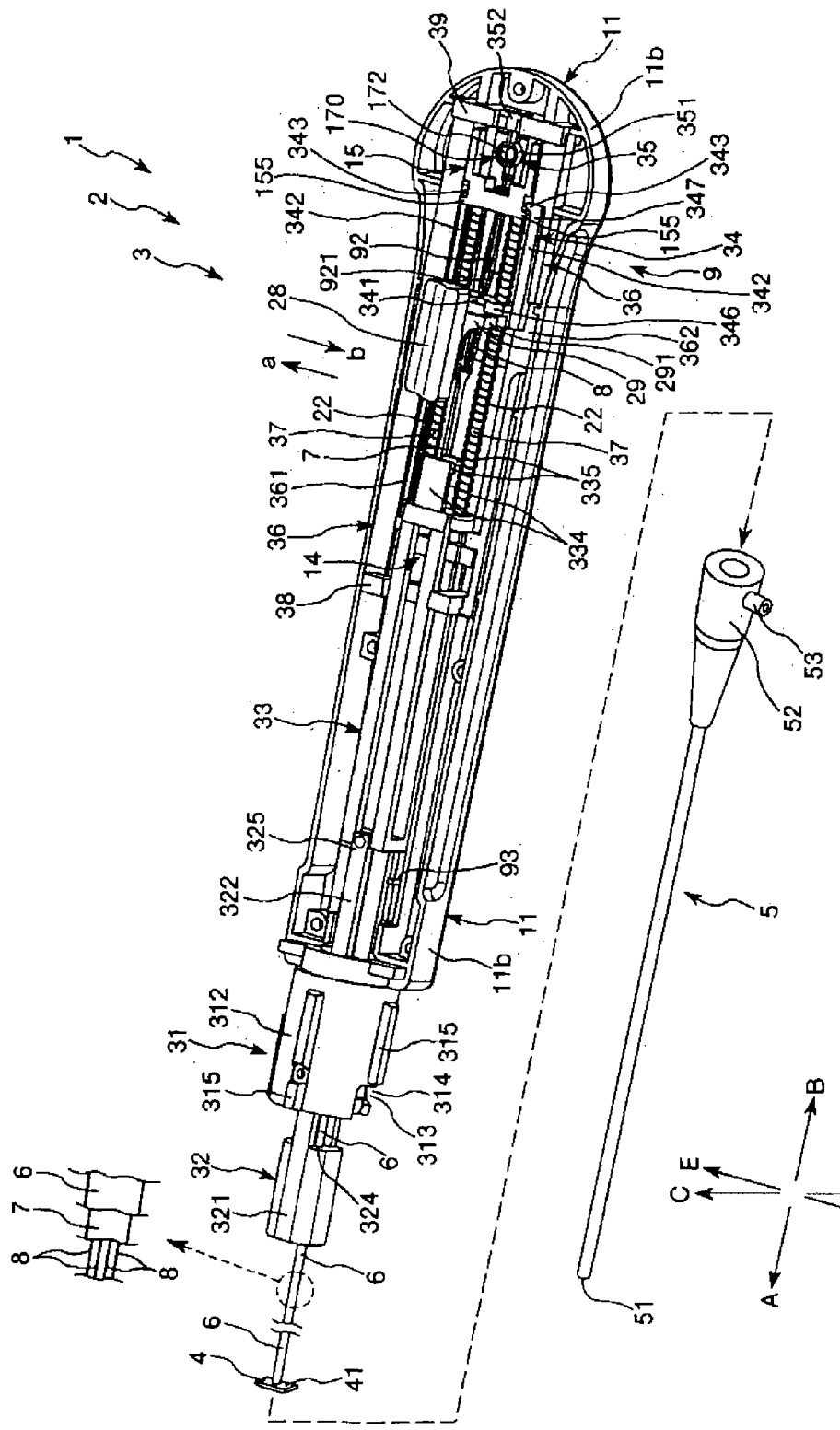
FIG. 30 is a perspective view of a third embodiment of the tissue closing device as disclosed herein
Figure 31:
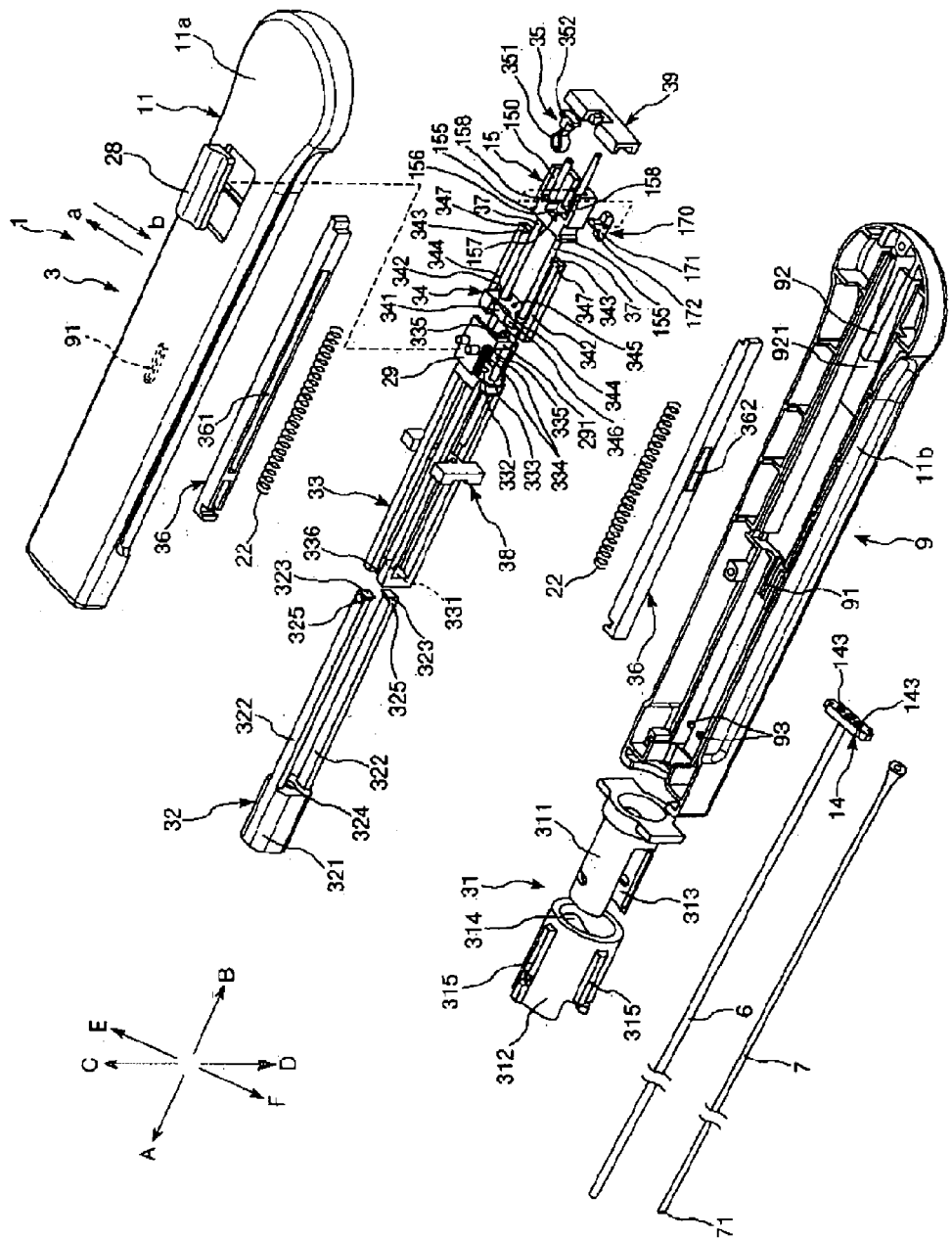
FIG. 31 is an exploded perspective view (members (component parts)) of the tissue closing device shown in FIG. 30
Figure 32:
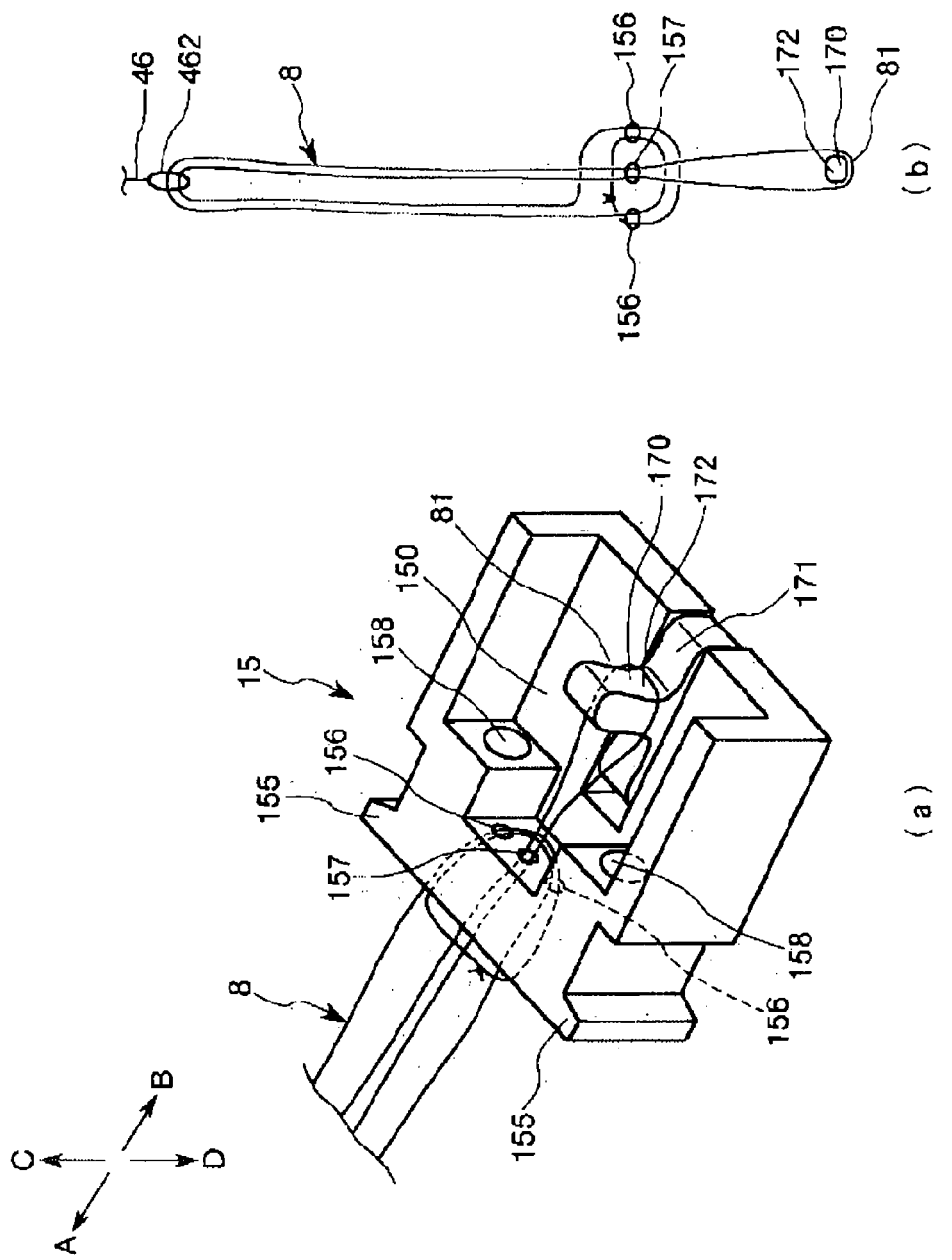
FIGS. 32(a) and 32(b) are perspective views showing a thread support portion, a pin and a thread in the tissue closing device shown in FIG. 30

Next, when the lever 26 is rotated (rotationally operated) by a predetermined angle (about 90°, in the example shown) in a predetermined direction (counterclockwise, in the example shown) starting from the above-mentioned locked condition, as shown in FIG. 28, the lock pin 27 is moved upward to come off the hole portion 127 of the fixed tube support portion 12, as shown in FIG. 29 As a result, the casing 11 is movable relative to the fixed tube support portion 12 Namely, the unlocked condition is obtained This ensures that, as mentioned above in the first embodiment, when the casing 11 of the handling portion 9 is gripped by fingers of a hand and the handling portion 9, i e, a body portion 2 (arrangement device 3) is slowly moved to one direction, i e, to a direction for pulling out of a wound hole (proximal direction) to thereby pull off the body portion 2 from the wound hole, all the operations (motions) are performed sequentially and continuously, resulting in that the wound hole is closed with a clip 4 and the clip 4 is disposed (put to indwell) in the living organism Incidentally, when the lever 26 is rotated by a predetermined angle (about 90°, in the example shown) in the reverse direction to the above (clockwise, in the example shown) starting from the above-mentioned unlocked condition, as shown in FIG. 26, the lock pin 27 is moved downward to be inserted into a hole portion 127 of the fixed tube support portion 12, as shown in FIG. 27 As a result of this, the fixed tube support portion 12 is inhibited from moving relative to the casing 11 Namely, the locked condition is again obtained According to the present tissue closing device 1, the same effects as those of the tissue closing device 1 in the first embodiment described above can be obtained In the present tissue closing device 1, the changeover between the locked condition and the unlocked condition can be made based on the user's decision, so that the device can be prevented from operating erroneously Third Embodiment Now, a third embodiment of the tissue closing device according to the present invention will be described below FIG. 30 is a perspective view illustrating the third embodiment of the tissue closing device according to the present invention, FIG. 31 is an exploded perspective view (showing the members (component parts)) of the tissue closing device shown in FIG. 30, FIGS. 32(a) and 32(b) show a thread support portion, a pin, and a thread in the tissue closing device shown in FIG. 30, FIG. 32(a) is a perspective view, and FIG. 32(b) is a schematic plan view Besides, FIGS. 32(a) to 39(b) are perspective views for illustrating the operations (movements) of the tissue closing device shown in FIG. 30, in which 32(a), 33(a), 34(a), 35(a), 36(a), 37(a), 38(a), and 39(a) in each figure shows the handling portion side, and 32(b), 33(b), 34(b), 35(b), 36(b), 37(b), 38(b), and 39(b) shows the distal end portion side Incidentally, in FIGS. 30 and 33(a) to 39(a), an upper cover of a casing is not shown for indicating the internal structure For a rail on one side (on the side of arrow F), the inside thereof is shown In addition, in FIG. 30, the inside of a cover tube which is surrounded by the broken-line circle and the inside of a fixing tube are enlarged shown Besides, in FIGS. 33(a) to 39(a), for obviating complexity of drawings, the thread is omitted, exclusive of a part thereof.

Furthermore, for convenience of description, in FIGS. 30 to 39(b), the direction of arrow A indicates the "distal (side)", the direction of arrow B (hand-operated side) indicates the "proximal (side)", the direction of arrow C indicates the "upper (side)", and the direction of arrow D indicates the "lower (side)"

Now, the tissue closing device 1 according to the third embodiment will be described, centered on the differences thereof from the above-described first embodiment, and descriptions of the items equivalent to the above will be omitted As shown in FIGS. 30 and 31, in the tissue closing device 1 in the third embodiment, a handling portion 9 of an arrangement device 3 has a casing (main body) 11, a cover tube support portion 14 (cover member support portion) for supporting a cover tube 6, a thread support portion (maintaining member support portion) 15 for supporting a thread 8, a pin (connecting means) 170 turnably disposed at the thread support portion 15 and detachably connecting the thread 8 to the thread support portion 15, a first charging member 32, a second charging member 33, a slide connecting member (connecting means) 34 for detachably connecting the thread support portion 15 and the second charging member 33, a pair of coil springs (springs) 22 which are elastic members (actuating members), a pair of guide bars 37, a lever (knob) 28, a lock portion 29 joined to the lower side of the lever 28, and a stopper 35

Here, the tissue closing device 1 of the third embodiment does not have a fixed tube support portion (lock member support portion) 12 As will be described later, the second charging member 33 and the slide connecting member 34 function as the fixed tube support portion (lock means support portion) This simplifies the structure In addition, a coil spring (second elastic member) 33 is not provided Instead, the stopper 35 is provided Besides, the first charging member 32 and the second charging member 33 constitute charging means Further, the pair of coil springs 22 correspond to the first elastic member (actuating member) in the claims Now, the components will be described sequentially The casing 11 has an upper cover 11a located on the upper side, and a lower cover 11b located on the lower side and joined to the upper cover 11a. The casing 11 has a tubular (angular tube-like) outside look with a roughly rectangular parallelopiped shape, and it is rounded on the proximal side At a distal end portion of the casing 11, a connector 31 to which a hub 52 of a sheath 5 is mounted (fitted) is provided as a sheath mounting mechanism for mounting the sheath 5 to the arrangement device 3 (the casing 11) The connector 31 is composed of an inner tube portion 311 into which the hub 52 is inserted, and an outer tube portion 312 disposed on the outer periphery of the inner tube portion 311 so as to be turnable (rotatable) in the circumferential direction The peripheral wall of the inner tube portion 311 is provided with a rectilinear slot 313 opening to the distal end, and the peripheral wall of the outer tube portion 312 is provided with a spiral slot 314 opening to the distal end The outer tube portion 312 can be rotated in a predetermined sense relative to the inner tube portion 311 until a distal end portion of the slot 314 in the outer tube portion 312 coincides with a distal end portion of the slot 313 in the inner tube portion 311, and the outer tube portion 312 can be rotated in the reverse sense until a proximal end portion of the slot 314 coincides with a proximal end portion of the slot 313

In addition, on the outer peripheral surface of the outer tube portion 312, a plurality of (in the example shown, four) ribs 315 functioning as finger hook portions at the time of an operation of mounting the sheath 5 are formed at regular intervals (regular angular intervals)

On the other hand, at a side portion of the hub 52 of the sheath 5, a port portion (projection) 53 having a lumen (passage) communicating with a through-lumen 51 is formed At the time of mounting the sheath 5 to the arrangement device 3, in the condition where the position of the distal end portion of the slot 313 in the inner tube portion 311 coincides with the position of the distal end portion of the slot 314 in the outer tube portion 312, a proximal end portion of the hub 52 is inserted into the inner tube portion 311 so that the port portion 53 of the hub 52 of the sheath 5 is located at the distal end portion of the slot 313 in the inner tube portion 311 and the distal end portion of the slot 314 in the outer tube portion 312, and the outer tube portion 312 is rotated in a predetermined sense (in the example shown, counterclockwise as viewed from the distal side) By this operation, the port portion 53 is pushed toward the proximal side by an edge portion fronting on the slot 314 of the outer tube portion 312, and is gradually moved toward the proximal side along the slot 313 in the inner tube portion 311. In short, the hub 52 of the sheath 5 is moved to the proximal direction, to be inserted and fixed in the inner tube portion 311 In this manner, the sheath 5 is mounted onto the arrangement device 3

In addition, at a central portion of the casing 11 and on the inside of the upper cover 11a and on the inside of the lower cover 11b, grooves 91 into which to insert a proximal end portion 325 of a rod-like element 322 corresponding to the first charging member 32 which will be described later are formed oppositely to each other and along the longitudinal direction of the arrangement device 3 (the casing 11)

Besides, at a proximal end portion of the casing 11 and on the inside of the lower cover 11b, a rib 92 is formed along the longitudinal direction of the arrangement device 3 (the casing 11), and a step portion 921 is formed on the distal side of a distal end portion of the rib 92

In addition, at a distal end portion of the casing 11 and on the inside of the lower cover 11b, a pair of projections 93 are formed A proximal end portion of a base portion 321 of the first charging member 32 which will be described later is made to abut on the pair of projections 93, whereby the first charging member 32 is inhibited from moving in the proximal direction beyond the projections 93

Besides, at a central portion inside the casing 11, a guide bar support portion 38 is provided (fixed), and at a proximal end portion inside the casing 11, a guide bar support portion 39 is provided (fixed)

The pair of guide bars 37 are disposed between the guide bar support portion 38 and the guide bar support portion 39 Of the guide bars 37, distal end portions are held (supported) by the guide bar support portion 38, and proximal end portions are held (supported) by the guide bar support portion 39 Besides, the guide bars 37 are disposed along the longitudinal direction of the arrangement device 3 (the casing 11) so that they are parallel to each other Incidentally, while the guide bars 37 are each composed of a pipe (pipe member) in the example shown, they are not limited to this configuration and may be solid In addition, at side portions in the casing 11, a pair of rails 36 are provided (fixed) over the range from the guide bar support portion 38 to the guide bar support portion 39 The rails 36 are disposed along the longitudinal direction of the arrangement device 3 (the casing 11) so that they are parallel to each other Each of the rails 36 is provided with a groove 361 extending along the longitudinal direction (axial direction) thereof. The grooves 361 are formed on the inner sides of the rails 36 so that they face each other In addition, the grooves 361 of the rails 36 are provided in their bottom portions (side walls) with hole portions 362 into which proximal end portions 347 of rod-like elements 342 corresponding to the slide connecting members 34 (described later) are inserted when the pair of coil springs 22 (described later) actuate (restore) Each the hole portions 362 is located near a central portion of the rail 36

Besides, the first charging member 32, the second charging member 33, the guide bar support portion 38, the slide connecting member 34, and the thread support portion 15 are disposed inside the casing 11 so that they can be moved, relative to the casing 11, in the longitudinal direction of the arrangement device 3 (the casing 11)

In this case, the first charging member 32, the second charging member 33, the slide connecting member 34, and the thread support portion 15 are disposed in this order along the direction of from the distal side toward the proximal side The second charging member 33 is so disposed that the guide bar support portion 38 is located between its distal end portion and its proximal end portion In addition, the cover tube support portion 14 is so disposed as to be located between the guide bar support portion 38 and a proximal end portion of the second charging member 33

Besides, the base portion 321 of the first charge portion 32 is located on the distal side relative to the connector 31

The slide connecting member 34 is composed of a base portion 341, and a pair of rod-like elements 342 projecting in the proximal direction from both side portions of the base portion 341

On proximal end portions 347 of the rod-like elements 342, pawls 343 facing each other and projecting toward the inside are erectingly provided In addition, the base portion 341 is provided with a pair of hole portions 344 through which to pass the pair of guide bars 37

Besides, the base portion 341 is provided in its central portion with a hole portion 345 through which to pass the thread 8

Further, the base portion 341 is provided with a projection 346 projecting upwards to be locked on a projected portion 291 of the lock portion 29

As shown in FIGS. 30 to 32B, at both side portions of a distal end portion of the thread support portion 15, projections 155 for engagement with the corresponding pawls 343 of the slide connecting member 34 are formed In addition, the thread support portion 15 is provided, on the proximal side relative to a distal end portion thereof, with a recessed portion 150 opened to the upper side and to the proximal end thereof.

Besides, the thread support portion 15 is provided in its distal end portion with a pair of hole portions 156 through which to pass the thread 8 Further, the distal end portion of the thread support portion 15 is provided, between the pair of hole portions 156, with a hole portion 157 through which to pass the thread 8

In addition, the distal end portion of the thread support portion 15 is provided with a pair of hole portions 158 through which to pass the pair of guide bars 37

The pin 170 is composed of a base portion 171, and a projection 172 erectingly provided at a central portion of the base portion 171

The pin 170 is disposed to be turnable, at its base portion 171, relative to the thread support portion 15, and it can assume an erected state where the projection 172 (the pin 170) is erecting and a fallen state where the projection 172 (the pin 170) is fallen The pin 170 is maintained in the erecting state by the abutment of the bottom surface (back surface) of the base portion 171 thereof on the upper surface of the rib 92 of the casing 11 Incidentally, the pin 170 is disposed in the recessed portion 150 of the thread support portion 15

The stopper 35 is composed of a C-shaped stopper body 351 provided with a gap on the distal side (i e opened on the distal side), and a support portion 352 supporting the stopper body 351, and the support portion 252 is disposed (fixed) on the guide bar support portion 39 The projection 172 of the pin 170 is inserted into the stopper body 351 of the stopper 35 This configuration ensures that the thread support portion 15 is retained (locked) by the stopper 35 through the pin 170, whereby the support portion 15 is inhibited from moving The pin 170 and the thread support portion 15 are inhibited by the stopper 35 from moving to the distal direction relative to the casing 11

In addition, at least the stopper body 351 of the stopper 35 has an appropriate hardness and is elastically deformable Besides, the length of the gap (gap distance) on the distal side of the stopper body 351 is set to be smaller than the outside diameter of the projection 172 of the pin 170

The above configuration ensures that until the force exerted on the thread support portion 15 (the pin 170) through the thread 8, i e, the force (pulling force) with which the thread support portion 15 is pulled in the distal direction through the thread 8 exceeds a predetermined threshold (predetermined value), the thread support portion 15 is inhibited from moving However, when the force has exceeded the threshold, the projection 172 of the pin 170 comes out of the gap of the stopper body 351, whereby it is made possible for the thread support portion 15 to move to the distal direction relative to the casing 11 In this case, as will be described later, the thread support portion 15 (the thread support portion 15, the slide connecting member 34, and the second charging member 33) is permitted to move in the distal direction, whereby it is made possible to cancel the restriction for retaining the coil springs 22 in the contracted state (deformed state, active state) In other words, the cancellation of the restriction for retaining the coil springs 22 in the contracted state becomes possible on condition that the force exerted on the thread support portion 15 has exceeded the predetermined threshold The threshold is preferably about 150-15,000 gf, more preferably about 200-1,000 gf This ensures that even if the clip 4 is somewhat caught inside a blood vessel or the like before the seal portion 41 of the clip 4 comes into secure contact with the wound hole and the surrounding tissue, the clip 4 can be expected to be released before the pin 170 slips off from the stopper 35 (unlocking is made), so that the clip 4 can be moved to the wound hole and the seal portion 41 can be brought into abutment on the wound hole and the surrounding tissue In addition, the pin 170 can be expected to slip off from the stopper 35 (unlocking is made) before the wound hole and the surrounding tissue are excessively pulled in the proximal direction by the clip 4 Thus, the seal portion 41 can be brought into abutment on the wound hole and the surrounding tissue safely and assuredly The thread 8 is composed of a double thread (double thread-like member) in which a thread (thread-like member) is turned back and one end portions of which is a bent-back portion 81 In addition, the thread 8 is passed through the hole portions 156 in the thread support portion 15 in its single-thread state and is then wound once around a distal end portion of the thread support portion 15 Thereafter, both end portions of the thread 8 are tied to each other, before being attached to the thread support portion 15

The thread 8 is passed through the clip 4 (a loop 462 of a thread 46 of the clip 4), is turned back at a distal end portion of the arrangement device 3 to retain the clip 4, then, in this condition, the thread is passed through the hole portion 157 in the thread support portion 15 Further, the bent-back portion 81 of the thread 8 is hooked on the projection 172 of the pin 170, with the result that the bent-back portion 81 is detachably connected to the thread support portion 15 by the pin 170 As has been described above, the other end portion (the end portion on the opposite side of the bent-back portion 81) of the thread 8 is attached to the thread support portion 15

The second charging member 33 is in a cage-like (frame-like) form with an overall outside shape of a roughly tetragonal column (parallelopiped)

The second charging member 33 is provided in its distal end portion with a hole portion 331 through which to pass the cover tube 6

In addition, the second charging member 33 is provided in its proximal end portion with a pair of hole portions 333 through which to pass the pair of guide bars 37 Further, a hole portion 332 through which to pass the fixed tube 7 is formed between the pair of hole portions 333 in the proximal end portion of the second charging member 33

Besides, at the proximal end portion of the second charging member 33, a pair of projected portions 334 projected in the proximal direction from an upper portion and a lower portion of the proximal end portion are erectingly provided At proximal end portions of the projected portions 334, pawls 335 facing each other and projecting toward the inside are erectingly provided The pair of pawls 335 are engaged with the base portion 341 of the slide connecting member 34

In addition, the distal end portion of the second charging member 33 is provided with a pair of recessed portions 336 in an upper portion and a lower portion thereof.

The first charging member 32 is composed of a base portion 321, and a pair of rod-like elements 322 projecting in the proximal direction from an upper portion and a lower portion of a proximal end portion of the base portion 321

On proximal end portions 325 of the rod-like elements 322, projected portions 323 facing each other and projected toward the inside are erectingly provided The pair of projected portions 323 are engaged with the pair of recessed portions 336 in the distal end portion of the second charging member 33

In addition, the base portion 321 of the first charging member 32 is provided in its central portion with a hole portion 324 through which to pass the cover tube 6

The cover tube support portion 14 is provided with a pair of hole portions 143 through which to pass the pair of guide bars 37, and a proximal end portion of the cover tube 6 is fixed (supported) between the pair of hole portions 143 in the cover tube support portion 14

Besides, a proximal end portion of the fixed tube 7 inserted in the cover tube 6 is located between a proximal end portion of the second charging member 33 and the base portion 341 of the slide connecting member 34

The outside diameter of a proximal end portion of the fixed tube 7 is set to be greater than the inside diameter of the hole portion 332 in a proximal end portion of the second charging member 33 and the inside diameter of the hole portion 345 in the base portion 341 of the slide connecting member 34 This makes it possible to prevent the proximal end portion of the fixed tube 7 from slipping off from the hole portion 332 in the second charging member 33 and the hole portion 345 of the slide connecting member 34 As a result, in the condition where the pair of pawls 335 of the second charging member 33 is engaged with the base portion 341 of the slide connecting member 34, the proximal end portion of the fixed tube 7 is held between the proximal end portion of the second charging member 33 and the base portion 341 of the slide connecting member 34, whereby the fixed tube 7 is supported (substantially fixed) by the second charging member 33 and the slide connecting member 34 Therefore, the second charging member 33 and the slide connecting member 34 constitute a fixed tube support portion (lock member support portion) for supporting the fixed tube 7

The pair of guide bars 37 are passed through the pair of hole portions 333 in the second charging member 33, the pair of hole portions 143 in the cover tube support portion 14, the pair of hole portions 344 in the slide connecting member 34, and the pair of hole portions 158 in the thread support portion 15 Further, both side portions of the cover tube support portion 14 and the pair of rod-like elements 342 of the slide connecting member 34 are inserted in the grooves 361 in the pair of rails 36

This ensures that the second charging member 33 and the thread support portion 15 are guided by the guide bars 37 along the longitudinal direction (axial direction) of the guide bars 37

In addition, the cover tube support portion 14 and the slide connecting member 34 are guided by the guide bars 37 and the rails 36 along the longitudinal direction (axial direction) of the guide bars 37 and the rails 36

Here, in an initial condition (the condition upon assembly) shown in FIG. 30, the pair of projected portions 323 of the first charging member 32 are engaged with the pair of recessed portions 336 in the distal end portion of the second charging member 33 This ensures that the first charging member 32 and the second charging member 33 are to be moved as one body.

Besides, in the initial condition, the pair of pawls 343 of the slide connecting member 34 are engaged with the pair of projections 155 on the distal end portion of the thread support portion 15 This ensures that the slide connecting member 34 and the thread support portion 15 are to be moved as one body Strictly, however, movement of the slide connecting member 34 and the thread support portion 15 is being inhibited by the stopper 35 and the lock portion 29

In addition, in the initial condition, the second charging member 33 and the slide connecting member 34 are spaced a predetermined distance each other This ensures that the first charging member 32 and the second charging member 33 are to be moved separately from the slide connecting member 34 and the thread support member 15

As described later, in a charged condition (the condition where the coil springs 22 are retained in their contracted state, i e, their active state) at the time of use shown in FIGS. 33 and 34, the pair of pawls 335 of the second charging member 33 are engaged with the base portion 341 of the slide connecting member 34 Simultaneously, the pair of recessed portions 336 in the distal end portion of the second charging member 33 and the pair of projected portions 323 of the first charging member 32 are disengaged from each other This ensures that the second charging member 33, the slide connecting member 34, the thread support portion 15, and the fixed tube 7 are to be moved integrally, and the thread support portion 15 is inhibited from moving relative to the fixed tube 7 (moving to the proximal direction)

In addition, the members for connecting the clip 4, the thread support portion 15, and the casing 11 along the longitudinal direction of the arrangement device 3 do not include any member that can extend and contract in the longitudinal direction of the arrangement device 3, such as a spring Therefore, in the charged condition, the distance between the clip 4 and the casing 11 is kept substantially constant until the force exerted on the thread support portion 15 through the thread 8 exceeds the above-mentioned predetermined threshold Besides, the pair of coil springs 22 are disposed in the outer periphery of the pair of guide bars 37, respectively Each of the coil springs 22 is passed through the hole portion 344 in the slide connecting member 34, and is located between the proximal end portion of the second charging member 33 and the distal end portion of the thread support portion 15 The distal end of each coil spring 22 abuts on the proximal end portion of the second charging member 33, and the proximal end of each coil spring 22 abuts on the distal end portion of the thread support portion 15 Incidentally, in the initial condition, the coil springs 22 are each in a natural state or a slightly contracted state The lever 28 is an operating portion (operating member) by which locked condition and unlocked condition are changed over from one to the other In the initial condition, the locked condition is where movements of the slide connecting member 34 and the thread support, portion 15 relative to the casing 11 are inhibited, and the unlocked condition is where such relative movements are permitted In the charged condition, the locked condition is where movements of the second charging member 33, the slide connecting member 34, the thread support portion 15, the fixed tube 7, and the pair of coil springs 22 relative to the casing 11 are inhibited, and the unlocked condition is where such movements are permitted.

The lever 28 is disposed on an upper surface on the outer side of an upper cover 11a of the casing 11 in such a manner that it can move (slide) in the directions of arrows "a" and "b" shown in FIGS. 30 and 31.

Figure 33:
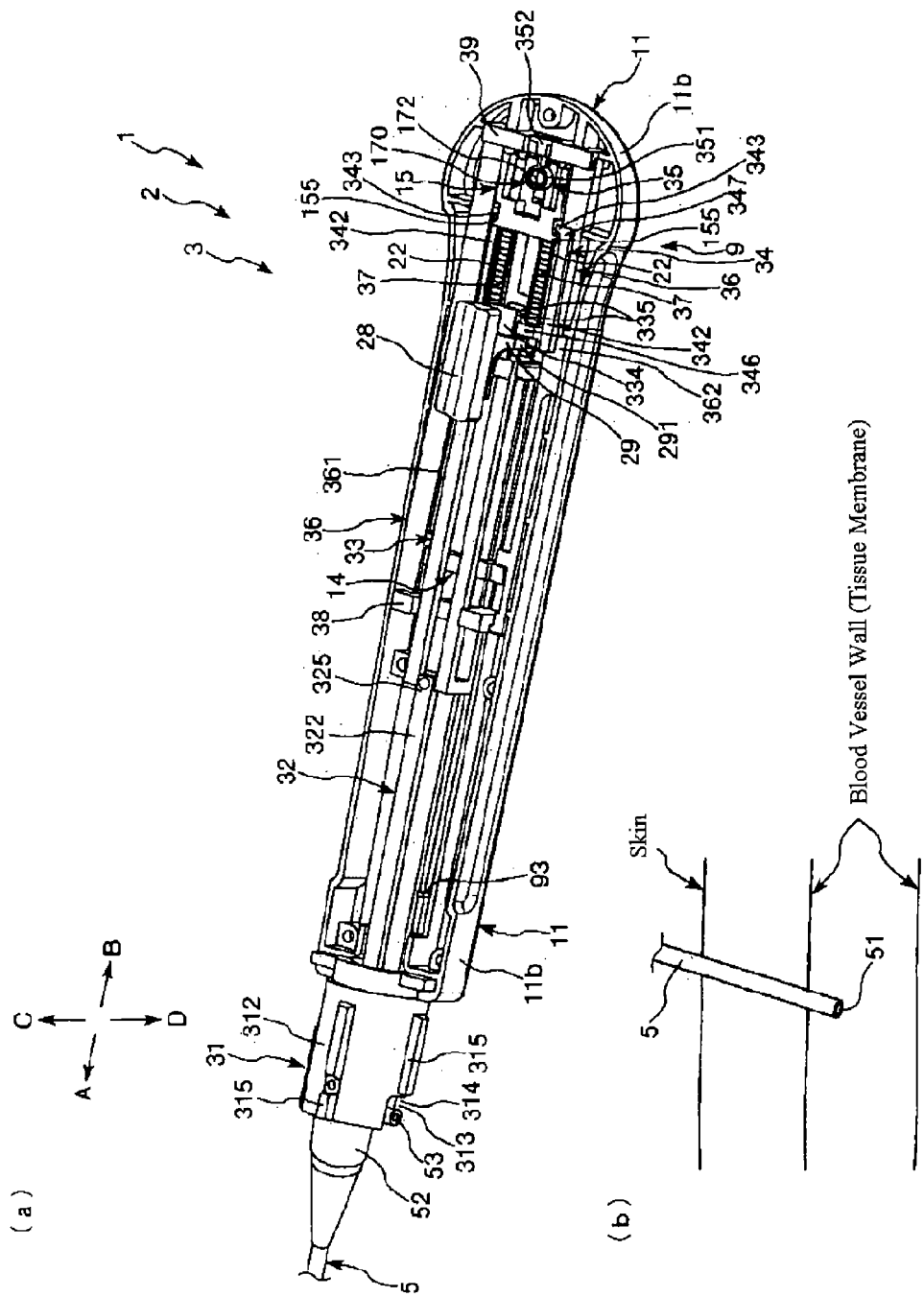
FIGS. 33(a) and 33(b) are perspective views for illustrating an action (operation) of the tissue closing device shown in FIG. 30

The lock portion 29 is joined to the lower side of the lever 28 so that the lever 28 and the lock portion 29 are to be moved as one body The lock portion 29 is located on the inside of the upper cover 11a of the casing 11 In addition, on the lock portion 29, the projected portion 291 projected downwards is erectingly provided When the lever 28 is located at the lock position shown in FIGS. 30 and 31, the projected portion 291 of the lock portion 29 abuts on the distal end side of the projection 346 of the slide connecting member 34, so that the projection 346 is locked by the projected portion 291, whereby the slide connecting member 34 is inhibited from moving to the distal direction The slide connecting member 34 is locked by the lock portion 29, so that in the initial condition, the slide connecting member 34 and the thread support portion 15 are inhibited from moving to the distal direction, whereas in the charged condition, the second charging member 33, the slide connecting member 34, the thread support member 15, the fixed tube 7, and the coil springs 22 are inhibited from moving to the distal direction, whereby an operation of causing the coil springs 22 to actuate is inhibited On the other hand, when the lever 28 is moved to the direction of arrow "b" (to be located in an unlocking position), the projected portion 291 of the lock portion 29 is moved (retracted) to a lateral side relative to the projection 346 of the slide connecting member 34 (to a position where the projection 346 is absent), whereby the projection 346 is unlocked from the projected portion 291 As a result, the movement of the slide connecting member 34 to the distal direction is permitted on condition that the condition where the thread support portion 15 is inhibited by the stopper 35 from moving is canceled (unlocked), namely, the locking of the slide connecting member 34 by the lock portion 29 is canceled In the charged condition, movements of the second charging member 33, the slide connecting member 34, the thread support portion 15, the fixed tube 7, and the coil springs 22 to the distal direction are permitted on condition that the condition where the thread support portion 15 is inhibited by the stopper 35 from moving is canceled, whereby an operation of causing the coil springs 22 to actuate is permitted Incidentally, the lever 28 and the lock portion 29 constitute changeover means for changeover between the locked condition where an operation of causing the pair of coil springs (actuating members) 22 to actuate by trigger means is inhibited and the unlocked condition where this operation is permitted Now, procedure of performing a stanching work by use of the tissue closing device 1 and the operations of the tissue closing device 1 will be described below As shown in FIG. 33(*b*), after a procedure in therapeutic treatment (PCI) or diagnosis (CAG) using catheters, a sheath 5 is indwelling, and the sheath 5 is used for the stanching work A distal end portion of the sheath 5 is passing through a wound hole and inserted in a blood vessel As shown in FIGS. 30 and 31, in the initial condition, the lever 28 is located at the lock position, the projected portion 291 of the lock portion 29 abuts on the distal end side of the projection 346 of the slide connecting member 34, and the projection 346 is locked by the projected portion 291, whereby the slide connecting member 34 is inhibited from moving to the distal direction First, as shown in FIGS. 33(*a*) and 33(*b*), the operator (user) gradually insert the arrangement device 3 into the through-lumen 51 in the sheath 5 from the proximal side of the sheath 5 Then, in the condition where the position of the distal end portion of the slot 313 in the inner tube portion 311 of the connector 31 coincides with the position of the distal end portion of the slot 314 in the outer tube portion 312, the hub 52 of the sheath 5 is pressed against the base portion 321 of the first charging member 32 While pushing the first charging member 32 in the proximal direction, the proximal end portion of the hub 52 is inserted into the inner tube portion 311 so that the port portion 53 of the hub 52 of the sheath 5 will be located at the distal end portion of the slot 313 in the inner tube portion 311 and the distal end portion of the slot 314 in the outer tube portion 312 As a result of this, the sheath 5 is tentatively mounted to the arrangement device 3 (the casing 11)

In addition, at the time of this tentative mounting, the second charging member 33 is moved to the proximal direction together with the first charging member 32, whereby the coil springs 22 are gradually contracted (deformed, activated, charged) while being clamped between the second charging member 33 and the thread support portion 15 Then, the pair of pawls 335 of the second charging member 33 are engaged with the base portion 341 of the slide connecting member 34, thereafter the proximal end portions 325 of the pair of rod-like elements 322 of the first charging member 32 are inserted into the pair of grooves 91 in the casing 11 (see FIG. 31), the spacing between the proximal end portions 325 of the rod-like elements 322 is enlarged (see FIG. 31), and the engagement between the pair of recessed portions 336 in the distal end portion of the second charging member 33 and the pair of projected portions 323 of the first charging member 32 is released (see FIG. 31)

Figure 34:
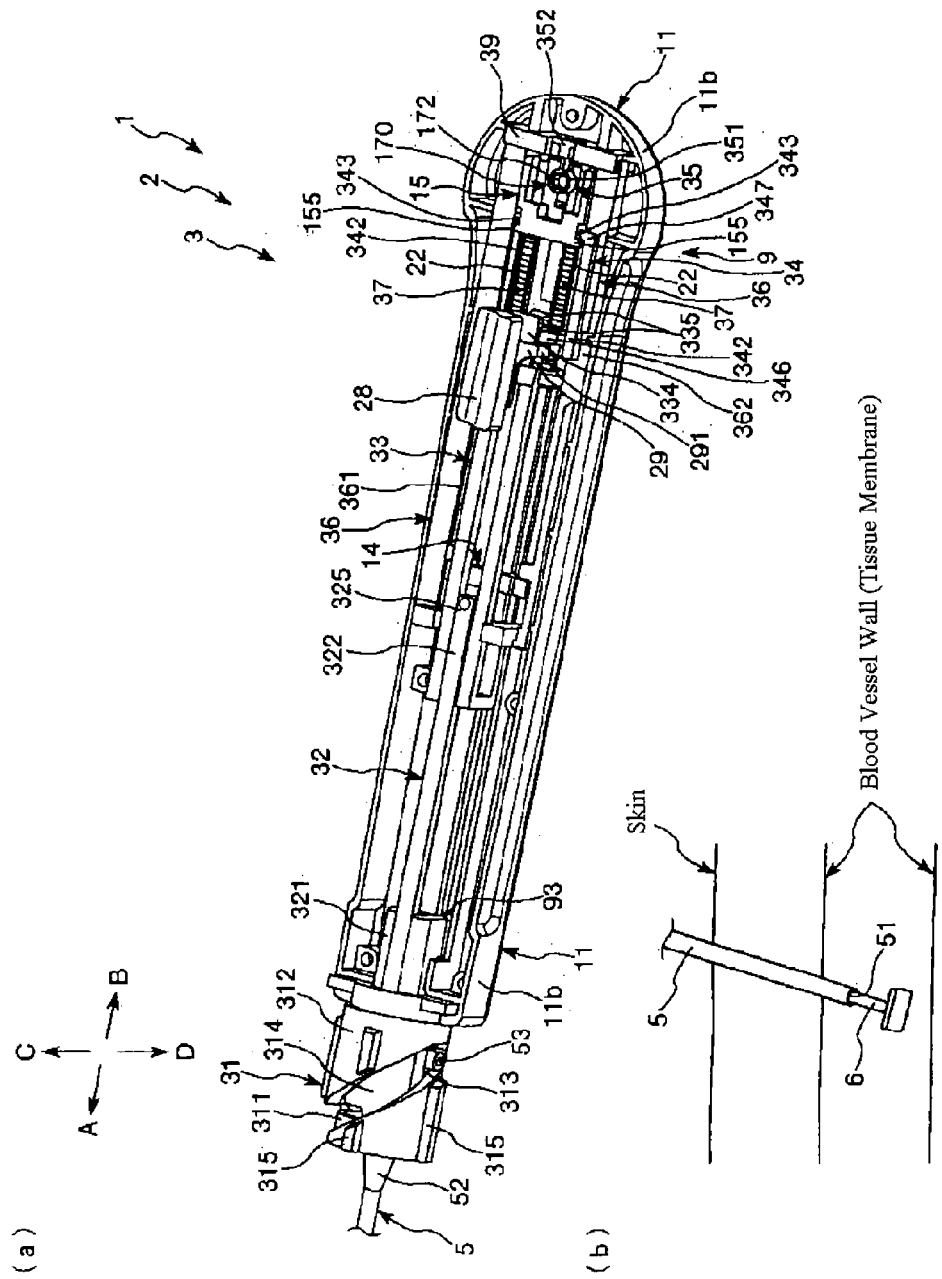
FIGS. 34(a) and 34(b) are perspective views for illustrating an action (operation) of the tissue closing device shown in FIG. 30
Figure 35:
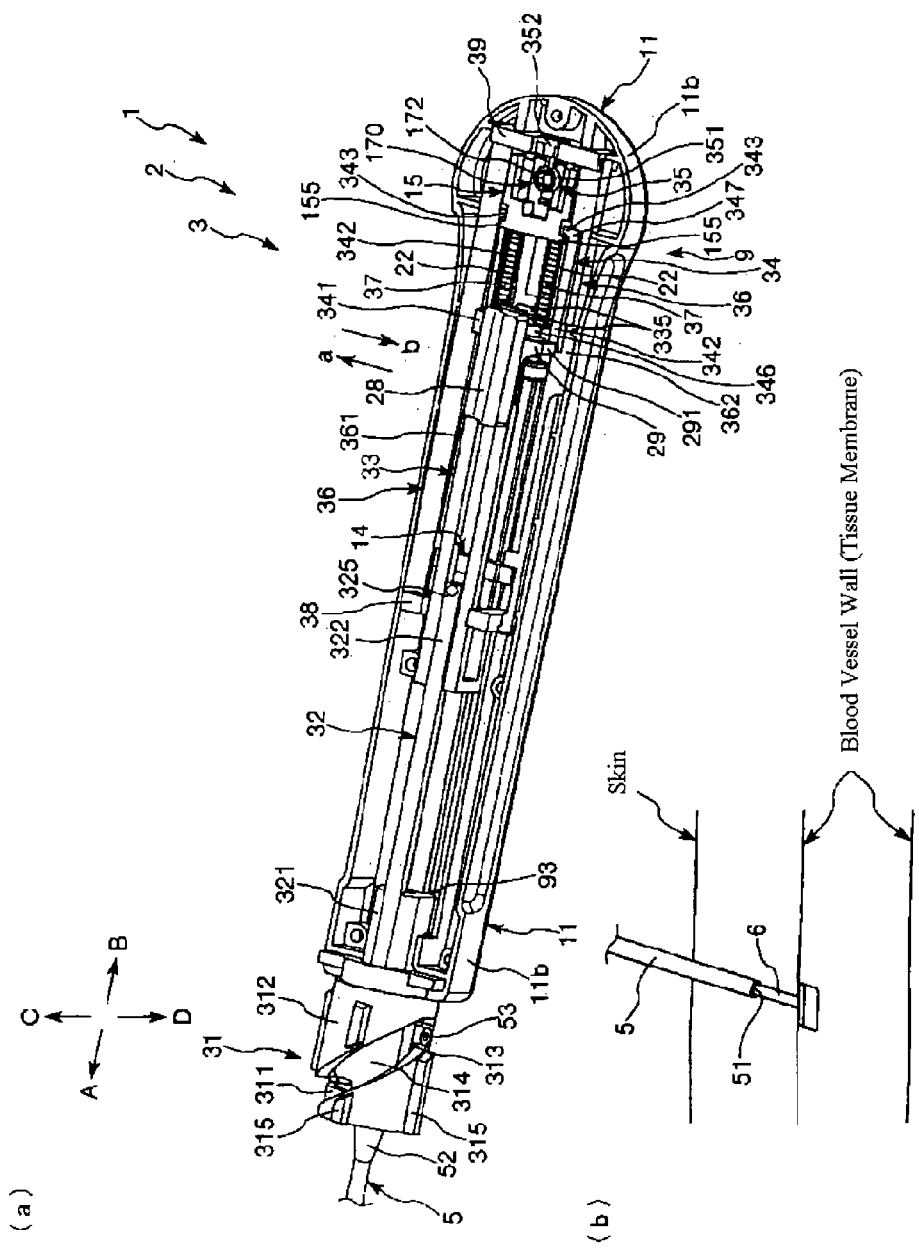
FIGS. 35(a) and 35(b) are perspective views for illustrating an action (operation) of the tissue closing device shown in FIG. 30
Figure 36:
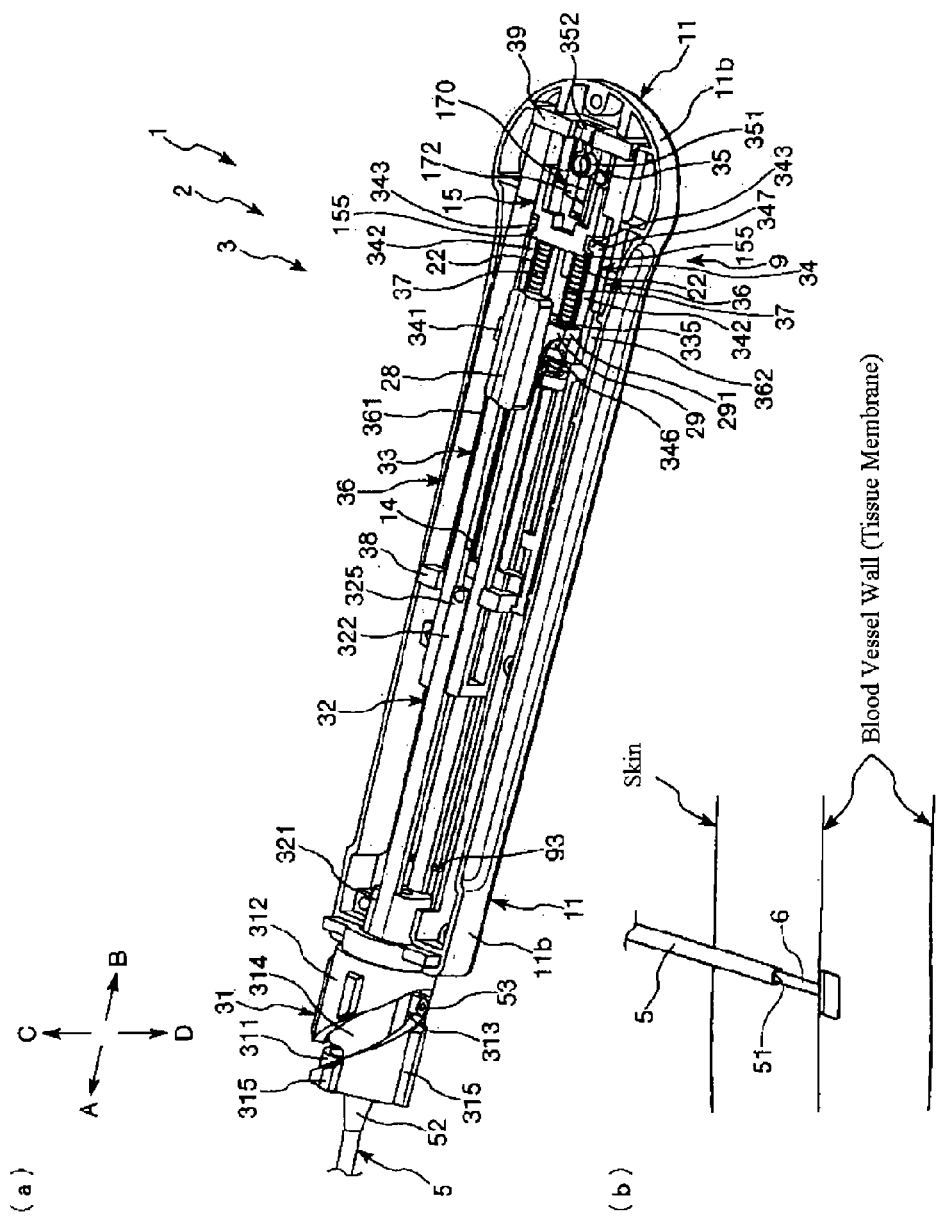
FIGS. 36(a) and 36(b) are perspective views for illustrating an action (operation) of the tissue closing device shown in FIG. 30
Figure 37:
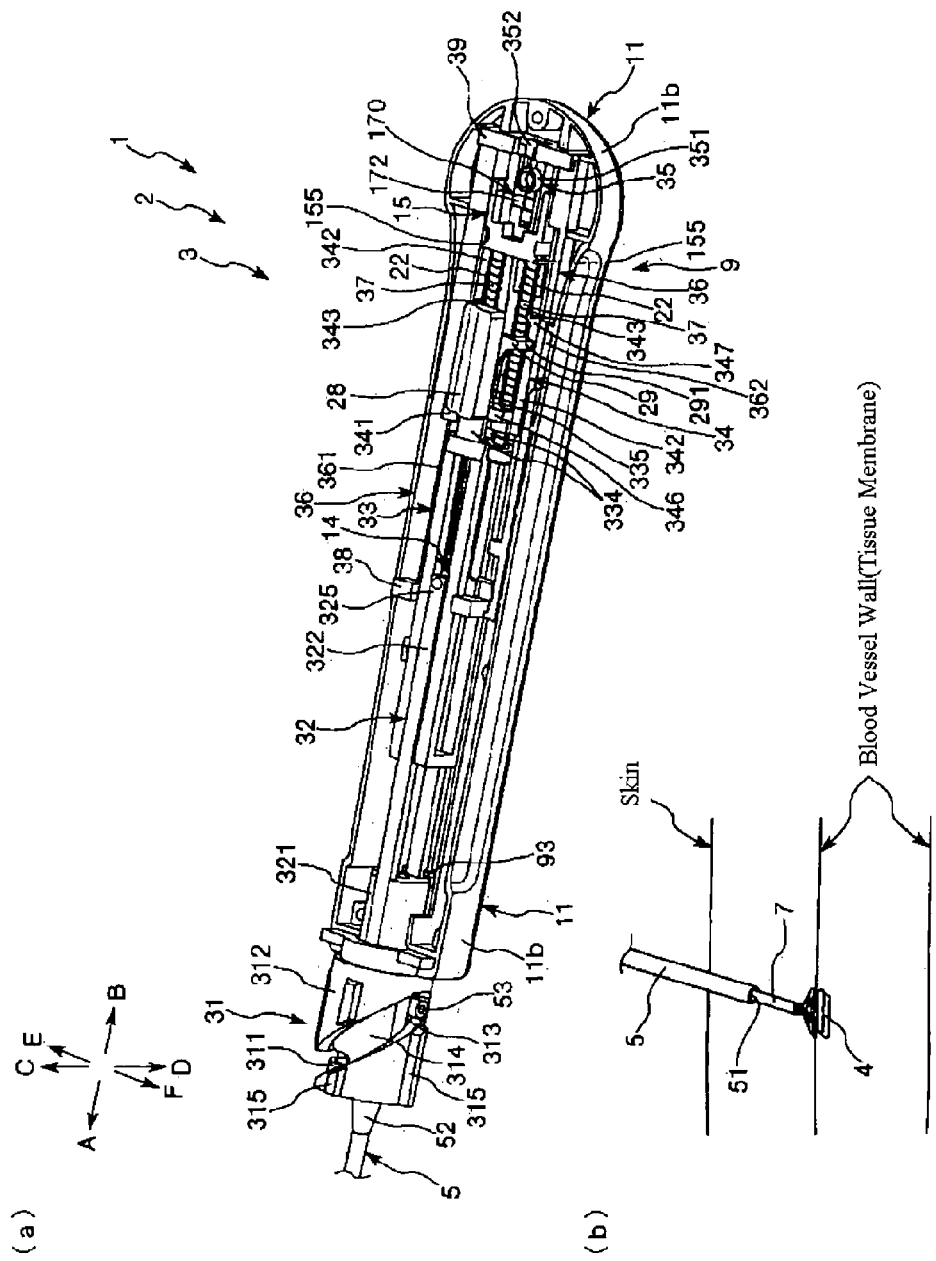
FIGS. 37(a) and 37(b) are perspective views for illustrating an action (operation) of the tissue closing device shown in FIG. 30
Figure 38:
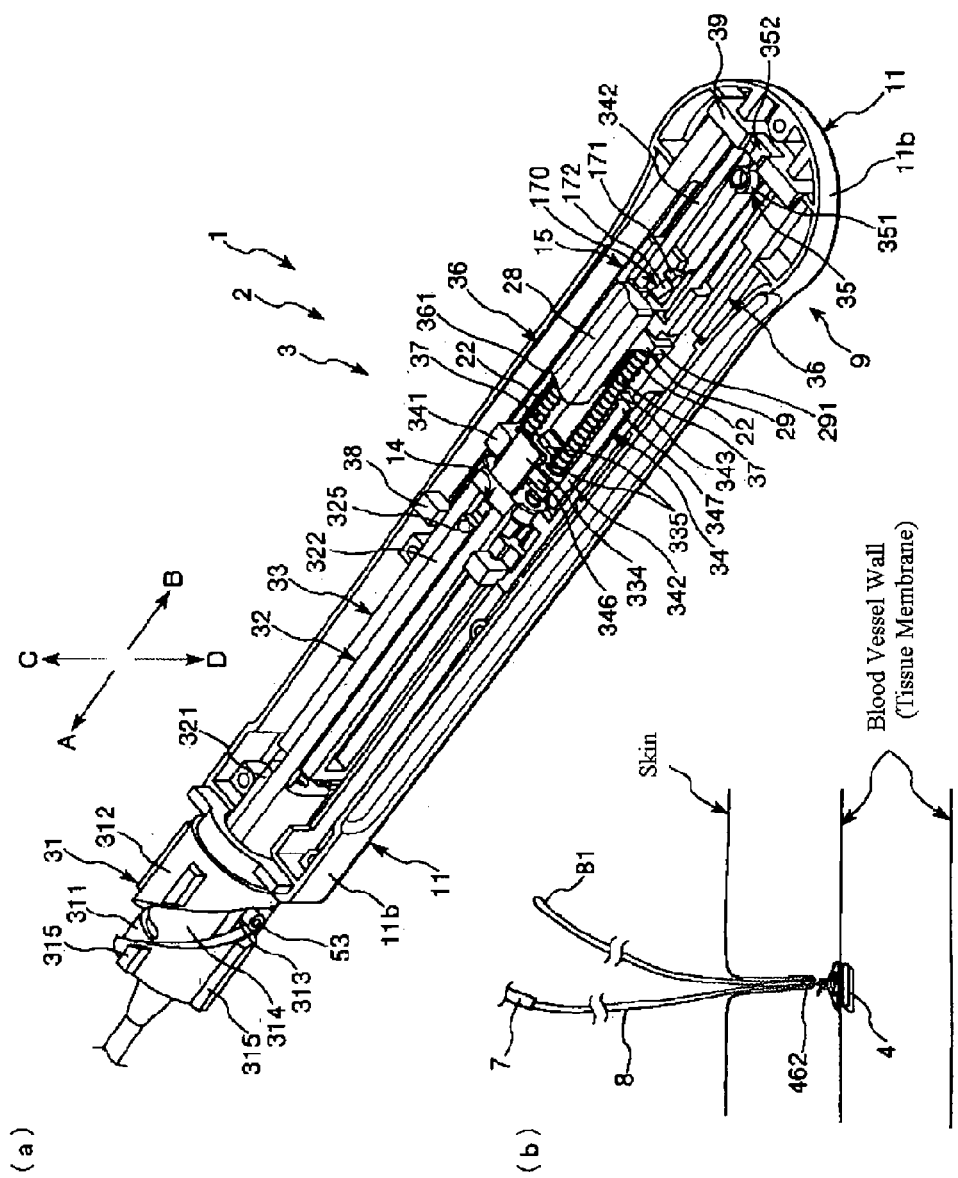
FIGS. 38(a) and 38(b) are perspective views for illustrating an action (operation) of the tissue closing device shown in FIG. 30
Figure 39:
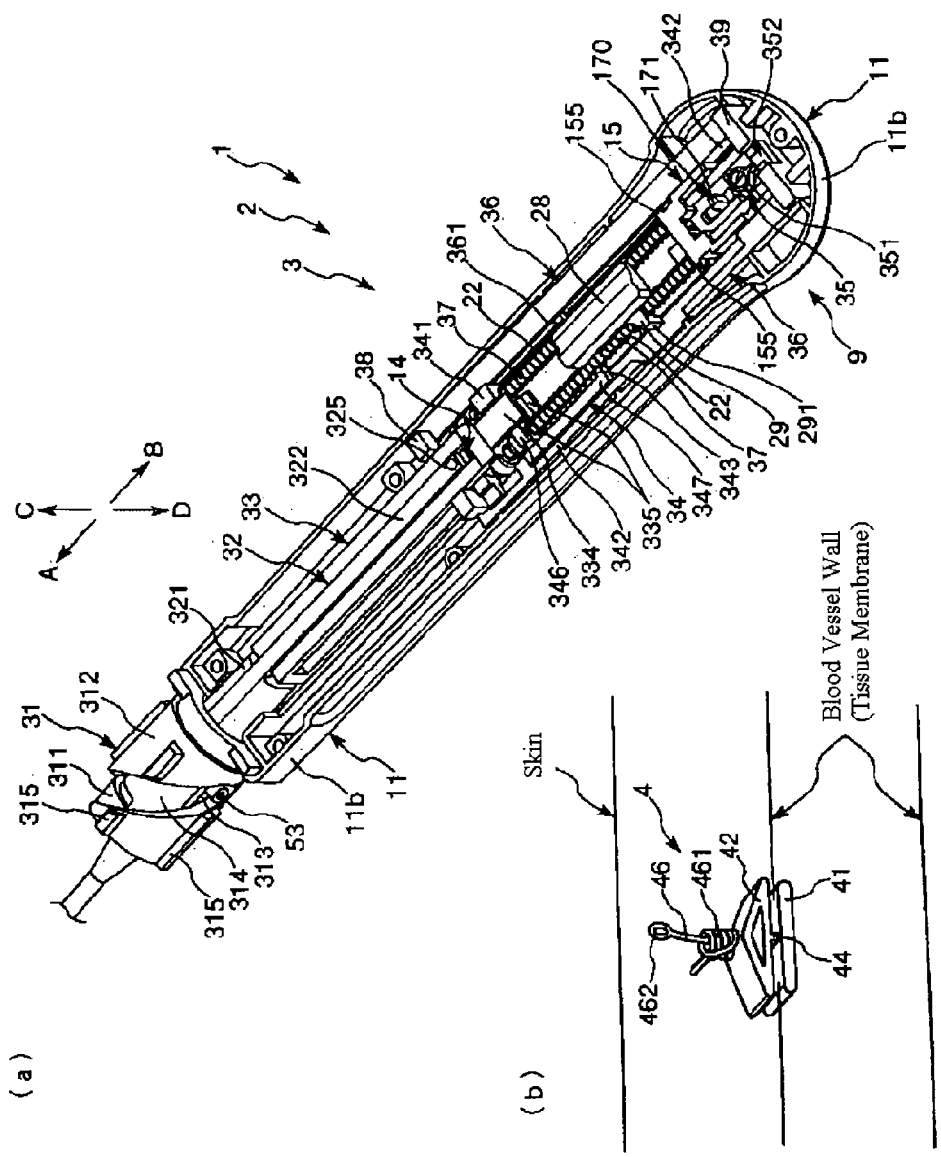
FIGS. 39(a) and 39(b) are perspective views for illustrating an action (operation) of the tissue closing device shown in FIG. 30

This results in that the second charging member 33 cannot move relative to the slide connecting member 34 and the thread support portion 15, the coil, springs 22 are retained in the contracted state (deformed state, active state), and the fixed tube 7 is held (substantially fixed) by the second charging member 33 and the slide connecting member 34 (the thread support portion 15 is inhibited from moving in the proximal direction relative to the fixed tube 7) In other words, the positional, relationships among the second charging member 33, the slide connecting member 34, the thread support portion 15, the fixed tube 7, and the coil springs 22 are fixed, and these can be moved as one body This condition is referred to as the charged condition In this tentatively mounted condition, the clip 4 (the seal portion 41 of the clip 4) is stored in the through-hole (lumen) 51 in the sheath 5 Therefore, at the time of inserting the proximal end portion of the hub 52 of the sheath 5 into the inner tube portion 311 to realize the charged condition, the clip 4 would not damage the blood vessel wall, thus, very good safety is secured Next, as shown in FIGS. 34(*a*) and 34(*b*), the outer tube portion 312 is rotated in a predetermined sense (in the example shown, counterclockwise as viewed from the distal side) By this, the port portion 53 is pushed in the proximal direction by an edge portion fronting on the slot 314 of the outer tube portion 312 and is thereby gradually moved to the proximal direction along the slot 313 in the inner tube portion 311 The seal portion 41 of the clip 4 and the cover tube 6 gradually protrude from the distal end portion of the sheath 5 In other words, the hub 52 of the sheath 5 is moved to the proximal direction, to be inserted and fixed in the inner tube portion 311. Besides, in this case, the first charging member 32 is pushed by the sheath 5 and moved to the proximal direction Incidentally, the first charging member 32 is inhibited from moving to the proximal direction beyond the pair of projections 93 of the casing 11, since the base portion 321 of the first charging member 32 abuts on the projections 93 In addition, since the engagement between the first charging member 32 and the second charging member 33 has already been released, the second charging member 33 is not moved As a result, the sheath 5 is mounted to the arrangement device 3, in addition, a distal end portion of the cover tube 6 protrudes from the distal end portion of the sheath 5, and the seal portion 41 of the clip 4 also protrudes, to be inserted in the blood vessel Thus, in the tentatively mounted condition where the hub 52 of the sheath 5 is inserted in the inner tube portion 311, the clip 4 is stored in the through-lumen 51 in the sheath 5 Besides, when the outer tube portion 312 is operated to rotate starting from the tentatively mounted condition, the hub 52 of the sheath 5 is gradually moved to the proximal direction, to be inserted in the inner tube portion 311, so that the seal portion 41 of the clip 4 can be securely prevented from, abruptly protruding from the distal end of the sheath 5 toward the blood vessel wall Therefore, the sheath 5 can be mounted to the arrangement device 3 easily, assuredly, and in safety Next, the casing 11 of the handling portion 9 is gripped by fingers of a hand, and the handling portion 9, or the main body portion 2 (the arrangement device 3), is slowly moved to one direction, i e, to a direction for pulling out of the wound hole (in the proximal direction), with the result that the wound hole and the surrounding area are covered by the seal portion 41 of the clip 4 from the inside of the blood vessel wall (positioning of the seal portion 41 is done) (see FIG. 35B) The deformation portion 42 of the clip 4 is moved to the outside of the blood vessel In the work (operation) of covering the wound hole and the surrounding area with the seal portion 41, at the time of moving the main body portion 2 to the direction of pulling out of the wound hole, the operator senses the resistance upon abutment of the seal portion 41 on the wound hole and the surrounding tissue (surface abutment resistance), whereon the operator judges that the seal portion 41 has come into abutment (surface abutment) on the wound hole and the surrounding tissue Hence, the positioning of the seal portion 41 is completed In this case, the members for connecting the clip 4, the thread 15, and the casing 11 to one another in the longitudinal direction of the arrangement device 3 do not include any member such as a spring that will extend or contract in the longitudinal direction of the arrangement device 3, and the distance between the clip 4 and the casing 11 is kept substantially constant Therefore, the operator can sense the force exerted on the seal portion 41 of the clip 4 directly through his fingers, whereby the resistance upon abutment of the seal portion 41 of the clip 4 on the wound hole and the surrounding tissue can be sensed accurately In addition, the second charging member 33, the slide connecting member 34, the thread support portion 15, the fixed tube 7, and the coil springs 22 are inhibited by the lock portion 29 from moving to the distal direction, so that the coil springs 22 can be securely prevented from actuating before the positioning of the seal portion 41 is completed This ensures that the positioning of the seal portion 41 of the clip 4 can be conducted easily and assuredly Next, as shown in FIGS. 35(a) and 35(b), the lever 28 is moved to the direction of arrow "b", to be located in an unlocking position As a result, the lock portion 29 is moved in the direction of arrow "b", the projected portion 291 thereof is moved (retracted) to a lateral side relative to the projection 346 of the slide connecting member 34 (to a position where the projection 346 is absent), and the projection 346 is unlocked from the projected portion 291 This ensures that the movement of the second charging member 33, the slide connecting member 34, the thread support portion 15, the fixed tube 7, and the coil springs 22 in the distal direction is permitted on condition that the inhibition of the thread support portion 15 from movement by the stopper 35 is released Next, the main body portion 2 (the arrangement device 3) is slowly moved to the direction of pulling out of the wound hole (in the proximal direction), and the main body portion 2 is pulled out of the wound hole By this, all the operations, (movements) are performed sequentially and continuously, whereby the wound hole is closed with the clip 4, and the clip 4 is disposed (made to indwell) in the living body Now, the procedure and operations in this case will be described in detail below First, as shown in FIGS. 36(a) and 36(b), when the handling portion 9 (the casing 11) is moved to the proximal direction, the thread support portion 15 is pulled in the distal direction through the thread 8, since the seal 41 of the clip 4 is abutting on the inside surface of the blood vessel wall (the surface remote from the body surface) When the force (pulling force) exerted on the thread support portion 15 through the thread 8 exceeds the predetermined threshold, the projection 172 of the pin 170 comes out of the gap in the stopper body 351 of the stopper 35, and the second charging member 33, the slide connecting member 34, the thread support portion 15, the fixed tube 7, and the coil springs 22 are moved as one body to the distal direction relative to the casing 11

Here, in the positioning of the seal portion 41 in the condition where the slide connecting member 34 is inhibited by the lock portion 29 from moving in the distal direction, even if the positioning is unsatisfactory because the clip 4 is caught in the blood vessel, for example, the clip 4 can be expected to be released before the pin 170 comes off from the stopper 35 (the locking is canceled), so that the clip 4 can be moved to the wound hole and the seal portion 41 thereof can be made to abut on the wound hole and the surrounding tissue Thus, the operation of positioning the seal portion 41 of the clip 4 is performed doubly, so that the seal portion 41 can be made to abut on the wound hole and the surrounding tissue assuredly When the second charging member 33, the slide connecting member 34, the thread support portion 15, the fixed tube 7, and the coil springs 22 are moved to the distal direction relative to the casing 11, the deformation portion 42 of the clip 4 is moved together with the fixed tube 7 to the distal direction relative to the cover tube 6, and the deformation portion 42 comes off from the distal end portion of the cover tube 6, resulting in that the deformation portion 42 can be deformed When the proximal end portions 347 of the pair of rod-like elements 342 of the slide connecting member 34 are moved until they are located in the hole portions 362 in the pair of rails 36 as shown in FIGS. 37(a) and 37(b), the proximal end portions 347 of the rod-like elements 342 come to be movable (displaceable) sideways (to the directions of arrows E and F) On the other hand, the slide connecting member 34 is biased in the distal direction relative to the thread support portion 15 by the restoring forces of the coil springs 22 By the biasing force, therefore, the proximal end portions 347 of the rod-like elements 342 are moved roughly sideways along the projections 155 so as to be inserted (retracted) into the hole portions 362, and the pawls 343 of the rod-like elements 342 come off the projections 155 of the thread support portion 15

As a result, the connection between the thread support portion 15 and the second charging member 33 by the slide connecting member 34 is canceled, and it becomes possible for the thread support portion 15 to move to the proximal direction relative to the second charging member 33, the slide connecting member 34, and the fixed tube 7 In addition, with the connection between the thread support portion 15 and the second charging member 33 by the slide connecting member 34 thus canceled, relative movements between the thread support portion 15 and the second charging member 33, the slide connecting member 34 and the fixed tube 7 are permitted, and the restriction to hold the coil springs 22 in the deformed state (active state) is canceled As a result, the thread support portion 15 is moved by the restoring forces of the coil springs 22 in the proximal direction relative to the second charging member 33, the slide connecting member 34, and the fixed tube 7 In this manner, the slide connecting member 34, the pair of projections 155 of the thread support portion 15, the pair of projected portions 334 of the second charging member 33, and the hole portions 362 in the pair of rails 36 function as trigger means for putting into actuation the coil springs 22 by canceling the restriction to hold the coil springs 22 in the active state In addition, the slide connecting means 34, the pair of projections 155 of the thread support portion 15, and the pair of projected portions 334 of the second charging member 33 function as restricting means for holding the coil springs 22 in the active state Further, the operation (triggering operation) of moving the proximal end portions 347 of the rod-like elements 342 of the slide connecting member 34 connecting the thread support portion 15 and the second charging member 33 sideways (in the direction in which the pawls 343 of the rod-like elements 342 come off from the projections 155 of the thread support member 15) is automatically performed by the operator's action of pulling out (moving) the handling portion 9 in the proximal direction and by the biasing forces of the coil springs 22

When the thread support portion 15 is moved to the proximal direction relative to the fixed tube 7, as shown in FIG. 37(b) and FIG. 22 of the first embodiment, the thread 8 is moved to the proximal direction, the thread 46 of the clip 4 is pulled by the thread 8 in the proximal direction, and a knot 461 of the thread 46 of the clip 4 is locked by a distal end portion 71 of the fixed tube 7, further, the deformation portion 42 is locked through the knot 461 (locked indirectly), whereby the knot 461 is moved to the distal direction, the thread 46 is tightened, and the deformation portion 42 is deformed As a result, the deformation portion 42 covers the wound hole and the surrounding area from the outside of the blood vessel wall, the seal portion 41 covers the wound hole and the surrounding area from the inside of the blood vessel wall, and the blood vessel wall is sandwiched by the seal portion 41 and the deformation portion 42, whereby the wound hole is closed Then on, the condition where the deformation portion 42 assumes the above-mentioned form is retained (fixed) by the thread 46.

In addition, after the connection between the thread support portion 15 and the second charging member 33 by the slide connecting member 34 is canceled (the restriction to hold the coil springs 22 in the deformed state is canceled), i e, after the deformation of the deformation portion 42 of the clip 4 is completed, when the handling portion 9 (the casing 11) is further moved to the proximal direction under the condition where the seal portion 41 of the clip 4 abuts on the inside surface of the blood vessel wall as shown in FIGS. 38(a) and 38(b), the casing 11 is further moved to the proximal direction relative to the thread support portion 15 The thread support portion 15 is further moved to the distal direction relative to the casing 11

When the pin 170 provided at the thread support portion 15 is moved until it is located on the distal side relative to a distal end portion of the rib 92 of the casing 11, the pin 170 is turned at the step portion 921 and the projection 172 thereof falls flat As a result of this, the connection between the thread 8 and the thread support portion 15 by the pin 170 is canceled, whereby the connection between the thread 8 and the thread 46 of the clip 4 is canceled (the condition where the clip 4 is retained by the thread 8 is canceled) Specifically, the bent-back portion 81 of the thread 8 is released from the projection 172 of the pin 170, resulting in that the thread 8 can be pulled out from the loop 462 of the thread 46 Therefore, the step portion 921 constitutes disconnecting means and retained condition canceling means When the handling portion 9 (the casing 11) is further continuously moved to the proximal direction, first, only the main body portion 2 is evulsed from the patient (up to distal end portions of the sheath 5, the cover tube 6, and the fixed tube 7) At this stage, as shown in FIG. 38(b), the bent-back portion 81 of the thread 8 is located in, the exterior of the patient's body without being pulled out of the loop 462 of the thread 46 of the clip 4, and the clip 4 is retained by the thread 8

To be more specific, in the tissue closing device 1, the length of the thread 8 is set to be comparatively large, on the basis of structure and mechanism, so that at the stage immediately upon the evulsion of the main body portion 2 from the patient, the bent-back portion 81 of the thread 8 has not yet been pulled out of the loop 462 of the thread 46 of the clip 4, the clip 4 is retained by the thread 8, and the bent-back portion 81 of the thread 8 is located in the exterior of the patient's body Therefore, where the main body portion 2 and the bent-back portion 81 of the thread 8 are gripped by the operator, the clip 4 can be retained (secured) through the thread 8, whereby it is made possible to cope with various situations, and a very high safety is realized In this case, for example, the operator can take out the clip 4 present in the blood vessel by an operation, while retaining it through the thread 8

If there is no problem, as shown in FIGS. 39(a) and 39(b), the handling portion 9 (the casing 11) is further moved to the proximal direction, and the thread 8 is evulsed from the patient As a result, the clip 4 is disposed (made to indwell) in the living body According to this tissue closing device 1, the same effects as those of the tissue closing device 1 in the first embodiment described above can be obtained In addition, according to this tissue closing device 1, a simpler structure is realized as compared with that in the first embodiment, and the various effects as above-mentioned can be obtained While the tissue closing device has been described above based on the embodiments shown in the drawings, the present invention is not limited to the embodiments, and the configurations of the components may be replaced by arbitrary configurations having the same or equivalent functions Besides, other arbitrary components may be added to the configuration according to the present invention In addition, the configuration of the present invention may be a combination of arbitrary two or more configurations (features) of the above-described embodiments For example, a member corresponding to the lever 28 and the lock portion 29 in the third embodiment, i e, changeover means for changeover between a locked condition where an operation of putting the coil springs (first elastic member) (actuating member) 22 into actuation by triggering means is inhibited and an unlocked condition where this operation is permitted, may be provided in the first embodiment and the second embodiment In addition, the connector 121 in the first embodiment and the second embodiment may be replaced by the connector 31 in the third embodiment, and the connector 31 in the third embodiment may be replaced by the connector 121 in the first embodiment and the second embodiment Besides, while one of the two end portions of the thread 8 is fixed in the handling portion 9 and the other is disconnected in the above embodiments, a configuration in which both of the end portions are disconnected may be adopted in the present invention In such a configuration, the thread 8 is left on the living body side in the state of being connected to the clip 4 Thereafter, the thread 8 can be freely evulsed by an operator's operation

The invention claimed is:

1. A tissue closing device for closing an opening penetrating a living tissue, comprising:
   a closure for closing the opening, the closure comprising a seal portion adapted to cover the opening and a periphery of the opening from one side of a wall of a living body cavity, and a deformable deformation portion; and
   an arrangement device detachably retaining the closure to arrange the closure at a position to close the opening, the arrangement device comprising:
   a lock member having an elongate shape such as to be able to pass through the opening and locking at least a part of the closure in a retained state;

a handling portion provided on the proximal side of the lock member;

the handling portion comprises an elastic member configured to apply a force that moves the closure and the lock member relative to each other, and a movable trigger means movable to an actuating position for actuating the elastic member;

wherein with the elastic member actuated by the trigger means, the elastic member applies the force that moves the closure and the lock member relative to each other while the closure is locked by the lock member to thereby deform the deformation portion;

the trigger means comprising a restrictor configured to be positioned in one position in which the restrictor retains the elastic member in an active state and prevents the elastic member from applying the force that moves the closure and the lock member relative to each other, the restrictor also being configured to be positioned in another position in which the restrictor no longer retains the elastic member so that the elastic member applies the force that moves the closure and the lock member relative to each other, the restrictor moving from the one position to the other position when the trigger means is moved to the actuating position; and the trigger means being configured so that movement of the handling portion in a proximal direction away from the closure while the seal portion is in contact with a surface of the living tissue at a distal side from a skin surface causes, by itself, the trigger means to automatically move to the actuating position, so that the restrictor moves to the other position and the elastic member applies the force that moves the closure and the lock member relative to each other.

2. The tissue closing device as set forth in claim 1, wherein the arrangement device has a retaining member for retaining the closure so that a portion of the closure on the opposite side of the seal portion of the deformation portion can be moved relative to a portion on the side of the seal portion of the deformation portion.

3. The tissue closing device as set forth in claim 2, wherein when the trigger means moves to the actuating position, the retaining member is moved to the proximal direction by a restoring force of the elastic member so that the retaining member pulls the closure, in the condition where the deformation portion of the closure is locked to a distal end portion of the lock member, whereby the deformation portion is deformed.

4. The tissue closing device as set forth in claim 2, wherein:
the lock member has a lumen; and the retaining member is inserted in the lumen.

5. The tissue closing device as set forth in claim 2, wherein:
the handling portion comprising:
a lock member support portion for supporting the lock member, and
a retaining member support portion which is provided to be movable relative to the lock member support portion and supports the retaining member.

6. The tissue closing device as set forth in claim 5, wherein said active state of the elastic member is a contracted state; and
when the trigger means moves to the actuating position, the retaining member support portion is moved to the proximal direction relative to the lock member support portion by a restoring force of the elastic member.

7. The tissue closing device as set forth in claim 5, wherein the handling portion has a casing, and the lock member support portion is provided to be movable relative to the casing.

8. The tissue closing device as set forth in claim 7, wherein:
the restrictor has a stopper for locking the retaining member support portion, and retains the elastic member in the active state by locking the retaining member support portion with the stopper and thereby inhibiting relative movements of the retaining member support portion and the lock member support portion; and
when the casing is moved to the proximal direction in the condition where the seal portion is in contact with a surface of the living tissue which is distal side from a skin surface, the casing is moved relative to the lock member support portion, and the trigger moves to the actuating position when the casing is moved to a predetermined position relative to the lock member support portion.

9. The tissue closing device as set forth in claim 7, wherein
the handling portion comprises in the casing a second elastic member for energizing the retaining member support portion in the proximal direction through the lock member support portion in the condition where the positional relationship between the retaining member support portion and the lock member support portion is substantially fixed; and
when the casing is moved to the proximal direction in the condition where the seal portion is in contact with a surface of the living tissue which is distal side from a skin surface, the casing is moved relative to the lock member support portion, attended by a deformation of the second elastic member, and the lock member support portion is energized in the proximal direction by a restoring force of the second elastic member, whereby the retaining member support portion is energized in the proximal direction.

10. The tissue closing device as set forth in claim 5, wherein the handling portion comprises a second elastic member energizing the retaining member support portion in the proximal direction in the condition where a positional relationship between the retaining member support portion and the lock member support portion is substantially fixed.

11. The tissue closing device as set forth in claim 10, wherein the canceling by the trigger means of the restriction for retaining the first elastic member in the active state is permitted on the condition that the energizing force of the second elastic member have exceeded a predetermined threshold.

12. The tissue closing device as set forth in claim 11, wherein when the energizing force of the second elastic member has exceeded the threshold, the energizing force is reduced or lost.

13. The tissue closing device as set forth in claim 5, wherein
the arrangement device comprises a cover member for covering an outer surface of the lock member and covering at least a part of the closure at a distal end portion of the cover member thereof;
the handling portion comprises a cover member support portion provided to be movable relative to the lock member support portion and supporting the cover member; and
the deformation portion of the closure comes off the distal end portion of the cover member when the cover member support portion is moved to the proximal direction.

14. The tissue closing device as set forth in claim 13, wherein
the handling portion comprises a connector configured to connect between the retaining member and the retaining member support portion, and a disconnection means configured to cancel the connection between the retaining member and the retaining member support portion; and the connection between the retaining member and the retaining member support portion is canceled by the disconnection means so that the retained state of the closure by the retaining member is canceled.

15. The tissue closing device as set forth in claim 14, wherein the disconnection means cancels the connection between the retaining member and the retaining member support portion by the connector, through a movement of the cover member support portion to the proximal direction.

16. The tissue closing device as set forth in claim 14, wherein
the disconnection means comprising:
a connector support portion provided to be displaceable relative to the retaining member support portion and operative to support the connector, and
a displacement portion provided in the cover member support portion and operative to displace the connector support portion; and
when the cover member support portion is moved to the proximal direction after the restriction for retaining the first elastic member in the active state is canceled, the connector support portion is displaced by the displacement portion, whereby the connection between the retaining member and the retaining member support portion by the connection portion is canceled.

17. The tissue closing device as set forth in claim 14, wherein
the retaining member is a thread-like member having two end portions; and
in the condition where the thread-like member is threaded through the closure and turned back at a distal end portion of the arrangement device and is retaining the closure, at least one end portion of the thread-like member is detachably connected to the retaining member support portion by the connector.

18. The tissue closing device as set forth in claim 2, wherein the closure comprises a fastener for retaining, in the condition where the deformation portion is in a predetermined form, the condition.

19. The tissue closing device as set forth in claim 18, wherein
the fastener is a thread-like member having a movable knot; and
when the restrictor is moved to the other position, the retaining member is moved to the proximal direction by a restoring force of the elastic member so that the retaining member pulls the closure, in the condition where the knot is locked to a distal end portion of the lock member, and the knot is moved on the thread-like member of the fastener, whereby the deformation portion is deformed into a predetermined form and this condition is retained.

20. The tissue closing device as set forth in claim 19, wherein the knot is a clinch knot.

21. The tissue closing device as set forth in claim 18, wherein the retaining member retains the fastener of the closure.

22. The tissue closing device as set forth in claim 2, wherein
the handling portion includes a casing, and
a retaining member support portion for supporting the retaining member, the retaining member support portion provided in the casing, and
the movement of the restrictor to the other position when the trigger means reaches the actuating position becomes possible on condition that a force exerted on the retaining member support portion through the retaining member has exceeded a predetermined threshold.

23. The tissue closing device as set forth in claim 22, wherein the distance between the closure and the casing is kept substantially constant until the force exerted on the retaining member support portion through the retaining member exceeds the predetermined threshold, in the condition where the elastic member is retained in the active state.

24. The tissue closing device as set forth in claim 2, wherein
the handling portion includes a casing,
a retaining member support portion for supporting the retaining member, the retaining member support portion provided in the casing in the manner of being movable relative to the casing, and
a stopper for inhibiting the retaining member support portion from moving, until a force exerted on the retaining member support portion through the retaining member exceeds a predetermined threshold, and
when the force exerted on the retaining member support portion through the retaining member has exceeded the predetermined threshold, the retaining member support portion becomes movable, whereby the canceling of the restriction for retaining the elastic member in an active state by the trigger means becomes possible.

25. The tissue closing device as set forth in claim 1, wherein
the restrictor retains the elastic member in the active state by inhibiting relative movements of the closure and the lock member; and
the trigger means moves to the actuating position by enabling relative movements of the closure and the lock member.

26. The tissue closing device as set forth in claim 1, wherein
the arrangement device comprises a cover member for covering an outer surface of the lock member and covering at least a part of the closure at a distal end portion of the cover member thereof; and
the deformation portion of the closure comes off the distal end portion of the cover member when the cover member is moved to the proximal direction relative to the deformation portion.

27. The tissue closing device as set forth in claim 1, wherein the arrangement device comprises retained state canceling means for canceling the retained state of the closure.

28. The tissue closing device as set forth in claim 1, wherein the handling portion comprises a charge means for deforming the elastic member to provide the condition where the elastic member is retained in the active state by the restrictor.

29. The tissue closing device as set forth in claim 1, wherein
the tissue closing device is used with the arrangement device inserted in a sheath and with the sheath mounted to the arrangement device, and
the tissue closing device includes a sheath mounting mechanism for moving the sheath relative to the arrangement device so as to mount the sheath to the arrangement device.

30. The tissue closing device as set forth in claim 29, wherein
in mounting the sheath to the arrangement device, the sheath is tentatively mounted to the arrangement device so as to put the closure into the state of being stored in the sheath, and the sheath mounting mechanism moves the sheath relative to the arrangement device from the tentatively mounted condition so as to protrude a seal portion of the closure from a distal end portion of the sheath, thereby mounting the sheath to the arrangement device.

31. The tissue closing device as set forth in claim 29, wherein the handling portion has a casing, and the sheath mounting mechanism is provided in the casing, and the sheath is mounted to the casing by the sheath mounting mechanism.

32. The tissue closing device as set forth in claim 1, further comprising changeover means for changeover between a locked condition where an operation of the trigger means to cause the actuating member to actuate is inhibited and an unlocked condition where the operation is permitted.

33. The tissue closing device as set forth in claim 1, wherein the seal portion has a plate-like shape; and the deformation portion has a frame-like shape and is deformable between a first form such as to be elongated in a direction substantially perpendicular to the seal portion and contracted in a direction substantially parallel to the seal portion and a second form such as to be contracted in a direction perpendicular to the seal portion and expanded in a direction substantially parallel to the seal portion.

34. The tissue closing device as set forth in claim 1, wherein the elastic member is a coil spring which applies the force that moves the closure and the lock member relative to each other when the restrictor is moved to the other position, the coil spring being compressed in the active state.

35. The tissue closing device as set forth in claim 1, wherein the lock member possessing the elongated shape extends in an axial direction, and wherein the elastic member is a coil spring which applies the force that moves the closure and the lock member relative to each other when the restrictor is moved to the other position, the coil spring applying the force in the axial direction.

36. A tissue closing device for closing an opening penetrating a living tissue comprising:

a closure positionable in a retained state relative to the opening in the living body tissue to close the opening, the closure comprising a seal portion configured to cover the opening penetrating the living tissue as well as a periphery of the opening from one side of a wall of a living body cavity, and a deformable deformation portion which is deformable to cover the opening penetrating the living tissue from an opposite side of the wall of the living body cavity; and an arrangement device to which the closure is detachably retained to arrange the closure at a position to close the opening in the living tissue, the arrangement device comprising:

a thread support;

a thread operatively connecting the closure to the thread support so that the closure is positioned distally of the thread support and so that a pulling force applied to the closure is transmitted to the thread support by way of the thread and is applied to the thread support;

a stopper holding the thread support to stop the thread support from moving in a distal direction when the pulling force applied to the thread support is less than a predetermined threshold and to release the thread support and permit the thread support to move in the distal direction when the pulling force applied to the thread support in the distal direction exceeds the predetermined threshold;

an elongated tubular member configured to pass through the opening in the living body and act on the closure to deform the deformation portion so that the deformation portion covers the opening from the opposite side of the wall of the living body cavity, the closure being positioned distally of a distal end of the elongated tubular member;

an elastic member positioned to apply an urging force between the elongated tubular member and the thread support which urges the thread support away from the elongated tubular member, the elastic member being arranged to apply the urging force in the distal direction and proximal direction;

the elongated tubular member and the thread support being operatively connectable to one another such that the elongated tubular member and the support member move together, and thereafter being operatively disconnectable from one another after the stopper releases the thread support to allow the thread support to move away from the elongated tubular member under the urging force of the elastic member and thus pull the thread proximally; and at least a portion of the arrangement device being movable in the proximal direction away from the closure while the seal portion is in contact with the surface of the wall on the one side of the wall to urge the thread support in the distal direction by way of the thread so that the stopper automatically releases the thread support when the pulling force applied to the thread support in the distal direction exceeds the predetermined threshold.

37. The tissue closing device as set forth in claim 36, wherein the elongated tubular member extends in an axial direction, and wherein the elastic member is a coil spring which applies the urging force in the axial direction.

38. The issue closing device as set forth in claim 36, wherein the elastic member is a coil spring possessing an axis extending in the distal direction and proximal direction.

39. A tissue closing device for closing an opening penetrating a living tissue, comprising:

a closure positionable in a retained state relative to the opening in the living body tissue to close the opening, the closure comprising a seal portion configured to cover the opening penetrating the living tissue as well as a periphery of the opening from one side of a wall of a living body cavity, and a deformable deformation portion which is deformable to cover the opening penetrating the living tissue from an opposite side of the wall of the living body cavity; and an arrangement device to which the closure is detachably retained to arrange the closure at a position to close the opening in the living tissue, the arrangement device comprising:

an elongated lock member configured to pass through the opening in the living body and act on the closure to lock at least a part of the closure in the retained state;

a stopper operatively connectable to the elongated lock member to fix the elongated lock member against movement in a distal direction when a distally directed pulling force applied to the stopper is less than a predetermined threshold, and operatively disconnectable from the elongated lock member to permit the elongated lock member to move in the distal direction relative to the stopper when the distally directed pulling force applied to the stopper exceeds the predetermined threshold;

an elastic member positioned to apply an urging force acting in the distal direction and proximal direction, the urging force being applied to the closure which urges the closure in the proximal direction relative to the elongated lock member to pull the closure towards the elongated lock member; and the stopper being configured so that upon applying a distally directed pulling force to the stopper that exceeds the predetermined threshold while the stopper and the elongated lock member are operatively connected, the stopper automatically releases the elongated lock member to allow the elongated lock member to move in the distal direction.

40. The tissue closing device as set forth in claim 39, wherein the elongated lock member extends in an axial direction, and wherein the elastic member is a coil spring which applies the urging force in the axial direction.

41. The issue closing device as set forth in claim 39, wherein the elastic member is a coil spring possessing an axis extending in the distal direction and proximal direction.

* * * * *